US00RE50636E

(19) United States
(12) Reissued Patent
Shum et al.

(10) Patent Number: US RE50,636 E
(45) Date of Reissued Patent: Oct. 14, 2025

(54) ACCURATE MOLECULAR BARCODING

(71) Applicant: Becton, Dickinson and Company, Franklin Lakes, NJ (US)

(72) Inventors: Eleen Shum, Redwood City, CA (US); Glenn Fu, Dublin, CA (US)

(73) Assignee: Becton, Dickinson and Company, Franklin Lakes, NJ (US)

(21) Appl. No.: 18/050,449

(22) Filed: Oct. 27, 2022

Related U.S. Patent Documents

Reissue of:
(64) Patent No.: 10,822,643
Issued: Nov. 3, 2020
Appl. No.: 15/581,914
Filed: Apr. 28, 2017

U.S. Applications:
(60) Provisional application No. 62/330,500, filed on May 2, 2016.

(51) Int. Cl.
*C12Q 1/6837* (2018.01)
*C12Q 1/6806* (2018.01)
*C12Q 1/6869* (2018.01)
*C12Q 1/6874* (2018.01)

(52) U.S. Cl.
CPC ..... *C12Q 1/6837* (2013.01); *C12Q 1/6806* (2013.01); *C12Q 1/6869* (2013.01); *C12Q 1/6874* (2013.01)

(58) Field of Classification Search
None
See application file for complete search history.

(56) References Cited

U.S. PATENT DOCUMENTS 4,510,244 A 4/1985 Parks et al.
4,725,536 A 2/1988 Fritsch et al.
5,124,246 A 6/1992 Urdea et al.
5,149,625 A 9/1992 Church et al.
5,200,314 A 4/1993 Urdea
5,424,186 A 6/1995 Fodor et al.
5,424,413 A 6/1995 Hogan et al.
5,445,934 A 8/1995 Fodor et al.
5,604,097 A 2/1997 Brenner
5,635,352 A 6/1997 Urdea et al.
5,635,400 A 6/1997 Brenner
5,648,245 A 7/1997 Fire et al.
5,654,413 A 8/1997 Brenner
5,656,731 A 8/1997 Urdea
5,658,737 A 8/1997 Nelson et al.
5,714,330 A 2/1998 Brenner et al.
5,744,305 A 4/1998 Fodor et al.
5,759,778 A 6/1998 Li et al.
5,763,175 A 6/1998 Brenner
5,800,992 A 9/1998 Fodor et al.
5,846,719 A 12/1998 Brenner et al.
5,854,033 A 12/1998 Lizardi
5,871,928 A 2/1999 Fodor et al.
5,925,525 A 7/1999 Fodor et al.
5,935,793 A 8/1999 Wong
5,962,271 A 10/1999 Chenchik et al.
5,962,272 A 10/1999 Chenchik et al.
5,968,740 A 10/1999 Fodor et al.
5,981,176 A 11/1999 Wallace
5,981,179 A 11/1999 Lorinez et al.
6,013,445 A 1/2000 Albrecht et al.
6,040,138 A 3/2000 Lockhart et al.
6,046,005 A 4/2000 Ju et al.
6,060,596 A 5/2000 Lerner et al.
6,064,755 A 5/2000 Some
6,114,149 A 9/2000 Fry et al.
6,117,631 A 9/2000 Nilsen
6,124,092 A 9/2000 O'neill et al.
6,138,077 A 10/2000 Brenner
6,140,489 A 10/2000 Brenner
6,172,214 B1 1/2001 Brenner
6,194,454 B1 * 2/2001 Dow ..... A61K 31/275 514/522
6,197,506 B1 3/2001 Fodor et al.
6,197,554 B1 3/2001 Lin et al.
6,235,475 B1 5/2001 Brenner et al.
6,235,483 B1 5/2001 Wolber et al.
6,265,163 B1 7/2001 Albrecht et al.
6,268,152 B1 7/2001 Fodor et al.
6,284,460 B1 9/2001 Fodor et al.
(Continued)

FOREIGN PATENT DOCUMENTS

DE 102008025656 12/2009
EP 0 799 897 10/1997
(Continued)

OTHER PUBLICATIONS

Applied Biosystems, Apr. 2008, SOLiD™ System Barcoding, Application Note, 4 pp.
Bogdanova et al., Jan. 2008, Normalization of full-length enriched cDNA, Molecular Biosystems, 4(3):205-212.
Brodin et al., 2015, Challenges with using primer IDs to improve accuracy of next generation sequencing, PLOS One, 19(3):1-12.
Clontech Laboratories, Inc., May 15, 2007, Super Smart™ PCR cDNA Synthesis Kit User Manual, 39 pp.
Marcus et al., 2006, Microfluidic single-cell mRNA isolation and analysis, Ana. Chem. 78:3084-3089.
Office Action dated Jun. 6, 2016 in Chinese patent application No. 201380022187.9.
Office Action dated Dec. 27, 2016 in Chinese patent application No. 201380022187.9.
(Continued)

*Primary Examiner* — Kevin S Orwig
(74) *Attorney, Agent, or Firm* — KNOBBE, MARTENS, OLSON & BEAR, LLP

(57) ABSTRACT

In accordance with some embodiments herein, compositions and methods for accurate barcoding of nucleic acids are described. The compositions and methods can involve a plurality of unique oligonucleotide species comprising unique molecule barcodes. In some embodiments, the molecule barcodes can have a relatively low G content, and can exhibit reduced bias in amplification and analysis.

54 Claims, 14 Drawing Sheets

Specification includes a Sequence Listing.

(56) References Cited

U.S. PATENT DOCUMENTS 6,284,485 B1 9/2001 Boyle
6,309,822 B1 10/2001 Fodor et al.
6,309,823 B1 10/2001 Cronin et al.
6,326,148 B1 12/2001 Pauletti et al.
6,355,431 B1 3/2002 Chee et al.
6,355,432 B1 3/2002 Fodor et al.
6,372,813 B1 4/2002 Travis
6,395,491 B1 5/2002 Fodor et al.
6,406,848 B1 6/2002 Bridgham et al.
6,436,675 B1 8/2002 Welch et al.
6,440,667 B1 8/2002 Fodor et al.
6,440,706 B1 8/2002 Vogelstein et al.
6,451,536 B1 9/2002 Fodor et al.
6,458,530 B1 10/2002 Morris et al.
6,468,744 B1 10/2002 Cronin et al.
6,480,791 B1 11/2002 Strathmann
6,489,114 B2 12/2002 Laayoun et al.
6,492,121 B2 12/2002 Kurane et al.
6,512,105 B1 1/2003 Hogan et al.
6,514,699 B1 2/2003 O'neill et al.
6,544,739 B1 4/2003 Fodor et al.
6,551,784 B2 4/2003 Fodor et al.
6,576,424 B2 6/2003 Fodor et al.
6,600,996 B2 7/2003 Webster et al.
6,629,040 B1 9/2003 Goodlett et al.
6,653,077 B1 11/2003 Brenner
6,753,147 B2 6/2004 Vogelstein et al.
6,787,308 B2 9/2004 Balasubramanian et al.
6,849,404 B2 2/2005 Park et al.
6,852,488 B2 2/2005 Fodor et al.
6,858,412 B2 2/2005 Willis et al.
7,155,050 B1 12/2006 Sloge
7,393,665 B2 7/2008 Brenner
7,424,368 B2 9/2008 Huang et al.
7,473,767 B2 1/2009 Dimitrov
7,476,786 B2 1/2009 Chan et al.
7,537,897 B2 5/2009 Brenner et al.
7,544,473 B2 6/2009 Brenner
7,635,566 B2 12/2009 Brenner
7,822,555 B2 10/2010 Huang et al.
7,824,856 B2 11/2010 Monforte
7,824,889 B2 11/2010 Vogelstein et al.
7,915,015 B2 3/2011 Vogelstein et al.
7,985,546 B2 7/2011 Church et al.
8,148,068 B2 4/2012 Brenner
8,168,385 B2 5/2012 Brenner
8,241,850 B2 8/2012 Brenner
8,298,767 B2 10/2012 Brenner et al.
8,318,433 B2 11/2012 Brenner
8,445,205 B2 5/2013 Brenner
8,470,996 B2 6/2013 Brenner
8,476,018 B2 7/2013 Brenner
8,481,292 B2 7/2013 Casbon et al.
8,486,682 B2 7/2013 Loeffert
8,535,889 B2 9/2013 Larson et al.
8,563,274 B2 10/2013 Brenner et al.
8,603,749 B2 12/2013 Gillevet
8,679,756 B1 3/2014 Brenner et al.
8,685,678 B2 4/2014 Casbon et al.
8,715,967 B2 5/2014 Casbon et al.
8,722,368 B2 5/2014 Casbon et al.
8,728,766 B2 5/2014 Casbon et al.
8,741,606 B2 6/2014 Casbon et al.
8,835,358 B2 9/2014 Fodor et al.
8,841,071 B2 9/2014 Link
8,856,410 B2 10/2014 Park
9,150,852 B2 10/2015 Samuels et al.
9,228,229 B2 1/2016 Olson et al.
9,290,808 B2 3/2016 Fodor et al.
9,290,809 B2 3/2016 Fodor et al.
9,315,857 B2 4/2016 Fu et al.
9,567,645 B2 2/2017 Fan et al.
9,567,646 B2 2/2017 Fan et al.
9,582,877 B2 2/2017 Fu et al.
9,598,736 B2 3/2017 Fan et al.
9,637,799 B2 5/2017 Fan et al.
9,695,468 B2 7/2017 Hindson
9,708,659 B2 7/2017 Fodor et al.
9,787,810 B1 8/2017 Fodor et al.
9,727,810 B2 10/2017 Fodor et al.
9,816,137 B2 11/2017 Fodor et al.
9,845,502 B2 12/2017 Fodor et al.
9,905,005 B2 2/2018 Fu et al.
9,951,386 B2 4/2018 Hindson et al.
10,002,316 B2 6/2018 Fodor et al.
10,047,394 B2 8/2018 Fodor et al.
10,059,991 B2 8/2018 Fodor et al.
10,131,958 B1 11/2018 Fan et al.
10,151,003 B2 12/2018 Fan et al.
10,202,641 B2 2/2019 Shum et al.
10,202,646 B2 2/2019 Fodor et al.
10,208,356 B1 2/2019 Fan et al.
10,246,703 B2 4/2019 Church et al.
10,253,375 B1 4/2019 Fan et al.
10,338,066 B2 7/2019 Fan
10,669,570 B2 6/2020 Chang
10,676,779 B2 6/2020 Chang
10,822,643 B2 11/2020 Shum et al.
11,124,823 B2 9/2021 Fu et al.
11,371,076 B2 6/2022 Lazaruk
2002/0065609 A1 5/2002 Ashby
2002/0072058 A1 6/2002 Voelker et al.
2002/0168665 A1 11/2002 Okawa
2002/0187480 A1 12/2002 Brandon
2003/0003490 A1 1/2003 Fan et al.
2003/0013091 A1 1/2003 Dimitrov
2003/0049616 A1 3/2003 Brenner et al.
2003/0082818 A1 5/2003 Bahnson et al.
2003/0104436 A1 6/2003 Morris et al.
2003/0165865 A1 9/2003 Hinkel
2003/0175908 A1 9/2003 Linnarsson
2003/0186251 A1 10/2003 Dunn et al.
2003/0207300 A1 11/2003 Matray et al.
2004/0047769 A1 3/2004 Tanaami
2004/0096368 A1 5/2004 Davis
2004/0096892 A1 5/2004 Wang et al.
2004/0121342 A1 6/2004 McKeown
2004/0146901 A1 7/2004 Morris et al.
2004/0157243 A1 8/2004 Huang et al.
2004/0191823 A1 9/2004 Virgos
2004/0253593 A1 12/2004 Cai
2004/0259118 A1 12/2004 Macevicz
2005/0019776 A1 1/2005 Callow et al.
2005/0053952 A1 3/2005 Hong et al.
2005/0105077 A1 5/2005 Padmanabhan
2005/0170373 A1 8/2005 Monforte
2005/0250147 A1 11/2005 Macevicz
2005/0287548 A1 12/2005 Bao
2006/0002824 A1 1/2006 Chang et al.
2006/0024690 A1 2/2006 Kao
2006/0035258 A1 2/2006 Tadakamalla et al.
2006/0040297 A1 2/2006 Leamon et al.
2006/0041385 A1 2/2006 Bauer
2006/0073506 A1 4/2006 Christians et al.
2006/0211030 A1 9/2006 Brenner
2006/0223122 A1 10/2006 Fogo
2006/0223197 A1 10/2006 Vielsack
2006/0234234 A1 10/2006 Van Dongen
2006/0246453 A1 11/2006 Kato
2006/0263709 A1 11/2006 Matsumura et al.
2006/0263789 A1 11/2006 Kincaid
2006/0280352 A1 12/2006 Muschler
2006/0286570 A1 12/2006 Rowlen et al.
2007/0020640 A1 1/2007 Mccloskey et al.
2007/0259340 A1 1/2007 Schramm
2007/0031829 A1 2/2007 Yasuno et al.
2007/0042400 A1 2/2007 Choi et al.
2007/0042419 A1 2/2007 Barany et al.
2007/0065823 A1 3/2007 Dressman et al.
2007/0105090 A1 5/2007 Cassidy et al.
2007/0117121 A1 5/2007 Hutchison
2007/0117134 A1 5/2007 Kou
2007/0133856 A1 6/2007 Dutta-Choudhury
2007/0172873 A1 7/2007 Brenner et al.

(56) References Cited

U.S. PATENT DOCUMENTS

2007/0178478 A1 8/2007 Dhallan et al.
2007/0202523 A1 8/2007 Becker
2008/0038727 A1 2/2008 Spier
2008/0070303 A1 3/2008 West et al.
2008/0119736 A1 5/2008 Dentinger
2008/0194414 A1 8/2008 Albert et al.
2008/0261204 A1 10/2008 Lexow
2008/0269068 A1 10/2008 Church et al.
2008/0274458 A1 11/2008 Latham et al.
2008/0299609 A1 12/2008 Kwon et al.
2008/0318802 A1 12/2008 Brenner
2009/0061513 A1 3/2009 Andersson et al.
2009/0105959 A1 4/2009 Braverman et al.
2009/0137407 A1 5/2009 Church et al.
2009/0220385 A1 9/2009 Brown
2009/0226891 A2 9/2009 Nova et al.
2009/0252414 A1 10/2009 Suzuki
2009/0253586 A1 10/2009 Nelson et al.
2009/0283676 A1 11/2009 Skoglund
2009/0290151 A1 11/2009 Agrawal
2009/0298709 A1 12/2009 Ma
2010/0069250 A1 3/2010 White, III
2010/0105049 A1 4/2010 Ehrich et al.
2010/0105886 A1 4/2010 Woudenberg et al.
2010/0120630 A1 5/2010 Huang et al.
2010/0159533 A1 6/2010 Lipson et al.
2010/0255471 A1 10/2010 Clarke
2010/0267028 A1 10/2010 Pasche
2010/0291666 A1 11/2010 Collier et al.
2010/0300895 A1 12/2010 Nobile et al.
2010/0323348 A1 12/2010 Hamady et al.
2010/0330574 A1 12/2010 Whitman
2011/0038507 A1 2/2011 Hager
2011/0059436 A1 3/2011 Hardin et al.
2011/0059556 A1 3/2011 Strey et al.
2011/0070584 A1 3/2011 Wohlgemuth et al.
2011/0072889 A1 3/2011 Albitar et al.
2011/0160078 A1 6/2011 Fodor et al.
2011/0201507 A1 8/2011 Rava et al.
2011/0230358 A1 9/2011 Rava
2011/0244455 A1 10/2011 Larson et al.
2011/0294689 A1 12/2011 Namsaraev
2012/0010091 A1 1/2012 Linnarson
2012/0014977 A1 1/2012 Furihata et al.
2012/0034607 A1 2/2012 Rothberg
2012/0040843 A1 2/2012 Ducree et al.
2012/0045844 A1 2/2012 Rothberg et al.
2012/0065081 A1 3/2012 Chee
2012/0071331 A1 3/2012 Casbon
2012/0087862 A1 4/2012 Hood
2012/0142018 A1 6/2012 Jiang et al.
2012/0149603 A1 6/2012 Cooney
2012/0156675 A1 6/2012 Lueerssen et al.
2012/0163681 A1 6/2012 Lohse
2012/0165219 A1 6/2012 Van Der Zaag et al.
2012/0173159 A1 7/2012 Davey et al.
2012/0190020 A1 7/2012 Oliphant et al.
2012/0220022 A1 8/2012 Ehrlich et al.
2012/0220494 A1 8/2012 Samuels
2012/0231972 A1 9/2012 Golyshin et al.
2012/0252012 A1 10/2012 Armougom et al.
2012/0253689 A1 10/2012 Rogan
2012/0316074 A1 12/2012 Saxonov
2012/0322681 A1 12/2012 Kung et al.
2013/0005585 A1 1/2013 Anderson et al.
2013/0022977 A1 1/2013 Lapidus et al.
2013/0035248 A1 2/2013 Icenhour
2013/0040344 A1 2/2013 Ju
2013/0040843 A1 2/2013 Von Toerne et al.
2013/0040847 A1 2/2013 Thrippleton
2013/0045994 A1 2/2013 Shinozuka et al.
2013/0190206 A1 7/2013 Leonard
2013/0210643 A1 8/2013 Casbon et al.
2013/0210659 A1 8/2013 Watson et al.
2013/0224743 A1 8/2013 Casbon et al.
2013/0225418 A1 8/2013 Watson
2013/0225623 A1 8/2013 Buxbaum et al.
2013/0237458 A1 9/2013 Casbon et al.
2013/0267424 A1 10/2013 Casbon et al.
2013/0274117 A1 10/2013 Church
2013/0295568 A1 11/2013 Link
2013/0323732 A1 12/2013 Anderson et al.
2014/0024032 A1 1/2014 Raj
2014/0057799 A1 2/2014 Johnson
2014/0065609 A1* 3/2014 Hicks ..... C12Q 1/6886
435/6.11
2014/0147860 A1 5/2014 Kaduchak
2014/0155274 A1 6/2014 Xie et al.
2014/0155295 A1 6/2014 Hindson et al.
2014/0178438 A1 6/2014 Sahin et al.
2014/0194324 A1 7/2014 Gormley
2014/0206079 A1 7/2014 Malinoski
2014/0206547 A1 7/2014 Wang
2014/0216128 A1 8/2014 Neat
2014/0227684 A1 8/2014 Hindson et al.
2014/0227705 A1 8/2014 Vogelstein et al.
2014/0228255 A1 8/2014 Hindson et al.
2014/0235506 A1 8/2014 Hindson et al.
2014/0243242 A1 8/2014 Nicol
2014/0272952 A1 9/2014 May et al.
2014/0274811 A1 9/2014 Arnold
2014/0287963 A1 9/2014 Hindson et al.
2014/0303005 A1 10/2014 Samuels et al.
2014/0309945 A1 10/2014 Park et al.
2014/0315211 A1 10/2014 Sugino et al.
2014/0357500 A1 12/2014 Vigneault et al.
2014/0378322 A1 12/2014 Hindson et al.
2014/0378345 A1 12/2014 Hindson et al.
2014/0378349 A1 12/2014 Hindson et al.
2014/0378350 A1 12/2014 Hindson et al.
2015/0005185 A1 1/2015 Fodor et al.
2015/0005199 A1 1/2015 Hindson et al.
2015/0005200 A1 1/2015 Hindson et al.
2015/0017652 A1 1/2015 Robins et al.
2015/0066385 A1 3/2015 Schnall-levin et al.
2015/0118680 A1 4/2015 Fodor et al.
2015/0119255 A1 4/2015 Fodor et al.
2015/0119256 A1 4/2015 Fodor et al.
2015/0119257 A1 4/2015 Fodor et al.
2015/0119258 A1 4/2015 Fodor et al.
2015/0119290 A1 4/2015 Fodor et al.
2015/0133319 A1 5/2015 Fu et al.
2015/0203897 A1* 7/2015 Robins ..... C12Q 1/6851
506/2
2015/0225778 A1 8/2015 Hindson et al.
2015/0247182 A1 9/2015 Faham et al.
2015/0259734 A1 9/2015 Asbury et al.
2015/0298091 A1 10/2015 Weitz
2015/0307874 A1 10/2015 Jaitin
2015/0329852 A1 11/2015 Nolan
2015/0376609 A1 12/2015 Hindson et al.
2016/0026758 A1 1/2016 Jabara et al.
2016/0122753 A1 5/2016 Mikkelsen
2016/0208322 A1 7/2016 Anderson et al.
2016/0222378 A1 8/2016 Fodor et al.
2016/0244828 A1 8/2016 Mason
2016/0257993 A1 9/2016 Fu et al.
2016/0289669 A1 10/2016 Fan et al.
2016/0289670 A1 10/2016 Samuels
2016/0289740 A1 10/2016 Fu et al.
2016/0312276 A1 10/2016 Fu et al.
2016/0320720 A1 11/2016 Fan et al.
2016/0326584 A1 11/2016 Fodor et al.
2016/0376583 A1 12/2016 Fodor et al.
2016/0376648 A1 12/2016 Fodor et al.
2017/0073730 A1 3/2017 Betts et al.
2017/0154421 A1 6/2017 Fu et al.
2017/0342405 A1 11/2017 Fu et al.
2017/0342465 A1 11/2017 Shum et al.
2017/0344866 A1 11/2017 Fan et al.
2018/0002738 A1 1/2018 Wang et al.
2018/0002764 A1 1/2018 Fan et al.
2018/0037942 A1 2/2018 Fu et al.
2018/0088112 A1 3/2018 Fan

(56) References Cited

U.S. PATENT DOCUMENTS

| | | | |
|---|---|---|---|
| 2018/0251825 | A1 | 9/2018 | Stoeckius |
| 2018/0258500 | A1 | 9/2018 | Fan et al. |
| 2018/0291470 | A1 | 10/2018 | Fan et al. |
| 2018/0327835 | A1 | 11/2018 | Fodor et al. |
| 2019/0100798 | A1 | 4/2019 | Fodor et al. |
| 2019/0119726 | A1 | 4/2019 | Shum et al. |
| 2019/0323088 | A1 | 10/2019 | Boutet |
| 2020/0002766 | A1 | 1/2020 | Genolet |
| 2020/0248175 | A1 | 8/2020 | van Galen et al. |
| 2020/0255888 | A1 | 8/2020 | Jensen |
| 2020/0392479 | A1 | 12/2020 | Blainey et al. |
| 2022/0062394 | A1 | 3/2022 | Ouspenskaia et al. |
| 2022/0315988 | A1 | 10/2022 | Lazaruk |

FOREIGN PATENT DOCUMENTS

| | | |
|---|---|---|
| EP | 1 473 080 | 11/2004 |
| EP | 1 647 600 | 4/2006 |
| EP | 1 845 160 | 10/2007 |
| EP | 2 623 613 | 8/2013 |
| EP | 2 805 769 | 11/2014 |
| JP | 2005-233974 | 9/2005 |
| JP | 2008-256428 | 10/2008 |
| JP | 2013-039275 | 2/2013 |
| WO | WO 89/01050 | 2/1989 |
| WO | WO 96/24061 | 8/1996 |
| WO | WO 97/10365 | 3/1997 |
| WO | WO 99/15702 | 4/1999 |
| WO | WO 99/28505 | 6/1999 |
| WO | WO 00/58516 | 10/2000 |
| WO | WO 02/056014 | 7/2002 |
| WO | WO 02/059355 | 8/2002 |
| WO | WO 02/070684 | 9/2002 |
| WO | WO 04/017374 | 2/2004 |
| WO | WO 05/042759 | 5/2005 |
| WO | WO 05/071110 | 8/2005 |
| WO | WO 05/080604 | 9/2005 |
| WO | WO 05/111242 | 11/2005 |
| WO | WO 06/071776 | 7/2006 |
| WO | WO 06/102264 | 9/2006 |
| WO | WO 06/116127 | 11/2006 |
| WO | WO 07/087310 | 8/2007 |
| WO | WO 07/087312 | 8/2007 |
| WO | WO 07/147079 | 12/2007 |
| WO | WO 08/096318 | 8/2008 |
| WO | WO 08/147428 | 12/2008 |
| WO | WO 08/150432 | 12/2008 |
| WO | WO 09/148560 | 12/2009 |
| WO | WO 09/152928 | 12/2009 |
| WO | WO 10/030818 | 3/2010 |
| WO | WO 10/117620 | 10/2010 |
| WO | WO 11/123246 | 10/2011 |
| WO | WO 11/143659 | 11/2011 |
| WO | WO 11/155833 | 12/2011 |
| WO | WO 12/038839 | 3/2012 |
| WO | WO 12/042374 | 4/2012 |
| WO | WO 12/047297 | 4/2012 |
| WO | WO 12/048341 | 4/2012 |
| WO | WO 12/083225 | 6/2012 |
| WO | WO 12/108864 | 8/2012 |
| WO | WO 12/129363 | 9/2012 |
| WO | WO 12/140224 | 10/2012 |
| WO | WO 12/142213 | 10/2012 |
| WO | WO 12/148477 | 11/2012 |
| WO | WO 12/149042 | 11/2012 |
| WO | WO 12/162267 | 11/2012 |
| WO | WO 13/019075 | 2/2013 |
| WO | WO 13/117595 | 8/2013 |
| WO | WO 13/130674 | 9/2013 |
| WO | WO 13/148525 | 10/2013 |
| WO | WO 13/173394 | 11/2013 |
| WO | WO 13/176767 | 11/2013 |
| WO | WO 13/177206 | 11/2013 |
| WO | WO 13/188831 | 12/2013 |
| WO | WO 13/188872 | 12/2013 |
| WO | WO 13/191775 | 12/2013 |
| WO | WO 14/015084 | 1/2014 |
| WO | WO 14/015098 | 1/2014 |
| WO | WO 14/018460 | 1/2014 |
| WO | WO 14/028537 | 2/2014 |
| WO | WO 14/071361 | 5/2014 |
| WO | WO 14/093676 | 6/2014 |
| WO | WO 14/108850 | 7/2014 |
| WO | WO 14/124336 | 8/2014 |
| WO | WO 14/124338 | 8/2014 |
| WO | WO 14/126937 | 8/2014 |
| WO | WO 14/144495 | 9/2014 |
| WO | WO 14/145992 | 9/2014 |
| WO | WO 14/201273 | 12/2014 |
| WO | WO 14/210353 | 12/2014 |
| WO | WO 15/002908 | 1/2015 |
| WO | WO 15/031691 | 3/2015 |
| WO | WO 15/035087 | 3/2015 |
| WO | WO 15/044428 | 4/2015 |
| WO | WO 15/047186 | 4/2015 |
| WO | WO 15/103339 | 7/2015 |
| WO | WO 15/134787 | 9/2015 |
| WO | WO 15/200869 | 12/2015 |
| WO | WO 16/138500 | 9/2016 |
| WO | WO 17/205691 | 11/2017 |
| WO | WO 18/089377 | 5/2018 |
| WO | WO 18/094263 | 5/2018 |

OTHER PUBLICATIONS

Office Action dated Jul. 14, 2017 in Chinese patent application No. 201380022187.9.

Search Report and Written Opinion mailed Mar. 1, 2016 in Singapore patent application No. 11201405274W.

Office Action dated Sep. 8, 2017 in U.S. Appl. No. 15/134,967.

Third-Party Pre-Issuance Submission filed on Jun. 15, 2018 for U.S. Appl. No. 15/847,752.

Third-Party Pre-Issuance Submission filed on Jun. 11, 2018 for U.S. Appl. No. 15/847,752.

Begley Jun. 20, 2017, Psst, the human genome was never completely sequenced. STAT News, 7 pp.

Bose et al., Jun. 6, 2015, Scalable microfluidics for single-cell RNA printing and sequencing, Genome Biology, 16(1):120.

Brinza et al., Apr. 16-20, 2016, Detection of somatic mutations at 0.1% frequency from cfDNA in peripheral blood with a multiplex next-generation sequencing assay, conference poster, AACR 107th Annual Meeting, 1 p.

Caruccio et al., Oct. 2009, Nextera™ technology for NGS DNA library preparation: simultaneous fragmentation and tagging by in vitro transposition, 16(3), 3 pp.

Di Carlo et al., Dec. 1, 2008, Dynamic single-cell analysis for quantitative biology, Analytical Chemistry, 78(23):7918-7925.

Evanko, 2004, Hybridization chain reactions Nature Methods, 1:186.

Fu et al., Feb. 4, 2014, Molecular indexing enables quantitative targeted RNA sequencing and reveals poor efficiencies in standard library preparations, PNAS, 111(5):1891-1896.

Gu et al., Apr. 16-20, 2016, Complete workflow for detection of low frequency somatic mutations from cell-free DNA using Ion Torrent™ platforms, conference poster, AACR 107th Annual Meeting, 1 p.

Jiang et al., 2011, Synthetic spike-in standards for RNA-seq experiments, Genome Research, 21(9):1543-1551.

Lin et al., Feb. 2007, Self-assembled combinatoral encoding nanoarrays for multiplexed biosensing, Nano Letters, 7(2):507-512.

Loy et al., Oct. 2, 2018, A rapid library preparation method with custom assay designs for detection of variants at 0.1% allelic frequency in liquid biopsy samples, undated, 1 p.

Massachusetts General Hospital, Overview of Illumina Chemistry, http://nextgen.mgh.harvard.edu/IlluminaChemistry.html, downloaded Dec. 31, 2018, 2 pp.

Muller et al., Oct. 17, 2018, Genome organization and DNA accessibility control antigenic variation in trypanosomes, Nature, 563(7729):121-125.

(56) References Cited

OTHER PUBLICATIONS

Peters et al., Jan. 14, 2015, Co-barcoded sequence reads from long DNA fragments: a cost-effective solution for "perfect genome" sequencing, Frontiers in Genetics, 5(Article 466)1-8.
Poole et al., 2007, Measuring global gene expression in polyploidy; a cautionary note from allohexaploid wheat, Funct. Integr Genomics, 7:207-219.
Robinson et al., 2010, A scaling normalization method for differential expression analysis of RNA-seq data, Genome Biology, vol. 11, 9 pp.
Shortreed et al., Sep. 2, 2005, A thermodynamic approach to designing structure-free combinatorial DNA word sets, Nucleic Acids Research, 33(15):4965-4977.
Siegel et al., Apr. 12, 2010, Genome-wide analysis of mRNA abundance in two life-cycle stages of trypanosoma brucei and identification of splicing and polyadenylation sites, Nucleic Acids Research, 38(15):4946-4957.
Sogin et al., 2006, Microbilal diversity in the deep sea and the underexplored "rare biosphere," PNAS, 103:12115-12120.
Solomatin et al., 2009, Methods of site-specific labling of NRA with fluorescent dyes, Methods in Enzymology, vol. 469, 22 pp.
Velten et al., 2015, Single-cell polyadenylation site mapping reveals 3' isoform choice variability, Molecular Systems Biology, 11(812):1-14.
Vollbrecht et al., 2018, Validation and comparison of two NGS assays for the detection of EGFR T790M resistance mutation in liquid biopsies of NSCLC patients, Oncotarget, 9(26):18529-18539.
Wang et al., Jan. 2012, A novel in situ RNA analysis platform for formalin-fixed, paraffin-embedded tissues, The Journal of Molecular Diagnostics, 14(1):22-29.
Zagordi et al., 2010, Error correction of next-generation sequencing data and reliable estimation of HIV quasispecies, Nucleic Acids Research, 38:7400-7409.
Zheng et al., Jan. 16, 2017, Massively parallel digital transcriptional profiling of single cells, Nature Communications, 8:14049.
Complaint filed in Becton, *Dickinson and Company and Cellular Research Inc.* v. *10X Genomics, Inc.* on Nov. 15, 2018.
First Amended Complaint filed in Becton, *Dickinson and Company and Cellular Research Inc.* v. *10X Genomics, Inc.* (C.A. No. 18-1800-RGA)) on Feb. 8, 2019.
Motion to Dismiss and Opening Brief in Support of the Motion to Dismiss filed in Becton, *Dickinson and Company and Cellular Research Inc.* v. *10X Genomics, Inc.* (C.A. No. 18-1800-RGA)) on Jan. 18, 2019.
Plaintiff's Opposition to Defendant 10X Genomics's Motion to Dismiss Pursuant to Federal Rule of Civil Procedure 12(b)(6), filed Feb. 15, 2019 in USDC District of Delaware, C.A. No. 18-1800 (RGA), 3 pp.
Defendant 10X Genomics's Opening Brief in Support of Its Motion to Dismiss Pursuant to Federal Rule of Civil Procedure 12(b)(6), dated Mar. 1, 2019 in USDC District of Delaware, C.A. No. 18-1800 RGA, 101 pp.
Plaintiff's Brief in Opposition to Defendant's Motion to Dismiss Pursuant to Fed. R. Civ. P. 12(b)(6), filed Mar. 29, 2019 in USDC District of Delaware, C.A. No. 18-1800 (RGA), 27 pp.
Defendant 10X Genomics's Reply Brief in Support of Its Motion to Dismiss Pursuant to Federal Rule of Civil Procedure 12(b)(6), dated Apr. 12, 2019 in USDC District of Delaware, C.A. No. 18-1800 RGA, 15 pp.
Decision in Inter Partes Review Case IRP2019-00565, entered Jul. 22, 2019, 30 pp.
Decision in Inter Partes Review Case IRP2019-00566, entered Jul. 22, 2019, 13 pp.
Office Action dated Mar. 19, 2019 in U.S. Appl. No. 15/046,225.
Examination report dated Sep. 5, 2018 in European patent application No. 16710357.1.
Examination report dated Apr. 26, 2019 in European patent application No. 16710357.1.
Office action dated Jul. 20, 2018 in U.S. Appl. No. 15/217,886.
Office Action dated Nov. 5, 2018 in U.S. Appl. No. 16/038,790.
Office Action dated Jan. 14, 2019 in U.S. Appl. No. 16/219,553.
Office Action dated Dec. 13, 2018 in Canadian patent application No. 2,865,575.
Notice of Reasons for Rejection dated Dec. 5, 2018 in Japanese patent application No. 2017-245295.
Examination Report dated Mar. 18, 2019 in Singapore patent application No. 1120140274W.
Office Action dated May 23, 2019 in U.S. Appl. No. 15/459,977.
Office action dated Oct. 25, 2018 in U.S. Appl. No. 16/012,584.
Office action dated Mar. 1, 2019 in U.S. Appl. No. 16/012,584.
First Action Interview Pilot Program Pre-Interview Communication dated Oct. 15, 2018 in U.S. Appl. No. 15/987,851.
First Action Interview Office Action Summary dated Jan. 25, 2019 in U.S. Appl. No. 15/987,851.
Office Action dated Apr. 22, 2019 in U.S. Appl. No. 15/987,851.
Examination Report No. 1 for standard patent application, dated Jul. 20, 2018 Australian patent application No. 2014312208.
First Office Action dated Jan. 2, 2019 in Chinese patent application No. 201480059505.3.
Extended European Search Report dated Mar. 22, 2019 in patent application No. 18195513.9.
Third Party Observation dated Jun. 14, 2018 in Japanese patent application No. 2016-537867.
Official Action dated Jul. 30, 2018 in Japanese patent application No. 2016-537867.
Second Office Action dated Sep. 7, 2018 in Chinese patent application No. 201480061859.1.
Notice of Reasons for Rejection dated Aug. 31, 2018 in Japanese patent application No. 2016-520632.
Office Action dated Jul. 25, 2018 in U.S. Appl. No. 15/108,268.
Office Action dated Jul. 5, 2018 in U.S. Appl. No. 15/004,618.
Extended European Search Report dated Jun. 11, 2018 in European patent application No. 16740872.3.
Examination report dated Sep. 26, 2018 in European patent application No. 16714081.3.
Office Action dated Jan. 7, 2019 in U.S. Appl. No. 15/055,407.
Office Action dated May 1, 2020 in U.S. Appl. No. 15/557,789.
Office Action dated Oct. 22, 2020 in U.S. Appl. No. 15/557,789.
Office Action dated Jul. 20, 2021 in U.S. Appl. No. 15/557,789.
Office Action dated Jan. 4, 2022 in U.S. Appl. No. 15/557,789.
Examination Report dated Jan. 2, 2019 in European examination report No. 16757986.1.
Office Action dated May 15, 2019 in U.S. Appl. No. 15/084,307.
Office Action dated Nov. 16, 2018 in U.S. Appl. No. 15/134,967.
Examination Report dated Dec. 12, 2018 in European patent application No. 16719706.0.
Office Action dated Jan. 7, 2020 in U.S. Appl. No. 15/574,122.
Office Action dated Jul. 14, 2020 in U.S. Appl. No. 15/574,122.
Office Action dated Nov. 24, 2020 in U.S. Appl. No. 15/574,122.
Examination report No. 1 dated Sep. 5, 2022 in Australian patent application No. 2017261189.
Examination Report dated Oct. 26, 2020 in European patent application No. 17735675.5.
Decision of Rejection dated Mar. 2, 2022 in Japanese patent application No. 2018-0557413.
International Search Report and Written Opinion dated May 28, 2020 in PCT/US2020/017749.
Office action dated Aug. 5, 2022 in U.S. Appl. No. 16/788,221.
International Search Report and Written Opinion dated Jun. 25, 2020 in PCT/US2020/013685.
Office Action dated Sep. 23, 2021 in U.S. Appl. No. 16/743,898.
Bengtsson et al., 2006, Microarray image analysis: background estimation using quantile and morphological filters, BMC Bioinformatics, 7:96.
Katzer et al., Dec. 2003, Methods for automatic microarray image segmentation, IEEE Transactions on Nanobioscience, 2(4):202-214.
Examination report dated Jun. 13, 2023 in European patent application No. 14786757.6.
Office Action dated Jan. 6, 2021 in U.S. Appl. No. 15/574,122.
Examination report No. 1 dated Nov. 8, 2024 in Australian patent application No. 2023202747.
Examination report dated Aug. 5, 2024 in Canadian patent application No. 3,019,589.

(56) References Cited

OTHER PUBLICATIONS

Extended European search report dated Jan. 15, 2024 in patent application No. 23181147.2.
Notice of reasons for refusal dated Sep. 14, 2023 in Japanese patent application No. 2022-106377.
Decision of refusal dated Apr. 22, 2024 in Japanese patent application No. 2022-106377.
Office Action dated Dec. 27, 2024 in U.S. Appl. No. 17/830,897.
"SOLiD™ System Barcoding", Applied Biosystems (ABI) Application Note, (Apr. 2008), pp. 1-4.
"Super Smart™ PCR cDNA Synthesis Kit User Manual", Clontech Laboratories, Inc., (2007) pp. 1-39.
Algae, Wikipedia.org, accessed Mar. 4, 2016, 20 pp.
Archaea, Wikipedia.org, accessed May 11, 2016, 26 pp.
Bontoux et al, "Integrating whole transcriptome assays on a lab-on-a-chip for single cell gene profiling", Lab on a Chip, (2008) vol. 8, No. 3, pp. 443-450.
Brady et al., "Construction of cDNA libraries form single cells", Methods in Enzymology, Academic Press, US, (1993) vol. 225, doi:10.1016/0076-6879(93)25039-5, ISSN 0076-6879, pp. 611-623.
Buschmann et al., Aug. 7, 2014, Enhancing the detection of barcoded reads in high throughput DNA sequencing DNA by controlling the false discovery rate, BMC Bioinformatics, 15(1):264.
Cloonan et al., "Stem cell transcriptome profiling via massive-scale mRNA sequencing", Nature Methods, (Jul. 2008) vol. 5, No. 7, pp. 613-619.
Costa et al., Aug. 22, 2012, Single-tube nested real-time PCR as a new highly sensitive approach to trace hazelnut, J. Agric Food Chem, 60(33):8103-8110.
Custom Antibody Services, Precision Antibody, accessed Apr. 16, 2014, 2 pp.
Eberwine et al., "Analysis of gene expression in single live neurons", Proc. Natl. Acad. Sci. USA, (Apr. 1992) vol. 89, No. 7, pp. 3010-3014.
Fish, Wikipedia.org, accessed Nov. 2, 2014, 11 pp.
Fungus, Wikipedia.org, accessed Jun. 3, 2013, 28 pp.
Harbers, "The current status of cDNA cloning", Genomics, (2008) vol. 91, No. 3, pp. 232-242.
Hartmann, "Gene expression profiling of single cells on large-scale oligonucleotide arrays", Nucleic Acids Research, (Oct. 2006) vol. 34, No. 21, p. e143.
How many species of bacteria are there? Wisegeek.org, accessed Jan. 21, 2014, 2 pp.
Islam et al, "Highly multiplexed and strand specific single-cell RNA 5' end sequencing", Nature Protocols, (2012) vol. 7, No. 5, pp. 813-828.
Karrer et al., "In situ isolation of mRNA from individual plant cells: creation of cell-specific cDNA libraries.", Proc. Natl. Acad. Sci. USA, (Apr. 1995) vol. 92, No. 9, pp. 3814-3818.
Ko et al., "RNA-conjugated template-switching RT-PCR method for generating an *Escherichia coli* cDNA library for small RNAs", Journal of Microbiological Methods, (2006) vol. 64, No. 3, pp. 297-304.
Kurimoto et al, "Global single-cell cDNA amplification to provide a template for representative high-density oligonucleotide microarray analysis", Nature Protocols, (2007) vol. 2, No. 3, pp. 739-752.
List of sequenced bacterial genomes, Wikipedia.org, accessed Jan. 24, 2014, 57 pp.
Maeda et al., "Development of a DNA barcode tagging method for monitoring dynamic changes in gene expression by using an ultra high-throughput sequencer", BioTechniques, (Jul. 2008), vol. 45, No. 1, pp. 95-97.
Mammal, Wikipedia.org, accessed Sep. 22, 2011, 16 pp.
Mardis, "Next-generation DNA sequencing methods", Annu. Rev. Genomics Hum. Genet., (2008) vol. 9, pp. 387-402.
Marguerat et al, "Next-generation sequencing: applications beyond genomes", Biochemical Society Transactions, (2008) vol. 36, No. 5, pp. 1091-1096.
Meyer et al., "Parallel tagged sequencing on the 454 platform", Nature Protocols, (2008) vol. 3, No. 2, pp. 267-278.
Murinae, Wikipedia.org, accessed Mar. 18, 2013, 21 pp.
Ozkumur et al., Apr. 3, 2013, Inertial focusing for tumor antigen-dependent and -independent sorting of rare circulating tumor cells, Sci Transl Med, 5(179):1-20.
Plant, Wikipedia.org, accessed Aug. 28, 2015, 14 pp.
Protozoa, Wikipedia.org, accessed May 11, 2016, 10 pp.
Shendure et al., "Next-generation DNA sequencing", Nature Biotechnology, (Oct. 2008) vol. 26, No. 10, pp. 1135-1145.
Sommer et al., Nov. 16, 1989, Minimal homology requirements for PCR primers, Nucleic Acids Research, 17(16):6749.
Song et al., 2013, Design rules for size-based cell sorting and sheathless cell focusing by hydrophoresis, Journal of Chromatography A, 1302:191-196.
Subkhankulova et al., "Comparative evaluation of linear and exponential amplification techniques for expression profiling at the single cell level", Genome Biology, (Mar. 2006) vol. 7, No. R18, pp. 1-16.
Tang et al, "RNA-Seq analysis to capture the transcriptome landscape of a single cell", Nature Protocols, (2010) vol. 5, No, 3, pp. 516-535.
Virus, Wikipedia.org, accessed Nov. 24, 2012, 34 pp.
Zhu et al., "Reverse transcriptase template switching: a SMART approach for full-length cDNA library construction.", BioTechniques, (Apr. 2001) vol. 30, No. 4, pp. 892-897.
Office Action dated Sep. 8, 2017 in U.S. Appl. No. 15/046,225.
Office Action dated May 3, 2018 in U.S. Appl. No. 15/046,225.
Office action dated Jan. 9, 2018 in U.S. Appl. No. 15/217,896.
Office action dated Jan. 12, 2018 in U.S. Appl. No. 15/217,886.
Office Action dated Nov. 16, 2017 in U.S. Appl. No. 14/381,488.
Office Action dated May 10, 2018 in U.S. Appl. No. 14/381,488.
Examination Report No. 1 for standard patent application, dated Oct. 24, 2017, Australian patent application No. 2013226081.
Office Action dated Feb. 15, 2018 in Canadian patent application No. 2,865,575.
Extended European Search Report dated Feb. 8, 2018 in patent application No. 17202409.3.
Final Decision dated Aug. 30, 2017 in Japanese patent application No. 2014-558975.
Notice of Reasons for Rejection dated Apr. 2, 2018 in Japanese patent application No. 2014-558975.
Examination Report dated Mar. 16, 2018 in European patent application No. 13754428.4.
Examination Report dated Oct. 10, 2017 in European patent application No. 14761937.3.
Examination Report dated Jan. 3, 2018 in GB patent application No. 1609740.4.
Office Action dated Oct. 16, 2017 in U.S. Appl. No. 15/409,355.
First Office Action dated Dec. 19, 2017 in Chinese patent application No. 201480061859.1.
Office Action dated Nov. 9, 2017 in U.S. Appl. No. 15/004,618.
Office Action dated Nov. 1, 2017 in U.S. Appl. No. 15/667,125.
Office Action dated Sep. 6, 2017 in U.S. Appl. No. 15/134,967.
Office Action dated Mar. 8, 2018 in U.S. Appl. No. 15/608,780.
International Search Report and Written Opinion dated Sep. 8, 2017 in PCT/US2017/030097.
Statement of Opposition of Strawman Limited filed against European Patent No. EP2414548B1 on Jul. 19, 2016.
Statement of Opposition filed against European Patent No. EP2414548B1 on Jul. 26, 2016.
Statement of Opposition filed against European Patent No. EP2414548B1 on Jul. 21, 2016.
Submission dated Jan. 15, 2018 by Strawman Limited in preparation for upcoming oral proceedings in opposition against European Patent No. EP2414548B1.
Submission dated Jan. 15, 2018 by Vossius & Partner in preparation for upcoming oral proceedings in opposition against European Patent No. EP2414548B1.
Third-Party Pre-Issuance Submission filed on Jun. 16, 2018 for U.S. Appl. No. 15/847,752.
Third-Party Pre-Issuance Submission filed on Jun. 6, 2018 for U.S. Appl. No. 15/847,752.

(56) References Cited

OTHER PUBLICATIONS

Third-Party Pre-Issuance Submission filed on May 21, 2018 for U.S. Appl. No. 15/847,752.
Achim et al., May 2015, High-throughput spatial mapping of single-cell RNA-seq data to tissue of origin. Nature Biotechnology, 33(5):503-511.
Alkan et al., Oct. 2009, Personalized copy number and segmental duplication maps using next-generation sequencing. Nat Genet., 41(10):1061-1067.
Anderson, Feb. 11, 2014, Study describes RNA sequencing applications for molecular indexing methods, genomeweb.com, 5 pages.
Ansorge, 2009, Next-generation DNA sequencing techniques. New Biotechnology, 25(4):195-203.
Atanur et al., Jun. 2010, The genome sequence of the spontaneously hypertensive rat: Analysis and functional significance. Genome Res., 20(6):791-803.
Audic et al., 1997, The Significance of Digital Gene Expression Profiles. Genome Research, 7:986-995.
Bendall et al., May 6, 2011, Single-cell mass cytometry of differential immune and drug responses across a human hematopoietic continuum. Science, 332(6030):687-696.
Bionumbers, Aug. 21, 2010, Useful fundamental numbers in molecular biology, http://bionumbers.hms.harvard.edu/KeyNumbers/aspx, 4 pages.
Bioscribe, Feb. 5, 2015, Massively parallel sequencing technology for single-cell gene expression published (press release), 3 pp.
Blainey, May 2013, The future is now: single-cell genomics of bacteria and archaea, FEMS Microbiol Rev., 37(3):407-427.
Bonaldo et al., Sep. 1996, Normalization and subtraction: two approaches to facilitate gene discovery. Genome Res., 6(9):791-806.
Braha et al., 2000, Simultaneous stochastic sensing of divalent metal ions. Nature Biotechnology, 18:1005-1007.
Bratke et al., Sep. 2005, Differential expression of human granzymes A, B, and K in natural killer cells and during CD8+ T cell differentiation in peripheral blood. Eur J Immunol., 35(9):2608-2616.
Brenner et al., 2000, Gene expression analysis by massively parallel signature sequencing (MPSS) on microbead arrays. Nature Biotechnology, 18:630-634.
Brenner et al., Feb. 15, 2000, In vitro cloning of complex mixtures of DNA on microbeads: physical separation of differentially expressed cDNAs. Proc Natl Acad Sci, 97(4):1665-1670.
Brisco et al., Jun. 25, 2012, Quantification of RNA integrity and its use for measurement of transcript number, Nucleic Acids Research, 40(18):e144.
Butkus, Feb. 6, 2014, Cellular research set to launch first gene expression platform using 'molecular indexing' technology, genomeweb.com, 5 pages.
Cai, Mar. 2013, Turning single cells in microarrays by super-resolution bar-coding, Brief Funct Genomics, 12(2):75-80.
Carr et al., Dec. 15, 2009, Inferring relative proportions of DNA variants from sequencing electropherograms. Bioinformatics, 25(24):3244-3250.
Casbon et al., Jul. 2011, A method for counting PCR template molecules with application to next-generation sequencing. Nucleic Acids Res., 39(12):e81.
Castellarnau et al., Jan. 2015, Stochastic particle barcoding for single-cell tracking and multiparametric analysis, Small, 11(4):489-498.
Castle et al., Apr. 16, 2010, DNA copy number, including telomeres and mitochondria, assayed using next-generation sequencing. BMC Genomics, 11:244. doi: 10.1186/1471-2164-11-244.
Chamberlain et al., Dec. 9, 1988, Deletion screening of the Duchenne muscular dystrophy locus via multiplex DNA amplification. Nucleic Acids Res., 16(23):11141-11156.
Chang et al., Aug. 2002, Detection of allelic imbalance in ascitic supernatant by digital single nucleotide polymorphism analysis. Clin Cancer Res., 8(8):2580-2585.
Chee et al., 1996, Accessing genetic information with high-density DNA arrays, Science, 274:610-614.
Chee, 1991, Enzymatic multiplex DNA sequencing. Nucleic Acids Research, 19(12): 3301-3305.
Chen et al., Apr. 9, 2015, Spatially resolved, highly multiplexed RNA profiling in single cells. Science Express, pp. 1-21.
Church et al., 1988, Multiplex DNA sequencing. Science, 240:185-188.
Costello et al., Apr. 1, 2013, Discovery and characterization of artefactual mutations in deep coverage targeted capture sequencing data due to oxidative DNA damage during sample preparation. Nucleic Acids Res, 41(6):e67.
Cox. May 2001, Bar coding objects with DNA. Analyst, 126(5):545-547.
Craig et al., Oct. 2008, Identification of genetic variants using bar-coded multiplexed sequencing. Nat Methods, 5(10):887-893.
Cusanovich et al., May 7, 2014, Multiplex single-cell profiling of chromatin accessibility by combinatorial cellular indexing. Science Express, pp. 1-9.
Daines et al., Aug. 2009, High-throughput multiplex sequencing to discover copy number variants in *Drosophila*. Genetics, 182(4):935-941.
Dalerba et al., 2011, Single-cell dissection of transcriptional heterogeneity in human colon tumors, Nat Biotechnol., 29(12):1120-1127 and Supplementary Material.
D'Antoni et al., May 1, 2006, Rapid quantitative analysis using a single molecule counting approach. Anal Biochem. 352(1):97-109.
Daser et al., 2006, Interrogation of genomes by molecular copy-number counting (MCC). Nature Methods, 3(6):447-453.
De Saizieu et al., 1998, Bacterial transcript imaging by hybridization of total RNA to oligonucleotide arrays. Nature Biotechnology, 16:45-48.
Dirks et al., Oct. 26, 2004, Triggered amplification by hybridization chain reaction., Proc Natl Acad Sci U S A, 101(43), 15275-15278.
Fan et al., Feb. 6, 2015, Combinatorial labeling of single cells for gene expression cytometry. Science, 347(6222):1258367-8.
Fan et al., 2000, Parallel Genotyping of Human SNPs Using Generic High-density Oligonucleotide Tag Arrays. Genome Research, 10:853-860.
Fan et al., 2009, Microfluidic digital PCR enables rapid prenatal diagnosis of fetal aneuploidy. Am Obstet Gynecol. 200:543.e1-543.e7.
Fan et al., Jul. 19, 2012, Non-invasive prenatal measurement of the fetal genome. Nature, 487(7407):320-324.
Fan, Nov. 2010, Molecular counting: from noninvasive prenatal diagnostics to whole-genome haplotyping, doctoral dissertation, Stanford University, 185 pp.
Feldhaus et al., Jan. 15, 2000, Oligonucleotide-conjugated beads for transdominant genetic experiments, Nucleic Acids Res., 28(2):534-543.
Fox-Walsh et al., Oct. 2011, A multiplex RNA-seq strategy to profile poly(A+) RNA: application to analysis of transcription response and 3' end formation., Genomics, 98(4),266-271.
Fu et al., Mar. 18, 2014, Digital encoding of cellular mRNAs enabling precise and absolute gene expression measurement by single-molecule counting. Anal Chem., 86(6):2867-2870.
Fu et al., May 31, 2011, Counting individual DNA molecules by the stochastic attachment of diverse labels. Proc Natl Acad Sci, 108(22):9026-9031.
Gerry et al., 1999, Universal DNA microarray method for multiplex detection of low abundance point mutations. Journal of Molecular Biology, 292(2): 251-262.
Gillespie, 1977, Exact stochastic simulation of coupled chemical reactions. The Journal of Physical Chemistry, 81(25):2340-2361.
Gong et al., 2010, Massively parallel detection of gene expression in single cells using subnanolitre wells, Lab Chip, 10:2334-2337.
Grant et al., Nov. 15, 2002, SNP genotyping on a genome-wide amplified DOP-PCR template. Nucleic Acids Res, 30(22):e125.
Gunderson et al., May 2004, Decoding randomly ordered DNA arrays. Genome Res. 14(5):870-877.
Gundry et al., Jan. 3, 2012, Direct mutation analysis by high-throughput sequencing: from germline to low-abundant, somatic variants. Mutat Res. 729(1-2):1-15.

(56) References Cited

OTHER PUBLICATIONS

Gundry et al., Mar. 2012, Direct, genome-wide assessment of DNA mutations in single cells. Nucleic Acids Res., 40(5):2032-40.
Hacia et al., 1999, Determination of ancestral alleles for human single-nucleotide polymorphisms using high-density oligonucleotide arrays. Nature Genetics, 22:164-167.
Haff, 1994, Improved quantitative PCR using nested primers, PCR Methods and Applications, 3:332-337.
Hamady et al., Mar. 2008, Error-correcting barcoded primers for pyrosequencing hundreds of samples in multiplex. Nat Methods, 5(3):235-237.
Harrington et al., 2009, Cross-sectional characterization of HIV-1 env compartmentalization in cerebrospinal fluid over the full disease course, AIDS, 23(8) 907-915.
Hashimshony et al., Sep. 27, 2012, CEL-Seq: single-cell RNA-Seq by multiplexed linear amplification Cell Rep. 2(3):666-673.
Hensel et al., Jul. 21, 1995, Simultaneous identification of bacterial virulence genes by negative selection. Science. 269(5222):400-403.
Hiatt et al., Feb. 2010, Parallel, tag-directed assembly of locally derived short sequence reads. Nat Methods, 7(2):119-122.
Hiatt et al., May 2013, Single molecule molecular inversion probes for targeted, high-accuracy detection of low-frequency variation. Genome Res., 23(5):843-854.
Hollas et al., 2003, A stochastic approach to count RNA molecules using DNA sequencing methods. Lecture Notes in Computer Science, 2812:55-62.
Hug et al., 2003, Measure of the number of molecular of a single mRNA species in a complex mRNA preparation, Journal of Theoretical Biology, 221:615-624.
Ingolia et al., Apr. 10, 2009, Genome-wide analysis in vivo of translation with nucleotide resolution using ribosome profiling. Science, 324(5924):218-223.
Islam et al., 2011, Characterization of the single-cell transcriptional landscape by highly multiplex RNA-seq. Genome Research, 21:1160-1167.
Islam et al., 2014, Quantitative single-cell RNA-seq with unique molecular identifiers, Nature Methods, 11(2):163-168.
Jabara et al., Dec. 3, 2011, Accurate sampling and deep sequencing of the HIV-1 protease gene using a Primer ID, PNAS, 108(50):20166-20171.
Jabara, Apr. 23, 2010, Capturing the cloud: High throughput sequencing of multiple individual genomes from a retroviral population. Biology Lunch Bunch Series, Training Initiatives in Biomedical & Biological Sciences of the University of North Carolina at Chapel Hill.
Junker et al., May 21, 2015, Single-cell transcriptomics enters the age of mass production, Molecular Cell, 58:563-564.
Kanagawa, 2003, Bias and artifacts in multitemplate polymerase chain reactions (PCR), Journal of Bioscience and Bioengineering, 96(4):317-323.
Kebschull et al., Jul. 17, 2015, Sources of PCR-induced distortions in high-throughput sequencing data sets, Nucleic Acids Research, 15 pp.
Keys et al., Jun. 2015, Primer ID informs next-generation sequencing platforms and reveals preexisting drug resistance mutations in the HIV-1 reverse transcriptase coding domain, AIDS Research and Human Retroviruses, 31(6):658-668.
Kim et al., Jun. 8, 2007, Polony multiplex analysis of gene expression (PMAGE) in mouse hypertrophic cardiomyopathy, Science, 316(5830):1481-1484.
Kinde et al., Jun. 7, 2011, Detection and quantification of rare mutations with massively parallel sequencing, Proc. Natl Acad Sci, 108(23):9530-0535.
Kivioja et al., Jan. 2012, Counting absolute numbers of molecules using unique molecular identifiers. Nature Methods, 9(1):72-76.
Klein et al., May 21, 2015, Droplet barcoding for single-cell transcriptomics applied to embryonic stem cells, Cell, 161:1187-1201.
Koboldt et al., Sep. 1, 2009, VarScan: variant detection in massively parallel sequencing of individual and pooled samples. Bioinformatics. 25(17):2283-2285.
Kolodziejczyk et al., May 21, 2015, The technology and biology of single-cell RNA sequencing, Molecular Cell, 58:610-620.
Konig et al., Jul. 2010, iCLIP reveals the function of hnRNAP particles in splicing at individual nucleotide resolution, Nature Structural & Molecular Biology, 17(7):909-916.
Kotake et al., 1996, A simple nested RT-PCR method for quantitation of the relative amounts of multiple cytokine mRNAs in small tissue samples, Journal of Immunological Methods, 199:193-203.
Kurimoto et al., Mar. 17, 2006, An improved single-cell cDNA amplification method for efficient high-density oligonucleotide microarray analysis, Nucleic Acids Res., 34(5):e42.
Lamble et al., Nov. 20, 2013, Improved workflows for high throughput library preparation using the transposome-based nextera system, BMC Biotechnology, 13(1):104.
Larson et al., Nov. 2009, A single molecule view of gene expression. Trends Cell Biol. 19(11):630-637.
Leamon et al., Nov. 2003, A massively parallel PicoTiterPlate based platform for discrete picoliter-scale polymerase chain reactions, Electrophoresis, 24(21):3769-3777.
Lee et al., 2010, Large-scale arrays of picolitre chambers for single-cell analysis of large cell populations, Lab Chip, 10:2952-2958.
Lee et al., Mar. 21, 2014, Highly multiplexed subcellular RNA sequencing in situ. Science. 343(6177):1360-1363.
Liu et al., Single-cell transcriptome sequencing: recent advances and remaining challenges, F1000Research 2016, 5(F1000 Faculty Rev):182, 9 pp.
Lizardi et al., Jul. 1998, Mutation detection and single-molecule counting using isothermal rolling-circle amplification. Nat Genet. 19(3):225-32.
Lockhart et al., 1996, Expression monitoring by hybridization to high-density oligonucleotide arrays. Nature Biotechnology, 14:1675-1680.
Lovatt et al., Feb. 2014, Transcriptome in vivo analysis (TIVA) of spatially defined single cells in live tissue. Nat Methods. 11(2):190-196.
Lucito et al., 1996, Representational Oligonucleotide Microarray Analysis: A High-Resolution Method to Detect Genome Copy Number Variation. Genome Research, 13: 2291-2305.
Maamar et al., 2007, Noise in Gene Expression Determines Cell Fate in Bacillus subtilis. Science, 317:526-529.
Macaulay et al., 2015, G&T-seq: parallel sequencing of single-cell genomes and transcriptomes. Nature Methods, pp. 1-7.
Macosko et al., 2015, Highly parallel genome-wide expression profiling of individual cells using nanoliter droplets, Cell 161:1202-1214 (and supplemental information).
Makrigiorgos et al., Sep. 2002, A PCR-Based amplification method retaining quantities difference between two complex genomes. Nature Biotech, 20(9):936-939.
Margulies et al., Sep. 15, 2005 Genome sequencing in microfabricated high-density picolitre reactors, Nature, 437:376-380.
Martinez et al., Jul. 2012, A microfluidic approach to encapsulate living cells in uniform alginate hydrogel microparticles, Macromol. Biosci, 12(7):946-951.
McCloskey et al., Dec. 2007, Encoding PCR products with batch-stamps and barcodes. Biochem Genet. 45(11-12):761-767.
Medvedev et al., Nov. 2010, Detecting copy number variation with mated short reads. Genome Res. 20(11):1613-1622.
Mei et al., Mar. 22, 2010, Identification of recurrent regions of Copy-Number Variants across multiple individuals. BMC Bioinformatics. 11:147.
Merriam-Webster, definition of associate,: http://www.merriam-webster.com/dictionary/associate, accessed Apr. 5, 2016.
Miller et al., 2006, Directed evolution by in vitro compartmentalization, Nature Methods, 3:561-570.
Miner et al., 2004, Molecular barcodes detect redundancy and contamination in hairpin-bisulfite PCR, Nucleic Acids Research, 32(17):e135.
Mortazavi et al., 2008, Mapping and quantifying mammalian transcriptomes by RNA-Seq. Nat. Methods. 5:621-628.

(56) References Cited

OTHER PUBLICATIONS

Nadai et al., 2008, Protocol for nearly full-length sequencing of HIV-1 RNA from plasma, PLoS ONE, 3(1):e1420.
Nagai et al., 2001, Development of a microchamber array for picoleter PCR, Anal. Chem., 73:1043-1047.
Navin et al., 2015, The first five years of single-cell cancer genomics and beyond, Genome Research, 25(10):1499-1507.
Newell et al., Jan. 27, 2012, Cytometry by time-of-flight shows combinatorial cytokine expression and virus-specific cell niches within a continuum of CD8+ T cell phenotypes. Immunity. 36(1):142-152.
Novak et al., Jan. 20, 2011, Single-cell multiplex gene detection and sequencing with microfluidically generated agarose emulsions, Angew Chem Int Ed Engl., 50(2):390-395.
Ogino et al., Nov. 2002, Quantification of PCR bias caused by a single nucleotide polymorphism in SMN gene dosage analysis. J Mol Diagn. 4(4):185-190.
Parameswaran et al., 2007, A pyrosequencing-tailored nucleotide barcode design unveils opportunities for large-scale sample multiplexing. Nucleic Acids Res. 35(19):e130.
Park et al., May 2010, Discovery of common Asian copy number variants using integrated high-resolution array CGH and massively parallel DNA sequencing. Nat Genet. 42(5):400-405.
Patanjali et al., Mar. 1991, Construction of a uniform-abundance (normalized) CNDA library, Proceedings of the National Academy of Sciences, 88(5):1943-1947.
Peng et al., Mar. 11, 2016, Reducing amplification artifacts in high multiplex amplicon sequencing by using molecular barcodes, BMC Genomics, retrieved from the internet: url:http://bmcgenomics.biomedcentral.com/articles/0.1186/s12864-015-1806-8, 14 pp.
Pfaffl et al., Mar. 2004, Determination of stable housekeeping genes, differentially regulated target genes and sample integrity: BestKeeper—Excel-based tool using pair-wise correlations, Biotechnology Letters, 26(6):505-515.
Picelli et al., Jul. 30, 2014, Tn5 transposase and tagmentation procedures for massively scaled sequencing projects, Genome Research 24(12):2033-2040.
Pihlak et al., 2008, Rapid genome sequencing with short universal tiling probes. Nature Biotechnology, 26:676-684.
Pinkel et al., 2005, Comparative Genomic Hybridization. Annual Review of Genomics and Human Genetics, 6:331-354.
Pleasance et al., Jan. 14, 2010, A small-cell lung cancer genome with complex signatures of tobacco exposure. Nature. 463(7278):184-190.
Plessy et al., Feb. 2013, Population transcriptomics with single-cell resolution: a new field made possible by microfluidics: a technology for high throughput transcript counting and data-driven definition of cell types, Bioessays, 35(2):131-140.
Qiu et al., Oct. 2003, DNA sequence-based "bar codes" for tracking the origins of expressed sequence tags from a maize cDNA library constructed using multiple mRNA sources. Plant Physiol. 133(2):475-481.
Rajeevan et al., Oct. 2003, Global amplification of sense RNA: a novel method to replicate and archive mRNA for gene expression analysis, Genomics, 82(4):491-497.
Roche Diagnostics GmbH, 2006, Genome Sequencer 20 System: First to the Finish (product brochure), 40 pp.
Sasagawa et al., 2013, Quartz-Seq: a highly reproducible and sensitive single-cell RNA sequencing method, reveals non-genetic gene-expression heterogeneity. Genome Biology, 14:R31.
Sasuga et al., Dec. 2008, Single-cell chemical lysis method for analyses of intracellular molecules using an array of picoliter-scale microwells, Anal Chem, 80(23):9141-9149.
Satija et al., May 2015, Spatial reconstruction of single-cell gene expression data. Nature Biotechnology, 33(5):495-508.
Schmitt et al., Sep. 4, 2012, Detection of ultra-rare mutations by next-generation sequencing. Proc Natl Acad Sci U S A. 109(36):14508-14513.
Sebat et al., 2004, Large-Scale Copy Number Polymorphism in the Human Genome. Science, 305:525-528.
Shalek et al., Jun. 13, 2013, Single-cell transcriptomics reveals bimodality in expression and splicing in immune cells. Nature. 498(7453):236-240.
Shiroguchi et al., Jan. 24, 2012, Digital RNA sequencing minimizes sequence-dependent bias and amplification noise with optimized single-molecule barcodes. Proc Natl Acad Sci U S A. 109(4):1347-1352.
Shoemaker et al., 1996, Quantitative phenotypic analysis of yeast deletion mutants using a highly parallel molecular bar-coding strategy. Nature Genetics, 14:450-456.
Simpson et al., Feb. 15, 2010, Copy number variant detection in inbred strains from short read sequence data. Bioinformatics. 26(4):565-567.
Smith et al., 2010, Highly-multiplexed barcode sequencing: an efficient method for parallel analysis of pooled samples. Nucleic Acids Research, 38(13):e142.
Soumillon et al., Mar. 5, 2014, Characterization of directed differentiation by high-throughput single-cell RNA-Seq, bioRxiv preprint, http://bioRxiv.org/content/early/2014/03/05/003236.full.pdf, 13 pp.
Speicher et al., Oct. 2005, The new cytogenetics: blurring the boundaries with molecular biology, Nature Reviews Genetics, 6(10):782-792.
Stratagene 1998 Catalog, Gene Characterization Kits, p. 39.
Takahashi et al., Mar. 2006, Novel technique of quantitative nested real-time PCR assay for *Mycobacterium tuberculosis* DNA, Journal of Clinical Microbiology, 44(3):1029-1039.
Tan et al., Apr. 2013, Genome-wide comparison of DNA hydroxymethylation in mouse embryonic stem cells and neural progenitor cells by a new comparative hMeDIP-seq method. Nucleic Acids Res. 41(7):e84.
Taudien et al., Apr. 19, 2010, Haplotyping and copy number estimation of the highly polymorphic human beta-defensin locus on 8p23 by 454 amplicon sequencing. BMC Genomics. 11:252.
The Tibbs Times, UNC bioscience newsletter, Apr. 2010, 17 pp.
Tomaz et al., Aug. 2010, Differential methylation as a cause of allele dropout at the imprinted GNAS locus. Genet Test Mol Biomarkers. 14(4):455-460.
Treutlein et al., May 15, 2014, Reconstructing lineage hierarchies of the distal lung epithelium using single-cell RNA-seq. Nature. 509(7500):371-375.
Vandesompele et al., Jun. 18, 2002, Accurate normalization of real-time quantitative RT-PCR data by geometric averaging of multiple internal control genes, Genome Biology, 3(7).
Velculescu et al., 1995, Serial Analysis of Gene Expression. Science, 270:484-487.
Velculescu et al., 1997, Characterization of the Yeast Transcriptome. Cell, 88:243-251.
Vogelstein et al., 1999, Digital PCR. Proc. Natl. Acad. Sci., 96(16):9236-9241.
Walker et al., Jan. 1, 1992, Isothermal in vitro amplification of DNA by a restriction enzyme/DNA polymerase system. Proc Natl Acad Sci U S A., 89(1):392-396.
Walsh et al., Jul. 13, 2010, Detection of inherited mutations for breast and ovarian cancer using genomic capture and massively parallel sequencing. Proc Natl Acad Sci U S A. 107(28):12629-12633.
Wang et al., 2009, RNA-Seq: a revolutionary tool for transcriptomics. Nature Reviews Genetics, 10:57-63.
Wang et al., May 21, 2015, Advances and applications of single-cell sequencing technologies, Molecular Cell, 58(4):598-609.
Wang et al., Oct. 2010, iCLIP predicts the dual splicing effects of TIA-RNA interactions, PLoS Biol, 8(10):e1000530.
Warren et al., Nov. 21, 2006, Transcription factor profiling in individual hematopoietic progenitors by digital RT-PCR, PNAS, 103(47):17807-17812.
Weber et al., Sep. 15, 2003, A real-time polymerase chain reaction assay for quantification of allele ratios and correction of amplification bias. Anal Biochem. 320(2):252-258.
Weiner et al., Apr. 2008, Kits and their unique role in molecular biology: a brief retrospective, BioTechniques, 44:701-704.
White et al., Aug. 23, 2011, High-throughput microfluidic single-cell RT-qPCR, PNAS, 108(34):13999-14004.

(56) References Cited

OTHER PUBLICATIONS

Wittes et al., 1999, Searching for Evidence of Altered Gene Expression: a Comment on Statistical Analysis of Microarray Data. Journal of the National Cancer Institute, 91(5):400-401.
Wodicka et al., 1997, Genome-wide expression monitoring in *Saccharomyces cerevisiae*. Nature Biotechnology, 15:1359-1367.
Wojdacz et al., May 16, 2009, Primer design versus PCR bias in methylation independent PCR amplifications. Epigenetics. 4(4):231-234.
Wood et al., Aug. 2010, Using next-generation sequencing for high resolution multiplex analysis of copy number variation from nanogram quantities of DNA from formalin-fixed paraffin-embedded specimens. Nucleic Acids Res. 38(14):e151.
Wu et al., Jan. 2014, Quantitative assessment of single-cell RNA-sequencing methods. Nat Methods. 11(1):41-46.
Yandell et al., Sep. 2011, A probabilistic disease-gene finder for personal genomes. Genome Res. 21(9):1529-1542.
Ye et al., 2001, Fluorescent microsphere-based readout technology for multiplexed human single nucleotide polymorphism analysis and bacterial identification. Human Mutation, 17(4):305-316.
Yoon et al., Sep. 2009, Sensitive and accurate detection of copy number variants using read depth of coverage. Genome Res. 19(9):1586-1592.
Zhang et al., Jun. 19, 2012, DNA-based hybridization chain reaction for amplified bioelectronic signal and ultrasensitive detection of proteins. Anal Chem., 84(12),5392-5399.
Zhang et al., Mar. 20, 2011, The impact of next-generation sequencing on genomics. J Genet Genomics. 38(3):95-109.
Zhao et al., 2005, Homozygous Deletions and Chromosome Amplifications in Human Lung Carcinomas Revealed by Single Nucleotide Polymorphism Array Analysis. Cancer Research, 65:5561-5570.
Zheng et al., Feb. 2016, Haplotyping germline and cancer genomes with high-throughput linked-read sequencing, Nature Biotechnology, 34(3):303-311.
Zhou et al., 2001, Counting alleles reveals a connection between chromosome 18q loss and vascular invasion. Nature Biotechnology, 19:78-81.
International Search Report and Written Opinion dated May 3, 2016 in PCT/US16/018354.
Office action dated Oct. 3, 2013 for U.S. Appl. No. 12/969,581.
Response with allowed claims dated Mar. 4, 2014 for U.S. Appl. No. 12/969,581.
Notice of allowance dated Mar. 21, 2014 for U.S. Appl. No. 12/969,581.
Notice of allowance dated Jun. 19, 2014 for U.S. Appl. No. 12/969,581.
Notice of allowance dated Aug. 22, 2014 for U.S. Appl. No. 12/969,581.
Office action dated Dec. 3, 2015 for U.S. Appl. No. 14/281,706.
Office action dated Jul. 20, 2016 for U.S. Appl. No. 14/281,706.
Office Action dated Oct. 11, 2016 in U.S. Appl. No. 15/224,460.
Office Action dated May 8, 2017 in U.S. Appl. No. 15/224,460.
Office Action dated May 7, 2015 for U.S. Appl. No. 13/327,526.
Notice of allowance dated Jan. 21, 2016 for U.S. Appl. No. 13/327,526.
Office action dated Feb. 18, 2015 for U.S. Appl. No. 14/540,007.
Office action dated Sep. 24, 2015 for U.S. Appl. No. 14/540,007.
Notice of allowance dated Dec. 15, 2015 for U.S. Appl. No. 14/540,007.
Office action dated Mar. 19, 2015 for U.S. Appl. No. 14/540,018.
Office action dated Oct. 6, 2015 for U.S. Appl. No. 14/540,018.
Notice of allowance dated Dec. 21, 2015 for U.S. Appl. No. 14/540,018.
Office Action dated Feb. 26, 2015 for U.S. Appl. No. 14/540,029.
Office action dated Sep. 1, 2015 for U.S. Appl. No. 14/540,029.
Office Action dated Jul. 28, 2017 in U.S. Appl. No. 14/975,441.
International Search Report and Written Opinion dated Jun. 6, 2012 in PCT/US11/065291.
Restriction Requirement dated Mar. 15, 2016 in U.S. Appl. No. 14/381,488.
Office Action dated May 10, 2016 in U.S. Appl. No. 14/381,488.
Office Action dated Aug. 12, 2016 in U.S. Appl. No. 14/381,488.
Office Action dated Feb. 13, 2017 in U.S. Appl. No. 14/381,488.
Office Action dated Jun. 7, 2017 in U.S. Appl. No. 14/381,488.
International Search Report and Written Opinion dated Sep. 6, 2013 in PCT/US13/028103.
Office Action dated Feb. 17, 2017 in Canadian patent application No. 2,865,575.
Second Office Action dated Jun. 6, 2016 in Chinese patent application No. 201380022187.9.
Third Office Action dated Dec. 27, 2016 in Chinese patent application No. 201380022187.9.
Fourth Office Action dated Jul. 14, 2017 in Chinese patent application No. 201380022187.9.
European search report and search opinion dated Jul. 17, 2015 for European patent application No. 13755319.4.
Examination report dated Jul. 12, 2016 in European patent application No. 13755319.4.
Search and Examination Report dated Aug. 6, 2014 for GB patent application No. 1408829.8.
Search and Examination Report dated Jan. 27, 2016 in GB patent application No. 1408829.8.
Examination Report dated Jun. 8, 2016 in GB patent application No. 1408829.8.
Official Action dated Dec. 28, 2016 in Japanese patent application No. 2014-558975.
Written Opinion dated May 26, 2017 in Singapore patent application No. 11201405274W.
International search report and written opinion dated Aug. 16, 2013 for PCT/US2013/027891.
Extended European Search Report dated Dec. 15, 2015 in European patent application No. 13754428.4.
Restriction Requirement dated Mar. 17, 2016 in U.S. Appl. No. 14/472,363.
Office Action dated Apr. 11, 2016 in U.S. Appl. No. 14/472,363.
Office action dated Dec. 31, 2015 for U.S. Appl. No. 14/800,526.
Office action dated Apr. 11, 2016 for U.S. Appl. No. 14/800,526.
Office action dated Aug. 17, 2016 for U.S. Appl. No. 14/800,526.
Office Action dated Oct. 25, 2016 in U.S. Appl. No. 14/872,337.
Office action dated Sep. 26, 2016 in U.S. Appl. No. 15/167,807.
International Search Report and Written Opinion dated Feb. 3, 2015 in PCT/US/14/053301.
Examination Report dated Apr. 10, 2017 in European patent application No. 14761937.3.
Search and Examination Report dated Aug. 26, 2015 in GB patent application No. 1511591.8.
Examination Report dated Feb. 19, 2016 in Great Britain patent application No. GB1511591.8.
Examination Report dated Jun. 15, 2016 in Great Britain patent application No. GB1511591.8.
Combined Search and Examination Report dated Feb. 21, 2017 in GB patent application No. 1609740.4.
Office Action dated May 13, 2016 in U.S. Appl. No. 14/508,911.
Office Action dated Mar. 24, 2017 in U.S. Appl. No. 15/409,355.
International search report and written opinion dated Dec. 19, 2014 for PCT Application No. US2014/059542.
International Search Report and Written Opinion dated Jun. 20, 2016 in PCT/US16/14612.
Office Action dated Jan. 19, 2017 in U.S. Appl. No. 15/055,445.
International Search Report and Written Opinion dated Jun. 17, 2016 in PCT/US16/019962.
Written Opinion dated Jul. 5, 2016 in PCT/US16/019962.
Written Opinion dated Sep. 27, 2016 in PCT/US16/019962.
Invitation to Pay Additional Search Fees dated Jun. 2, 2016 in PCT/US16/019971.
International Search Report and Written Opinion dated Aug. 9, 2016 in PCT/US16/019971.
International Search Report and Written Opinion dated Jun. 9, 2016 in PCT/US16/022712.
International Search Report and Written Opinion dated Dec. 5, 2016 in PCT/US16/024783.

(56) References Cited

OTHER PUBLICATIONS

International Search Report and Written Opinion dated Sep. 28, 2016 in PCT/US16/028694.
International Search Report and Written Opinion dated Sep. 27, 2016 in PCT/US16/034473.
International Search Report and Written Opinion dated Jan. 31, 2017 in PCT/US16/050694.
International Search Report and Written Opinion dated Aug. 7, 2017 in PCT/US2017/034576.
International search report and written opinion dated May 7, 2012 for PCT/IB2011/003160.
Notice of opposition dated Jul. 22, 2015 for European patent application No. 11810645.9.
Notice of opposition dated Jul. 9, 2015 for European patent application No. 11810645.9.

* cited by examiner

FIG. 3A

Baseline

5′[Adapter][Sample Barcode]NNNNNNNN[Uniform Region, Gene Specific Region, or oligo dT] 3′

FIG. 3B

Add 3 base spacer before MI/SI

5′[Adapter][Sample Barcode]NNNNNNNNTTT[Uniform Region, Gene Specific Region, or oligo dT] 3′

FIG. 3C

Add 5 base spacer before MI/SI

5′[Adapter][Sample Barcode]NNNNNNNNTTTTT[Uniform Region, Gene Specific Region, or oligo dT]3′

FIG. 3D

Switch SI and MI positions

5′ [Adapter]NNNNNNNN[Sample Barcode][Uniform Region, Gene Specific Region, or oligo dT] 3′

FIG. 3E

Switch SI and MI position, add 3 base spacer

5′ [Adapter]NNNNNNNN[Sample Barcode]TTT[Uniform Region, Gene Specific Region, or oligo dT] 3′

FIG. 3F

Switch SI and MI position, add 5 base spacer

5′[Adapter]NNNNNNNN[Sample Barcode]TTTTT[Uniform Region, Gene Specific Region, or oligo dT]3′

FIG. 3G

Switch MI format from 'NNNNNNNN' to 'HHHHHHHH'

5′ [Adapter][Sample Barcode]HHHHHHHH[Uniform Region, Gene Specific Region, or oligo dT] 3′

FIG. 3H

Switch MI format from 'NNNNNNNN' to 'HNHNHNHN'

5′ [Adapter][Sample Barcode]HNHNHNHN[Uniform Region, Gene Specific Region, or oligo dT] 3′

ES32, TRBC, Entire MI Nucleotide Usage

ES32, TRBC, Entire MI Nucleotide Usage

ES32, OligodT, Entire MI Nucleotide Usage

FIG. 5A

| Sample | Anchor (SEQ ID NO: 97) | 1st bc | 2nd bc | Spacer | 5' to 3' Recognition Sequence | SEQ ID NO: (anchor + 1st & 2nd bc + spacer + 5' to 3' rec. sequence) |
|---|---|---|---|---|---|---|
| A01 | ACACGACGCTCTTCCGATCT | ACAGTGCT | NNNNNNNN | | CAGACAGACTTGT | SEQ ID NO. 1 |
| A02 | ACACGACGCTCTTCCGATCT | ACATGCGT | NNNNNNNN | | CAGACAGACTTGT | SEQ ID NO. 2 |
| A03 | ACACGACGCTCTTCCGATCT | ACCGATTG | NNNNNNNN | | CAGACAGACTTGT | SEQ ID NO. 3 |
| A04 | ACACGACGCTCTTCCGATCT | ACCTTGAG | NNNNNNNN | | CAGACAGACTTGT | SEQ ID NO. 4 |
| A05 | ACACGACGCTCTTCCGATCT | ACGATGTC | NNNNNNNN | | CAGACAGACTTGT | SEQ ID NO. 5 |
| A06 | ACACGACGCTCTTCCGATCT | ACGTATGC | NNNNNNNN | | CAGACAGACTTGT | SEQ ID NO. 6 |
| A07 | ACACGACGCTCTTCCGATCT | ACTCTGGA | NNNNNNNN | | CAGACAGACTTGT | SEQ ID NO. 7 |
| A08 | ACACGACGCTCTTCCGATCT | ACTGGCTA | NNNNNNNN | | CAGACAGACTTGT | SEQ ID NO. 8 |
| A09 | ACACGACGCTCTTCCGATCT | AGACCTTG | NNNNNNNN | | CAGACAGACTTGT | SEQ ID NO. 9 |
| A10 | ACACGACGCTCTTCCGATCT | AGATTCCG | NNNNNNNN | | CAGACAGACTTGT | SEQ ID NO. 10 |
| A11 | ACACGACGCTCTTCCGATCT | AGCCGACC | NNNNNNNN | | CAGACAGACTTGT | SEQ ID NO. 11 |
| A12 | ACACGACGCTCTTCCGATCT | AGCGCTGC | NNNNNNNN | | CAGACAGACTTGT | SEQ ID NO. 12 |
| B01 | ACACGACGCTCTTCCGATCT | AGCTAGTC | NNNNNNNN | TTT | CAGACAGACTTGT | SEQ ID NO. 13 |
| B02 | ACACGACGCTCTTCCGATCT | AGGCTCTA | NNNNNNNN | TTT | CAGACAGACTTGT | SEQ ID NO. 14 |
| B03 | ACACGACGCTCTTCCGATCT | AGGTCTCA | NNNNNNNN | TTT | CAGACAGACTTGT | SEQ ID NO. 15 |
| B04 | ACACGACGCTCTTCCGATCT | AGTACTAT | NNNNNNNN | TTT | CAGACAGACTTGT | SEQ ID NO. 16 |
| B05 | ACACGACGCTCTTCCGATCT | AGTCAGCT | NNNNNNNN | TTT | CAGACAGACTTGT | SEQ ID NO. 17 |
| B06 | ACACGACGCTCTTCCGATCT | AGTGTCGT | NNNNNNNN | TTT | CAGACAGACTTGT | SEQ ID NO. 18 |
| B07 | ACACGACGCTCTTCCGATCT | ATACGTGC | NNNNNNNN | TTT | CAGACAGACTTGT | SEQ ID NO. 19 |
| B08 | ACACGACGCTCTTCCGATCT | ATAGCGTC | NNNNNNNN | TTT | CAGACAGACTTGT | SEQ ID NO. 20 |
| B09 | ACACGACGCTCTTCCGATCT | ATCGGTCA | NNNNNNNN | TTT | CAGACAGACTTGT | SEQ ID NO. 21 |
| B10 | ACACGACGCTCTTCCGATCT | ATCTCGGA | NNNNNNNN | TTT | CAGACAGACTTGT | SEQ ID NO. 22 |
| B11 | ACACGACGCTCTTCCGATCT | ATGACGCT | NNNNNNNN | TTT | CAGACAGACTTGT | SEQ ID NO. 23 |
| B12 | ACACGACGCTCTTCCGATCT | ATTCCGAG | NNNNNNNN | TTT | CAGACAGACTTGT | SEQ ID NO. 24 |

FIG. 5B

| Sample | Anchor (SEQ ID NO: 97) | 1st bc | 2nd bc | Spacer | 5 to 3' Recognition Sequence | SEQ ID NO: (anchor + 1st & 2nd bc + spacer + 5' to 3' rec. sequence) |
|---|---|---|---|---|---|---|
| *C01* | ACACGACGCTCTTCCGATCT | ATTGACCG | NNNNNNNN | TTTTT | CAGACAGACTTGT | SEQ ID NO. 25 |
| *C02* | ACACGACGCTCTTCCGATCT | CAGAGTTC | NNNNNNNN | TTTTT | CAGACAGACTTGT | SEQ ID NO. 26 |
| *C03* | ACACGACGCTCTTCCGATCT | CAGCCGAC | NNNNNNNN | TTTTT | CAGACAGACTTGT | SEQ ID NO. 27 |
| *C04* | ACACGACGCTCTTCCGATCT | CAGTTAGC | NNNNNNNN | TTTTT | CAGACAGACTTGT | SEQ ID NO. 28 |
| *C05* | ACACGACGCTCTTCCGATCT | CATCGTGA | NNNNNNNN | TTTTT | CAGACAGACTTGT | SEQ ID NO. 29 |
| *C06* | ACACGACGCTCTTCCGATCT | CATGCGTA | NNNNNNNN | TTTTT | CAGACAGACTTGT | SEQ ID NO. 30 |
| *C07* | ACACGACGCTCTTCCGATCT | CCAGTTAG | NNNNNNNN | TTTTT | CAGACAGACTTGT | SEQ ID NO. 31 |
| *C08* | ACACGACGCTCTTCCGATCT | CCATGGCG | NNNNNNNN | TTTTT | CAGACAGACTTGT | SEQ ID NO. 32 |
| *C09* | ACACGACGCTCTTCCGATCT | CCGATTGA | NNNNNNNN | TTTTT | CAGACAGACTTGT | SEQ ID NO. 33 |
| *C10* | ACACGACGCTCTTCCGATCT | CGACCAGC | NNNNNNNN | TTTTT | CAGACAGACTTGT | SEQ ID NO. 34 |
| *C11* | ACACGACGCTCTTCCGATCT | CGAGATTC | NNNNNNNN | TTTTT | CAGACAGACTTGT | SEQ ID NO. 35 |
| *C12* | ACACGACGCTCTTCCGATCT | CGATTGAC | NNNNNNNN | TTTTT | CAGACAGACTTGT | SEQ ID NO. 36 |
| *D01* | ACACGACGCTCTTCCGATCT | NNNNNNNN | CGCATGTA | | CAGACAGACTTGT | SEQ ID NO. 37 |
| *D02* | ACACGACGCTCTTCCGATCT | NNNNNNNN | CGCTATGA | | CAGACAGACTTGT | SEQ ID NO. 38 |
| *D03* | ACACGACGCTCTTCCGATCT | NNNNNNNN | CGTACATG | | CAGACAGACTTGT | SEQ ID NO. 39 |
| *D04* | ACACGACGCTCTTCCGATCT | NNNNNNNN | CGTCATAG | | CAGACAGACTTGT | SEQ ID NO. 40 |
| *D05* | ACACGACGCTCTTCCGATCT | NNNNNNNN | CTACGACA | | CAGACAGACTTGT | SEQ ID NO. 41 |
| *D06* | ACACGACGCTCTTCCGATCT | NNNNNNNN | CTAGCTGA | | CAGACAGACTTGT | SEQ ID NO. 42 |
| *D07* | ACACGACGCTCTTCCGATCT | NNNNNNNN | CTATAGTA | | CAGACAGACTTGT | SEQ ID NO. 43 |
| *D08* | ACACGACGCTCTTCCGATCT | NNNNNNNN | CTGACTAG | | CAGACAGACTTGT | SEQ ID NO. 44 |
| *D09* | ACACGACGCTCTTCCGATCT | NNNNNNNN | CTGCAGCG | | CAGACAGACTTGT | SEQ ID NO. 45 |
| *D10* | ACACGACGCTCTTCCGATCT | NNNNNNNN | CTGTGATG | | CAGACAGACTTGT | SEQ ID NO. 46 |
| *D11* | ACACGACGCTCTTCCGATCT | NNNNNNNN | CTTAGAGC | | CAGACAGACTTGT | SEQ ID NO. 47 |
| *D12* | ACACGACGCTCTTCCGATCT | NNNNNNNN | CTTGAGAC | | CAGACAGACTTGT | SEQ ID NO. 48 |

FIG. 5C

| Sample | Anchor (SEQ ID NO: 97) | 1st bc | 2nd bc | Spacer | 5 to 3' Recognition Sequence | SEQ ID NO: (anchor + 1st & 2nd bc + spacer + 5' to 3' rec. sequence) |
|---|---|---|---|---|---|---|
| *E01* | ACACGACGCTCTTCCGATCT | NNNNNNNN | GACCAGCC | TTT | CAGACAGACTTGT | SEQ ID NO. 49 |
| *E02* | ACACGACGCTCTTCCGATCT | NNNNNNNN | GACGTCGC | TTT | CAGACAGACTTGT | SEQ ID NO. 50 |
| *E03* | ACACGACGCTCTTCCGATCT | NNNNNNNN | GACTGATC | TTT | CAGACAGACTTGT | SEQ ID NO. 51 |
| *E04* | ACACGACGCTCTTCCGATCT | NNNNNNNN | GAGCCTTA | TTT | CAGACAGACTTGT | SEQ ID NO. 52 |
| *E05* | ACACGACGCTCTTCCGATCT | NNNNNNNN | GAGTTCCA | TTT | CAGACAGACTTGT | SEQ ID NO. 53 |
| *E06* | ACACGACGCTCTTCCGATCT | NNNNNNNN | GATATCAT | TTT | CAGACAGACTTGT | SEQ ID NO. 54 |
| *E07* | ACACGACGCTCTTCCGATCT | NNNNNNNN | GATCGACT | TTT | CAGACAGACTTGT | SEQ ID NO. 55 |
| *E08* | ACACGACGCTCTTCCGATCT | NNNNNNNN | GATGCTGT | TTT | CAGACAGACTTGT | SEQ ID NO. 56 |
| *E09* | ACACGACGCTCTTCCGATCT | NNNNNNNN | GCAGTATC | TTT | CAGACAGACTTGT | SEQ ID NO. 57 |
| *E10* | ACACGACGCTCTTCCGATCT | NNNNNNNN | GCATGTAC | TTT | CAGACAGACTTGT | SEQ ID NO. 58 |
| *E11* | ACACGACGCTCTTCCGATCT | NNNNNNNN | GCCAGTTA | TTT | CAGACAGACTTGT | SEQ ID NO. 59 |
| *E12* | ACACGACGCTCTTCCGATCT | NNNNNNNN | GCCGACCA | TTT | CAGACAGACTTGT | SEQ ID NO. 60 |
| *F01* | ACACGACGCTCTTCCGATCT | NNNNNNNN | GCCTTAGA | TTTTT | CAGACAGACTTGT | SEQ ID NO. 61 |
| *F02* | ACACGACGCTCTTCCGATCT | NNNNNNNN | GCGATACT | TTTTT | CAGACAGACTTGT | SEQ ID NO. 62 |
| *F03* | ACACGACGCTCTTCCGATCT | NNNNNNNN | GCGTACAT | TTTTT | CAGACAGACTTGT | SEQ ID NO. 63 |
| *F04* | ACACGACGCTCTTCCGATCT | NNNNNNNN | GGCATTGT | TTTTT | CAGACAGACTTGT | SEQ ID NO. 64 |
| *F05* | ACACGACGCTCTTCCGATCT | NNNNNNNN | GGCGCCAT | TTTTT | CAGACAGACTTGT | SEQ ID NO. 65 |
| *F06* | ACACGACGCTCTTCCGATCT | NNNNNNNN | GGTGTTAC | TTTTT | CAGACAGACTTGT | SEQ ID NO. 66 |
| *F07* | ACACGACGCTCTTCCGATCT | NNNNNNNN | GTACGCAT | TTTTT | CAGACAGACTTGT | SEQ ID NO. 67 |
| *F08* | ACACGACGCTCTTCCGATCT | NNNNNNNN | GTCGGCTG | TTTTT | CAGACAGACTTGT | SEQ ID NO. 68 |
| *F09* | ACACGACGCTCTTCCGATCT | NNNNNNNN | GTGACATC | TTTTT | CAGACAGACTTGT | SEQ ID NO. 69 |
| *F10* | ACACGACGCTCTTCCGATCT | NNNNNNNN | GTGCATAC | TTTTT | CAGACAGACTTGT | SEQ ID NO. 70 |
| *F11* | ACACGACGCTCTTCCGATCT | NNNNNNNN | GTGTGCGC | TTTTT | CAGACAGACTTGT | SEQ ID NO. 71 |
| *F12* | ACACGACGCTCTTCCGATCT | NNNNNNNN | GTTAGCCA | TTTTT | CAGACAGACTTGT | SEQ ID NO. 72 |

FIG. 5D

| Sample | Anchor (SEQ ID NO: 97) | 1st bc | 2nd bc | Spacer | 5 to 3' Recognition Sequence | SEQ ID NO: (anchor + 1st & 2nd bc + spacer + 5' to 3' rec. sequence) |
|---|---|---|---|---|---|---|
| *G01* | ACACGACGCTCTTCCGATCT | GTTCCAGA | HHHHHHHH | | CAGACAGACTTGT | SEQ ID NO. 73 |
| *G02* | ACACGACGCTCTTCCGATCT | TACGTGCA | HHHHHHHH | | CAGACAGACTTGT | SEQ ID NO. 74 |
| *G03* | ACACGACGCTCTTCCGATCT | TACTGCGA | HHHHHHHH | | CAGACAGACTTGT | SEQ ID NO. 75 |
| *G04* | ACACGACGCTCTTCCGATCT | TAGAGCCT | HHHHHHHH | | CAGACAGACTTGT | SEQ ID NO. 76 |
| *G05* | ACACGACGCTCTTCCGATCT | TAGCCAGT | HHHHHHHH | | CAGACAGACTTGT | SEQ ID NO. 77 |
| *G06* | ACACGACGCTCTTCCGATCT | TATCGCAG | HHHHHHHH | | CAGACAGACTTGT | SEQ ID NO. 78 |
| *G07* | ACACGACGCTCTTCCGATCT | TCAGTCGA | HHHHHHHH | | CAGACAGACTTGT | SEQ ID NO. 79 |
| *G08* | ACACGACGCTCTTCCGATCT | TCATGATA | HHHHHHHH | | CAGACAGACTTGT | SEQ ID NO. 80 |
| *G09* | ACACGACGCTCTTCCGATCT | TCCAGAGT | HHHHHHHH | | CAGACAGACTTGT | SEQ ID NO. 81 |
| *G10* | ACACGACGCTCTTCCGATCT | TCCGAGAT | HHHHHHHH | | CAGACAGACTTGT | SEQ ID NO. 82 |
| *G11* | ACACGACGCTCTTCCGATCT | TCGATCAG | HHHHHHHH | | CAGACAGACTTGT | SEQ ID NO. 83 |
| *G12* | ACACGACGCTCTTCCGATCT | TCGCGACG | HHHHHHHH | | CAGACAGACTTGT | SEQ ID NO. 84 |
| *H01* | ACACGACGCTCTTCCGATCT | TCGGCTGG | HNHNHNHN | | CAGACAGACTTGT | SEQ ID NO. 85 |
| *H02* | ACACGACGCTCTTCCGATCT | TCGTAGTG | HNHNHNHN | | CAGACAGACTTGT | SEQ ID NO. 86 |
| *H03* | ACACGACGCTCTTCCGATCT | TGACCGAT | HNHNHNHN | | CAGACAGACTTGT | SEQ ID NO. 87 |
| *H04* | ACACGACGCTCTTCCGATCT | TGAGACCT | HNHNHNHN | | CAGACAGACTTGT | SEQ ID NO. 88 |
| *H05* | ACACGACGCTCTTCCGATCT | TGCATACG | HNHNHNHN | | CAGACAGACTTGT | SEQ ID NO. 89 |
| *H06* | ACACGACGCTCTTCCGATCT | TGCGCGTG | HNHNHNHN | | CAGACAGACTTGT | SEQ ID NO. 90 |
| *H07* | ACACGACGCTCTTCCGATCT | TGCTACAG | HNHNHNHN | | CAGACAGACTTGT | SEQ ID NO. 91 |
| *H08* | ACACGACGCTCTTCCGATCT | TGTACGCA | HNHNHNHN | | CAGACAGACTTGT | SEQ ID NO. 92 |
| *H09* | ACACGACGCTCTTCCGATCT | TTACGGTG | HNHNHNHN | | CAGACAGACTTGT | SEQ ID NO. 93 |
| *H10* | ACACGACGCTCTTCCGATCT | TTAGCCAG | HNHNHNHN | | CAGACAGACTTGT | SEQ ID NO. 94 |
| *H11* | ACACGACGCTCTTCCGATCT | TTGACCGA | HNHNHNHN | | CAGACAGACTTGT | SEQ ID NO. 95 |
| *H12* | ACACGACGCTCTTCCGATCT | TTGTGGCA | HNHNHNHN | | CAGACAGACTTGT | SEQ ID NO. 96 |

ACCURATE MOLECULAR BARCODING

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

REFERENCE TO RELATED APPLICATIONS

The present application claims the benefit of U.S. Provisional App. No. 62/330,500 filed May 2, 2016, which is hereby incorporated by reference in its entirety.

REFERENCE TO SEQUENCE LISTING

The present application is being filed along with a Sequence Listing in electronic format. The Sequence Listing is provided as a file entitled SEQUENCEBDCRI019A.TXT, created and last modified Apr. 21, 2017, which is 32,587 bytes in size, *and is replaced by a file entitled BDCRI019R1_SEQLIST.xml, created and last modified Oct. 25, 2022, which is 195,405 bytes in size*. The information in the electronic format of the Sequence Listing is incorporated herein by reference in its entirety.

FIELD

Embodiments herein relate generally to compositions and methods for accurate barcoding of molecules, for example nucleic acid molecules.

SUMMARY

Some embodiments include a composition comprising at least 1000 unique oligonucleotide species is provided. Each unique oligonucleotide species can comprise a barcode region comprising a molecule barcode comprising at least 7 nucleotides, in which the unique oligonucleotide species comprise different nucleic acid sequences in their barcode regions, and in which at least one of: (a) the composition consists essentially of unique oligonucleotide species wherein each molecular barcode has a G content of less than 50%; or (b) the molecule barcodes of all of the unique oligonucleotide species in the composition collectively have a G content of no more than 12.5%. In some embodiments, the barcode region further comprises a sample barcode comprising at least 3 nucleotides. In some embodiments, each unique oligonucleotide species further comprises a uniform region 3' of the barcode region. In some embodiments, the uniform region further comprises a target-specific region 3' of the barcode region, the target-specific region comprising at least 10 nucleotides complementary to a target nucleic acid. In some embodiments, the composition consists essentially of unique oligonucleotide species wherein each molecular barcode has a G content of less than 50%. In some embodiments, the molecule barcodes of all of the unique oligonucleotide species in the composition collectively have a G content of no more than 12.5%. In some embodiments, the unique oligonucleotide species are disposed in at least two spatially isolated pools, each pool comprising at least 100 unique oligonucleotides of the unique oligonucleotide species, wherein unique oligonucleotides in the same pool comprise the same sample barcode sequence, and wherein different unique oligonucleotides of the same pool comprise a different molecule barcode sequences. In some embodiments, the sample barcode of each unique oligonucleotide species has a G content of 50% or less. In some embodiments, the barcode region of each unique oligonucleotide species has a G content of 50% or less. In some embodiments, the molecule barcodes of the unique oligonucleotide species collectively have a G content of less than 12.5%. In some embodiments, the barcode regions of the unique oligonucleotide species collectively have a G content of no more than 12.5%. In some embodiments, for at least 95% of the unique oligonucleotide species, any G in the molecule barcode is not adjacent to another G. In some embodiments, the composition consists essentially of unique oligonucleotide species for which any G in the molecule barcode is not adjacent to another G. In some embodiments, at least 95% of the molecule barcodes of the unique oligonucleotide species comprise a sequence totaling at least 6 alternating H's and N's, wherein each "H" is any one of A, C, or T, and wherein each "N" is any one of A, G, C, or T. In some embodiments, least 95% of the molecule barcodes of the unique oligonucleotide species comprise the sequence HNHNHNHN, wherein each "H" is any one of A, C, or T, and wherein each "N" is any one of A, G, C, or T. In some embodiments, each molecule barcode of the unique oligonucleotide species comprises the sequence HNHNHNHN, wherein each "H" is any one of A, C, or T, and wherein each "N" is any one of A, G, C, or T. In some embodiments, each molecule barcode of the unique oligonucleotide species comprises the sequence HHHHHHHH, wherein each "H" is any one of A, C, or T. In some embodiments, each of the unique oligonucleotide species comprises a spacer 3' of the barcode region and 5' of the target specific region, said spacer comprising the sequence HNHNHNHN, wherein each "H" is any one of A, C, or T, and wherein each "N" is any one of A, G, C, or T. In some embodiments, each of the unique oligonucleotide species comprises a spacer 3' of the barcode region and 5' of the target specific region, said spacer comprising the sequence HHHHHHHH, wherein each "H" is any one of A, C, or T. In some embodiments, the target specific region comprises an oligo dT sequence. In some embodiments, for each unique oligonucleotide species, the molecule barcode is 3' of the sample barcode. In some embodiments, for each unique oligonucleotide species, the sample barcode is 3' of the molecule barcode. In some embodiments, each oligonucleotide species has a length of at least 24 nucleotides. In some embodiments, each oligonucleotide species has a length of 24-140 nucleotides. In some embodiments, the composition comprises at least 6,500 unique oligonucleotide species. In some embodiments, the composition comprises at least 65,000 unique oligonucleotide species. In some embodiments, the composition comprises at least two oligonucleotides of the same unique oligonucleotide species. In some embodiments, no two oligonucleotides of the composition are of the same unique oligonucleotide species. In some embodiments, the composition comprises at least 48 pools. In some embodiments, the unique oligonucleotide species of each pool are immobilized on a substrate, so that the sample barcodes but not the molecule barcodes are the same for the oligonucleotide species immobilized on each substrate. In some embodiments, the substrate comprises a discrete region of a surface, so that the surface can comprise two or more substrates. In some embodiments, the substrate comprises a bead. In some embodiments, each of the unique oligonucleotide species further comprises an adapter configured to immobilize the unique oligonucleotide on the substrate, wherein said barcode region is 3' of the adapter. In some embodiments, the uniform region comprises a target-specific region comprising a sequence flanking an immune cell receptor or immunoglobulin variable region coding sequence. In some embodiments, the immune cell receptor variable region coding sequence is a T cell receptor variable region coding sequence, a B cell receptor variable region coding sequence, or a combination thereof. In some embodiments, a kit comprising the composition comprising at least 1000 unique oligonucleotide species is provided. The kit can further comprise a primer configured to hybridize on an opposite side of the variable region as the target-specific region and to hybridize to a complementary strand to a strand hybridized by the target-specific region, so that the primer is configured to amplify the variable region in conjunction with the target-specific region. In some embodiments, the primer and target-specific region are configured to amplify a nucleic acid of at least 1 kb and comprising the variable region. In some embodiments, the primer of the kit is part of the composition comprising the unique oligonucleotide species. In some embodiments, the primer of the kit is part of an other composition that is separate from the composition comprising the unique oligonucleotide species.

Some embodiments include a method of specifically barcoding a plurality of nucleic acids from two or more samples is provided. Each sample can comprising nucleic acid. The method can comprise contacting each sample with a pool comprising at least 100 unique oligonucleotide species, in which each sample is contacted in spatial isolation from the other samples. Each unique oligonucleotide species can comprise a barcode region comprising a molecule barcode comprising at least 7 nucleotides. The unique polynucleotide species of each pool can comprise the same sample barcode, and comprise different molecule barcodes. In the method, at least (a) the unique oligonucleotide species contacted with the sample consist essentially of unique oligonucleotide species wherein each molecular barcode has a G content of less than 50%; or (b) the molecule barcodes of all of the unique oligonucleotide species collectively have a G content of no more than 12.5% can apply. The method can include hybridizing target-specific regions of at least some oligonucleotides of the unique oligonucleotide species to at least some of the nucleic acids of the sample. The method can include extending the hybridized oligonucleotides, thereby producing strands comprising an oligonucleotide of the unique oligonucleotide species and a sequence complementary to the target, wherein for each sample, the strands comprise the same sample barcode and different molecule barcodes, and wherein for different samples, the molecule barcodes are different. In some embodiments, the barcode region further comprises a sample barcode comprising at least 3 nucleotides. In some embodiments, each unique oligonucleotide species further comprises a uniform region 3' of the barcode region. In some embodiments, the uniform region further comprises a target-specific region 3' of the barcode region, the target-specific region comprising at least 10 nucleotides complementary to a target nucleic acid. In some embodiments, the unique oligonucleotide species contacted with the sample consist essentially of unique oligonucleotide species wherein each molecular barcode has a G content of less than 50%. In some embodiments, the molecule barcodes of all of the unique oligonucleotide species collectively have a G content of no more than 12.5%. In some embodiments, the method further comprises ascertaining nucleic acid sequences of the strands comprising the oligonucleotides of the unique oligonucleotide species and the sequence complementary to the target. In some embodiments, the at least 100 unique oligonucleotide species of each pool are immobilized on a substrate, so that the unique oligonucleotide species immobilized on a given substrate comprise the same sample barcode, and different unique oligonucleotide species immobilized on the substrate comprise different molecule barcodes. In some embodiments, each sample barcode has a G content of 50% or less. In some embodiments, the molecule barcodes of the unique oligonucleotide species collectively have a G content of less than 12.5%. In some embodiments, the barcode regions of the unique oligonucleotide species collectively have a G content of no more than 12.5%. In some embodiments, for at least 95% of the unique oligonucleotide species, any G in the molecule barcode is not adjacent to another G. In some embodiments, each pool consists essentially of unique oligonucleotide species for which any G in the molecule barcode is not adjacent to another G. In some embodiments, at least 95% of the molecule barcodes of the unique oligonucleotide species comprise a sequence totaling at least 6 alternating H's and N's, wherein each "H" is any one of A, C, or T, and wherein each "N" is any one of A, G, C, or T. In some embodiments, at least 95% of the molecule barcodes of the unique oligonucleotide species comprise the sequence HNHNHNHN, wherein each "H" is any one of A, C, or T, and wherein each "N" is any one of A, G, C, or T. In some embodiments, each molecule barcode of the unique oligonucleotide species comprises the sequence HNHNHNHN, wherein each "H" is any one of A, C, or T, and wherein each "N" is any one of A, G, C, or T. In some embodiments, each molecule barcode of the unique oligonucleotides comprises the sequence HHHHHHHH, wherein each "H" is any one of A, C, or T. In some embodiments, each unique oligonucleotide comprises a spacer 3' of the barcode region and 5' of the target specific region, said spacer comprising the sequence HNHNHNHN, wherein each "H" is any one of A, C, or T, and wherein each "N" is any one of A, G, C, or T. In some embodiments, each unique oligonucleotide comprises a spacer 3' of the barcode region and 5' of the target specific region, said spacer comprising the sequence HHHHHHHH, wherein each "H" is any one of A, C, or T. In some embodiments, at least one pool comprises least two oligonucleotides of the same unique oligonucleotide species. In some embodiments, no pool comprises two oligonucleotides of the same unique oligonucleotide species. In some embodiments, the target specific region comprises an oligo dT sequence. In some embodiments, for each unique oligonucleotide species, the molecule barcode is 3' of the sample barcode. In some embodiments, for each unique oligonucleotide species, the sample barcode is 3' of the molecule barcode. In some embodiments, each unique oligonucleotide species has a length of at least 24 nucleotides. In some embodiments, each unique oligonucleotide species has a length of 24-140 nucleotides. In some embodiments, each pool comprises at least 6,500 unique oligonucleotide species. In some embodiments, each pool comprises at least 65,000 unique oligonucleotide species. In some embodiments, at least 48 unique samples are each contacted with a unique pool. In some embodiments, at least 99% of the samples comprise no more than one cell each. In some embodiments, the unique oligonucleotide species of each pool are immobilized on a substrate, so that the sample barcodes but not the molecule barcodes are the same for the unique oligonucleotide species immobilized on each substrate of the plurality. In some embodiments, the substrate comprises a spatially-isolated region of a surface, so that the substrates of different pools comprise the different spatially-isolated regions of the surface. In some embodiments, the substrate comprises a bead.

In some embodiments, each of the unique oligonucleotide species further comprises an adapter configured to immobilize the unique oligonucleotide on the substrate, wherein said barcode region is 3' of the adapter. In some embodiments, the uniform region comprises a target-specific region comprising a sequence flanking a sequence encoding the variable region of an immune cell receptor or immunoglobulin. In some embodiments, the variable region is of a T cell receptor or B cell receptor, or a combination thereof. In some embodiments, the method further comprises contacting the extended strands comprising an oligonucleotide of the unique oligonucleotide species and a sequence complementary to the target with primer configured to hybridize on an opposite side of the variable region as the target-specific region, and to hybridize to a complementary strand to a strand hybridized by the target-specific region. As such, the method can comprise amplifying sequences encoding variable regions of a T cell receptor, B cell receptor, or immunoglobulin. In some embodiments, the method amplifies a sequence of at least 1 kb, which comprises the variable region coding sequence.

Some embodiments include a method of making a composition comprising unique oligonucleotides is provided. The method can comprise providing a plurality of different sample barcodes comprising at least 3 nucleotides each. The method can comprise providing a plurality of different molecule barcodes comprising at least 7 nucleotides each. The methods can comprise synthesizing a plurality of unique oligonucleotide species, each unique oligonucleotide species comprising a barcode region comprising a sample barcode and a molecule barcode, in which at least one of: (a) the plurality of unique oligonucleotide species consists essentially of unique oligonucleotide species wherein each molecular barcode has a G content of less than 50%; or (b) the molecule barcodes of all of the unique oligonucleotide species in the plurality collectively have a G content of no more than 12.5%. The method can comprise disposing the unique oligonucleotide species in spatially-isolated pools, in which each pool comprises multiple unique oligonucleotide species, so that the unique oligonucleotide species of the same pool comprise the same sample barcode sequence, and wherein different unique oligonucleotide species of the same pool comprise different molecule barcode sequences, and in which each pool comprises at least 1000 unique oligonucleotide species. In some embodiments, ach unique oligonucleotide species further comprises a uniform region 3' of the barcode region. In some embodiments, the uniform region further comprises a target-specific region 3' of the barcode region, the target-specific region comprising at least 10 nucleotides complementary to a target nucleic acid. In some embodiments, the plurality of unique oligonucleotide species consists essentially of unique oligonucleotide species wherein each molecular barcode has a G content of less than 50%. In some embodiments, the molecule barcodes of all of the unique oligonucleotide species in the plurality collectively have a G content of no more than 12.5%. In some embodiments, each molecule barcode has a G content of 50% or less. In some embodiments, each sample barcode has a G content of 50% or less. In some embodiments, the sample barcodes of the unique oligonucleotide species collectively have a G content of no more than 12.5%. In some embodiments, the molecule barcodes of the unique oligonucleotide species collectively have a G content of less than 12.5%. In some embodiments, the barcode regions of the unique oligonucleotide species collectively have a G content of no more than 12.5%. In some embodiments, for at least 95% of the unique oligonucleotide species, any G in the molecule barcode is not adjacent to another G. In some embodiments, the plurality of the unique oligonucleotide species consists essentially of unique oligonucleotide species for which any G in the molecule barcode is not adjacent to another G. In some embodiments, at least 95% of the molecule barcodes of the unique oligonucleotide species comprise a sequence totaling at least 6 alternating H's and N's, wherein each "H" is any one of A, C, or T, and wherein each "N" is any one of A, G, C, or T. In some embodiments, at least 95% of the molecule barcodes of the unique oligonucleotides comprise the sequence HNHNHNHN, wherein each "H" is any one of A, C, or T, and wherein each "N" is any one of A, G, C, or T. In some embodiments, each molecule barcode of the unique oligonucleotides comprises the sequence HNHNHNHN, wherein each "H" is any one of A, C, or T, and wherein each "N" is any one of A, G, C, or T. In some embodiments, each molecule barcode of the unique oligonucleotides comprises the sequence HHHHHHHH, wherein each "H" is any one of A, C, or T. In some embodiments, each unique oligonucleotide species comprises a spacer 3' of the barcode region and 5' of the target specific region, said spacer comprising the sequence HNHNHNHN, wherein each "H" is any one of A, C, or T, and wherein each "N" is any one of A, G, C, or T. In some embodiments, each unique oligonucleotide species comprises a spacer 3' of the barcode region and 5' of the target specific region, said spacer comprising the sequence HHHHHHHH, wherein each "H" is any one of A, C, or T. In some embodiments, the target specific region comprises an oligo dT sequence. In some embodiments, for each unique oligonucleotide species, the molecule barcode is 3' of the sample barcode. In some embodiments, each unique oligonucleotide species, the sample barcode is 3' of the molecule barcode. In some embodiments, each unique oligonucleotide species has a length of at least 24 nucleotides. In some embodiments, each unique oligonucleotide species has a length of 24-140 nucleotides. In some embodiments, each pool comprises at least 6,500 unique oligonucleotide species. In some embodiments, each pool comprises at least 65,000 unique oligonucleotide species. In some embodiments, at least 48 pools are made. In some embodiments, the method further comprises immobililzing the unique oligonucleotide species of each pool onto a substrate, so that the sample barcodes but not the molecule barcodes are the same for the oligonucleotide species immobilized on each substrate of the plurality. In some embodiments, the substrates comprise discrete regions of a surface. In some embodiments, the substrates comprise beads. In some embodiments, the unique oligonucleotide species are disposed in spatially-isolated pools concurrent with said synthesis. In some embodiments, the unique oligonucleotide species are disposed in spatially-isolated pools after said synthesis. In some embodiments, the uniform region comprises a target-specific region comprising a sequence flanking a variable region coding sequence of an immune cell receptor or immunoglobulin. In some embodiments, the immune cell receptor variable region coding sequence is a T cell receptor variable region coding sequence, a B cell receptor variable region coding sequence, or a combination thereof. In some embodiments, the kit further comprising a primer configured to hybridize on an opposite side of the variable region coding sequence as the target-specific region, and to hybridize to a complementary strand to a strand hybridized by the target-specific region, and is thus configured, in conjunction with the target-specific region, to amplify the variable region coding sequence.

Some embodiments include an oligonucleotide comprising a barcode region 3' of the adapter region. The barcode region can comprise a molecule barcode comprising at least 7 nucleotides, in which the molecule barcode has a G content of no more than 50%. In some embodiments, the oligonucleotide further comprises a sample barcode comprising at least 3 nucleotides. In some embodiments, the oligonucleotide further comprises a uniform region 3' of the barcode region. In some embodiments, the uniform region comprises a target-specific region comprising at least 10 nucleotides complementary to a target nucleic acid. In some embodiments, the oligonucleotide further comprises an adapter region 5' of the barcode region. In some embodiments, the uniform region comprises a target-specific region comprising a sequence flanking a variable region coding sequence of an immune cell receptor or immunoglobulin. In some embodiments, the immune cell receptor variable region coding sequence is a T cell receptor variable region coding sequence, a B cell receptor variable region coding sequence, or a combination thereof. In some embodiments, the kit further comprising a primer configured to hybridize on an opposite side of the variable region coding sequence as the target-specific region, and to hybridize to a complementary strand to a strand hybridized by the target-specific region, and is thus configured to amplify the variable region coding sequence in conjunction with the target-specific region.

BRIEF DESCRIPTION OF THE DRAWINGS

FIGS. 3A-3H are diagrams illustrating a variety of configurations of oligonucleotide species in accordance with some embodiments herein. FIG. 3A illustrates a baseline oligonucleotide. FIG. 3B illustrates an oligonucleotide with a base spacer 3' of the barcode region. FIG. 3C illustrates an oligonucleotide with a 5-base spacer 3' of the barcode region. FIG. 3D illustrates an oligonucleotide in which the positions of the molecule barcode (indicated as "NNNNNNNN") and the sample barcode within the barcode region are switched in comparison to FIG. 3A, so that the molecule barcode is 5' of the sample barcode. FIG. 3E illustrates an oligonucleotide in which the positions of the molecule barcode (indicated as "NNNNNNNN") and the sample barcode within the barcode region are switched in comparison to FIG. 3A, so that the molecule barcode is 5' of the sample barcode, and including a 3-base spacer. FIG. 3F illustrates an oligonucleotide in which the positions of the molecule barcode (indicated as "NNNNNNNN") and the sample barcode within the barcode region are switched, so that the molecule barcode is 5' of the sample barcode, and including a 5-base spacer. FIG. 3G illustrates an oligonucleotide in which the molecule barcode comprises the sequence HHHHHHHH (in which each H is an A, C, or T, and in which each H can be the same or different from any other H). FIG. 3H illustrates an oligonucleotide in which the molecule barcode comprises the sequence HNHNHNHN (in which each H is an A, C, or T, and in which each H can be the same or different from any other H).

FIG. 5A is a diagram illustrating nucleic acid sequences of oligonucleotide species that were constructed in accordance with some embodiments herein. The indicated SEQ ID NOs: in the right-most columns of FIGS. 5A-5D refer to the polynucleotide sequence that includes the "anchor," "1st bc," "2nd bc," "Spacer" (if any), and "5 to 3' Recognition Sequence" as shown. Each "anchor" in FIGS. 5A-5D has the polynucleotide sequence of SEQ ID NO: 97.

FIG. 5B is a diagram illustrating nucleic acid sequences of oligonucleotide species that were constructed in accordance with some embodiments herein.

FIG. 5C is a diagram illustrating nucleic acid sequences of oligonucleotide species that were constructed in accordance with some embodiments herein.

FIG. 5D is a diagram illustrating nucleic acid sequences of oligonucleotide species that were constructed in accordance with some embodiments herein.

DETAILED DESCRIPTION

Figure 8:
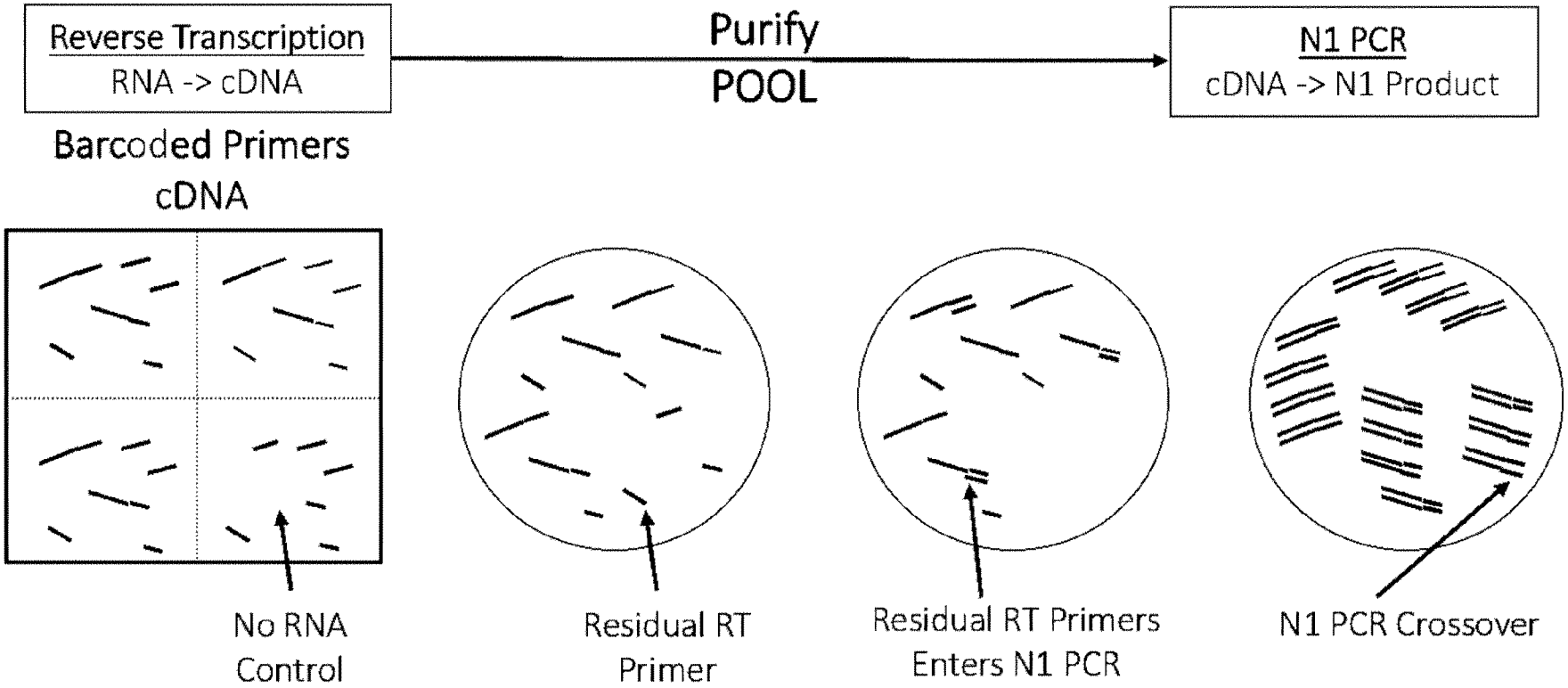
FIG. 8 is a diagram schematically illustrating, without being limited by any theory, possible amplification errors that can result from oligonucleotides with high G-contents.

In accordance with some embodiments herein, methods and compositions for accurate barcoding and analysis of nucleic acids are described. In some embodiments, individual nucleic acids of a sample can be associated with a unique barcode (e.g. a "molecule barcode"), so that upon amplification and sequence analysis, individual nucleic acids of a sample can be quantified. Without being limited by any theory, it is contemplated that bias favoring or disfavoring the representation, amplification, or properties of certain kinds of barcode sequences can interference with quantification and analysis of the individual nucleic acids of a sample (possible sources of bias in some amplification events are schematically illustrated in FIG. 8). Described in accordance with some embodiments herein are configurations and characteristics of unique oligonucleotide species comprising barcodes, in which the unique oligonucleotide species are configured to minimize barcode-related bias, and yield accurate analysis of nucleic acids. Without being limited by any theory, it is contemplated that barcode regions comprising features such as a guanosine (G) content below 50%, and/or no two consecutive "G's" in the barcode region can minimize bias that could otherwise confound quantification and/or analysis of nucleic acids of a sample. Optionally, the individual nucleic acid molecules of a given sample can also be associated with a "sample barcode", so that barcode-associated nucleic acids can be subsequently pooled for an efficient batch analysis of nucleic acids from two or more samples, for example by next-generation sequencing.

Nucleic Aids

Various nucleic acids are described in accordance with some embodiments herein. For example, oligonucleotide species, samples, and/or targets can comprise nucleic acids.

As used herein, a "nucleic acid" refers to a polynucleotide sequence, or fragment thereof. A nucleic acid can comprise nucleotides. A nucleic acid can be exogenous or endogenous to a cell. A nucleic acid can exist in a cell-free environment. A nucleic acid can comprise, consist of, or consist essentially of a gene or fragment thereof. A nucleic acid can comprise, consist of, or consist essentially of DNA. A nucleic acid can comprise, consist of, or consist essentially of RNA. A nucleic acid can comprise one or more analogs (e.g. altered backgone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, florophores (e.g. rhodamine or flurescein linked to the sugar), thiol containing nucleotides, biotin linked nucleotides, fluorescent base analogs, CpG islands, methyl-7-guanosine, methylated nucleotides, inosine, thiouridine, pseudourdine, dihydrouridine, queuosine, and wyosine. "Nucleic acid", "polynucleotide," "target polynucleotide", and "target nucleic acid" can be used interchangeably.

Figure 2A:
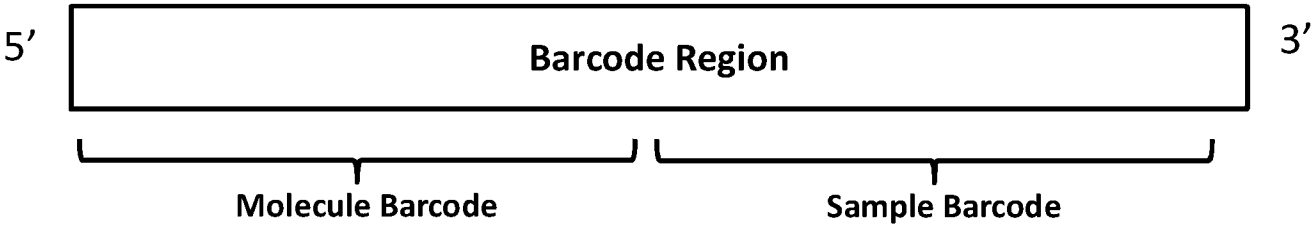
FIG. 2A is a schematic diagram illustrating a barcode region comprising a molecule barcode 5' of a sample barcode, and which can comprise a barcode region of a unique oligonucleotide species in accordance with some embodiments herein.
Figure 2B:
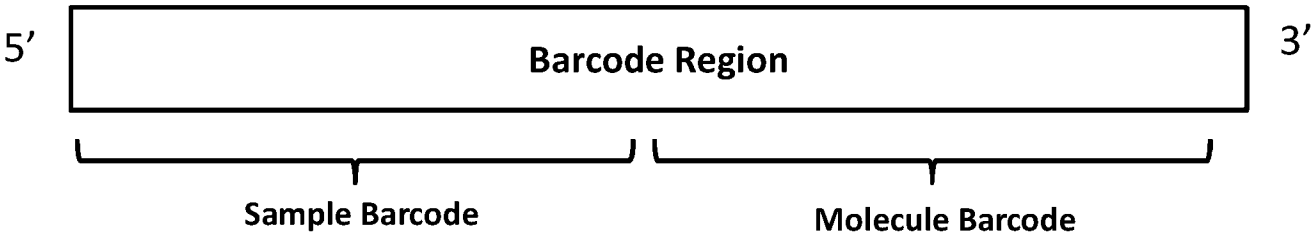
FIG. 2B is a schematic diagram illustrating a barcode region comprising a sample barcode 5' of a molecule barcode, and which can comprise a barcode region of a unique oligonucleotide species in accordance with some embodiments herein.

As used herein, "upstream" (and variations of this root term) refers to a position that is relatively 5' on a nucleic acid (e.g., 5' in comparison to reference position). As used herein "downstream" (and variations of this root term) refers to a position that is relatively 3' on a nucleic acid (e.g., 3' in comparison to reference position). For example, as shown in FIG. 2A, the "sample barcode" is 3' of the "molecule barcode" and is understood to be downstream of the molecule "barcode." For example, as shown in FIG. 2B, the "sample barcode" is 5' of the "molecule barcode" and is understood to be upstream of the molecule "barcode."

A nucleic acid can comprise one or more modifications (e.g., a base modification, a backbone modification), to provide the nucleic acid with a new or enhanced feature (e.g., improved stability). A nucleic acid can comprise a nucleic acid affinity tag. A nucleoside can comprise, consist of, or consist essentially of a base-sugar combination. The base portion of the nucleoside can be a heterocyclic base. The two most common classes of such heterocyclic bases are the purines and the pyrimidines. Nucleotides can comprise, consist of, or consist essentially of nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming nucleic acids, the phosphate groups can covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within nucleic acids, the phosphate groups can commonly be referred to as forming the internucleoside backbone of the nucleic acid. The linkage or backbone of the nucleic acid can be a 3' to 5' phosphodiester linkage.

A nucleic acid can comprise a modified backbone and/or modified internucleoside linkages. Modified backbones can include those that retain a phosphorus atom in the backbone and those that do not have a phosphorus atom in the backbone. Suitable modified nucleic acid backbones containing a phosphorus atom therein can include, for example, phosphorothioates, chiral phosphorothioates, phosphorodithioates, phosphotriesters, aminoalkylphosphotriesters, methyl and other alkyl phosphonates such as 3'-alkylene phosphonates, 5'-alkylene phosphonates, chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage.

A nucleic acid can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

A nucleic acid can comprise a nucleic acid mimetic. The term "mimetic" includes, for example, polynucleotides wherein only the furanose ring or both the furanose ring and the internucleotide linkage are replaced with non-furanose groups, replacement of only the furanose ring can also be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A nucleic acid can comprise a morpholino backbone structure. For example, a nucleic acid can comprise a 6-membered morpholino ring in place of a ribose ring. In some of these embodiments, a phosphorodiamidate or other non-phosphodiester internucleoside linkage can replace a phosphodiester linkage.

A nucleic acid can comprise linked morpholino units (i.e. morpholino nucleic acid) having heterocyclic bases attached to the morpholino ring. Linking groups can link the morpholino monomeric units in a morpholino nucleic acid. Non-ionic morpholino-based oligomeric compounds can have less undesired interactions with cellular proteins. Morpholino-based polynucleotides can be nonionic mimics of nucleic acids. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can comprise, consist of, or consist essentially of a methylene (—CH2-), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties.

A nucleic acid can also, in some embodiments, include nucleobase (often referred to simply as "base") modifications or substitutions. As used herein, "unmodified" or "natural" nucleobases can include the purine bases, (e.g. adenine (A) and guanine (G)), and the pyrimidine bases, (e.g. thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C═C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4) benzoxazin-2(3H)-one), carbazole cytidine (2H-pyrimido(4,5-b)indol-2-one), pyridoindole cytidine (Hpyrido(3',4,5)pyrrolo[2,3-d]pyrimidin-2-one).

Samples

As used herein, the term "sample" refers to a composition comprising targets. Suitable samples for analysis by the disclosed methods, devices, and systems include, but are not limited to, cells, single cells, tissues, organs, or organisms. In some embodiments, a sample comprises raw or unprocessed samples, for example a whole cell, whole population of cells, or whole tissue. In some embodiments, a sample comprises an isolated cell or cell extract, or a nucleic-acid-containing fraction thereof, for example isolated nucleic acids, or a composition comprising enriched or isolated nucleic acids. In some embodiments, a sample comprises a fixed tissue, cell, or nucleic-acid-containing fraction thereof. In some embodiments, a sample comprises a frozen tissue, cell, or nucleic-acid-containing fraction thereof. In some embodiments, a sample comprises a solution comprising nucleic acids. In some embodiments, a sample comprises a solution comprising nucleic acids. In some embodiments, a sample comprises nucleic acids in a solid format, for example lyophilized nucleic acids and the like.

Unique Oligonucleotide Species

As used in compositions, methods, and oligonucleotides in accordance with some embodiments herein, a "unique oligonucleotide species" refers to an oligonucleotide, for example DNA or RNA, having a sequence that differs by at least one base from another unique oligonucleotide species. The unique oligonucleotide species of a composition in accordance with some embodiments herein can share certain structural features or formats, but can have different nucleic acid sequences from each other. The unique oligonucleotide species can be single-stranded or double-standed. A composition can comprise two or more unique oligonucleotide species, for example a diversity of 100, 1000, 6500, or 65,000 unique oligonucleotide species. Optionally, the composition comprising unique oligonucleotide species can also comprise two or more oligonucleotides of the same unique oligonucleotide species. By way of example a composition can comprise two unique oligonucleotide species: ACTT-X and TCTT-X, in which "X" is a sequence that is the same for both unique oligonucleotide species. It would be possible for the composition to comprise two copies of an oligonucleotide having the sequence ACTT-X, and one copy of an oligonucleotide having the sequence TCTT-X.

The oligonucleotide species of the compositions, methods, and oligonucleotides of some embodiments herein can comprise a barcode region and a uniform region as described herein. The barcode regions can differ between unique oligonucleotide species, so as to provide diversity in a population of unique oligonucleotide species, while the uniform regions remain the same. The barcode region can comprise a molecule index as described herein. The molecule index can be configured to minimize bias, for example by minimizing G content so that no unique oligonucleotide species in a population of unique oligonucleotide species has a molecule index with a G content greater than 50%, and/or so that the sequence "GG" does not appear in the molecule index (e.g. so that there are no two consecutive G's). Optionally, the barcode region comprises a sample index. The sample index can be configured so that the unique oligonucleotides of a given pool can have the same sample index, but different molecule indices. As such, if multiple samples are analyzed, the sample index can indicate which sample each oligonucleotide corresponds to. As such, after unique oligonucleotide species bind to target, the unique oligonucleotide species can be pooled, and sequences can be analyzed. In some embodiments, the sample index is 5' of the molecule index. In some embodiments, the molecule index is 5' of the sample index. Optionally, the unique oligonucleotide species comprises an adapter. The adapter can be positioned 5' of the barcode region. In some embodiments, the adapter is configured to immobilize the unique oligonucleotide species on a substrate.

Without being limited by any theory, it is contemplated that unique oligonucleotides species configured in accordance with some embodiments herein can yield accurate analysis and sequencing results with reduced, minimal, or no bias, for example by minimizing G content in the molecule barcode or barcode region, and/or minimizing G content near the uniform region. By way of example, a reduction in bias can be ascertained by a reduction in noise and/or an increase in sensitivity for detecting the number of different molecules of a target nucleic acid in a sample (see, e.g. FIGS. 6-7). In some embodiments, the reduction in bias can be ascertained as a decrease in noise (see FIG. 6), for example a smaller standard error in the number of target nucleic acid molecules detected in the sample. In some embodiments, the reduction in bias can be ascertained as an increase in sensitivity (see FIG. 7), for example detecting a larger number of the different molecules of a target nucleic acid in a sample (e.g. fewer target nucleic acid molecules are "missed". As such, in some embodiments, compositions and methods yield quantification of target nucleic acid molecules in a sample with low noise, for example a relative standard error less than 30%, for example, less than 30%, 25%, 20%, 15%, 10%, 5%, 4%, 3%, 2%, 1%, or 0.01%, including ranges beween any two of the listed values. In some embodiments, compositions and methods yield quantification of target nucleic acid molecules in a sample with high sensitivity, for example a sensitivity (measured as a percent of the actual number of different target nucleic acids in a sample that are detected), for example, a sensitivity of at least 70%, 75%, 80%, 85%, 90%, 85%, 96%, 97%, 98%, 99%, or 99.9%, including ranges between any two of the listed values. In some embodiments, the methods or compositions described herein reduce bias by increasing sensitivity, decreasing relative standard error, or increasing sensitivity and reducing standard error relative to compositions or methods comprising unique oligonucleotide species in line with FIG. 3A.

FIG. 3A illustrates a conventional oligonucleotide design. It is noted that the molecule index sequence NNNNNNNN (in which each N is A, G, C, or T, and in which any two of the N's can be the same or different from each other) can comprise two or more consecutive G's, and/or can have a G content greater than 50%. For example, a subset of the population of unique oligonucleotide species in line with FIG. 3A can be G-rich. Without being limited by any theory, it is contemplated that at least some unique oligonucleotide species in a population based on the configuration of FIG. 3A could be favored, leading to bias. Another example of "baseline" molecule index that can be subject to bias is the sequence 'BBBBBBV' (in which B is C, G, or T, and in which V is A, C, or G). Examples of configurations for unique oligonucleotide species in accordance with some embodiments herein are illustrated in FIGS. 3B-3H. As shown in FIGS. 3B-C, addition of either TTT or TTTTT after the molecule index in accordance with some embodiments herein can reduce G-richness along the region (the length of non-G spacers can be variable, and can comprise any non-G nucleotide or nucleotides). In FIG. 3D, the sample index and molecule positions are switched (so that the molecule index is 5' of the sample index), so that possible high G-rich MIs in at least a subset of unique oligonucleotide species would not be adjacent to potentially G-rich gene specific target regions. In FIGS. 3E-F, addition of either TTT or TTTTT to the configuration illustrated in FIG. 3D can further minimize potential G-rich regions. Without being limited by any theory, it is noted that that sample barcodes frequently can have low G contents (e.g. so as to be "non-G-rich"). It is further noted that the length of non-G spacers can be variable and can be any non-G nucleotide). In the configurations of FIGS. 3G-H, molecule barcodes comprise 'HHHHHHHH' or 'HNHNHNHN,' (in which H is A, C, or T, and in which any two H's can be the same or different from each other, and in which any two N's can be the same or different from each other).

In some embodiments, each of a plurality of unique oligonucleotide species (e.g., each of the unique oligonucleotide species) in a composition or method has a length of at least 24 nucleotides, for example at least 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 60, 65, 70, 75, 80, 85, 90, 95, 100, 105, 110, 115, 120, 125, 130, 135, or 140 nucleotides in length, including ranges between any two of the listed values, for example 24-140, 24-135, 24-130, 24-125, 24-120, 24-115, 24-110, 24-105, 24-100, 24-95, 24-90, 24-85, 24-80, 24-75, 24-70, 24-65, 24-60, 24-55, 24-50, 24-45, 24-40, 25-140, 25-135, 25-130, 25-125, 25-120, 25-115, 25-110, 25-105, 25-100, 25-95, 25-90, 25-85, 25-80, 25-75, 25-70, 25-65, 25-60, 25-55, 25-50, 25-45, 25-40, 27-140, 27-135, 27-130, 27-125, 27-120, 27-115, 27-110, 27-105, 27-100, 27-95, 27-90, 27-85, 27-80, 27-75, 27-70, 27-65, 27-60, 27-55, 27-50, 27-45, 27-40, 30-140, 30-135, 30-130, 30-125, 30-120, 30-115, 30-110, 30-105, 30-100, 30-95, 30-90, 30-85, 30-80, 30-75, 30-70, 30-65, 30-60, 30-55, 30-50, 30-45, 30-40, 35-140, 35-135, 35-130, 35-125, 35-120, 35-115, 35-110, 35-105, 35-100, 35-95, 35-90, 35-85, 35-80, 35-75, 35-70, 35-65, 35-60, 35-55, 35-50, 35-45, 35-40, 40-140, 40-135, 40-130, 40-125, 40-120, 40-115, 40-110, 40-105, 40-100, 40-95, 40-90, 40-85, 40-80, 40-75, 40-70, 40-65, 40-60, 40-55, 40-50, or 40-45 nucleotides in length. Optionally, different unique oligonucleotide species in a composition or method have different lengths form each other. Optionally, all of the unique oligonucleotide species in a composition or method have the same length as each other. Optionally, some unique oligonucleotide species in a composition or method are the same length as each other, while some unique oligonucleotide species are different lengths from each other.

In some embodiments, the uniform region comprises, consists of, or consists essentially of a 5' to 3' amplification sequence for a target nucleic acid, or class of target nucleic acids (this amplification sequence may also be referred to as a "target-specific" region). For example, if the target nucleic acids comprise mRNAs, the uniform region can comprise oligo dT. For example, if the target nucleic acids comprise variable regions of a T cell receptor, the uniform region can comprise sequences flanking variable regions of a T cell receptor mRNA. In some embodiments, the uniform region comprises at least 10 nucleotides that are complementary to the target nucleic acid, for example at least 10, 11, 12, 13, 14, 15, 16, 17, 18, 19, 20, 21, 22, 23, 24, 25, 26, 27, 28, 29, or 30 nucleotides complementary to the target, including ranges between any two of the listed values, for example 10-30, 10-29, 10-28, 10-27, 10-26, 10-25, 10-24, 10-23, 10-22, 10-21, 10-20, 11-30, 11-29, 11-28, 11-27, 11-26, 11-25, 11-24, 11-23, 11-22, 11-21, 11-20, 12-30, 12-29, 12-28, 12-27, 12-26, 12-25, 12-24, 12-23, 12-22, 12-21, 12-20, 15-30, 15-29, 15-28, 15-27, 15-26, 15-25, 15-24, 15-23, 15-22, 15-21, 15-20, 20-30, 20-29, 20-28, 20-27, 20-26, 20-25, 20-24, 20-23, 20-22, or 20-21 nucleotides. In some embodiments, the uniform region comprises a target-specific region that hybridizes to a sequence flanking a sequence encoding a variable region of an immune cell receptor, for example a variable region of a T cell receptor, a B cell receptor, or immunoglobulin, for example an antibody. It is noted that because B cell receptors comprise membrane-bound immunoglobulin, target-specific regions specific for immunoglobulin variable region coding sequences are typically suitable for amplifying B cell receptors as well as secreted immunoglobulins (e.g. antibodies). Both options are noted herein to clarify that amplification of membrane-bound immunoglobulins (B cell receptors) and also secreted immunoglobulins (antibodies) is contemplated. As used herein, it will be understood that when primers or uniform regions comprise target-specific regions that comprise "flanking sequences" (and variations of this root term, such as "sequences flanking") of immune cell receptor and/or immunoglobulin variable regions, the target-specific regions will be understood to comprise at least one of (i) sequences that hybridize downstream (3') of the sequence encoding the variable region and in particular hybridize to strand of the coding sequence, and thus are configured to produce a strand comprising the reverse complement of the variable region coding sequence upon extension in the 5' to 3' direction; or (ii) sequences that hybridize upstream (5') of the sequence encoding the variable region and in particular hybridize to the strand complementary to that of the coding sequence, and thus are configured to produce a strand comprising the variable region coding sequence upon extension in the 5' to 3' direction. Thus, a flanking sequence can be configured for amplification of the variable region coding sequences in conjunction with a suitable priming partner (e.g. a flanking sequence on the other side of the variable region). It will be understood that a flanking sequences does not necessarily need to stop or start exactly where the coding sequence starts or stops, and thus, it is permissible for there to be intervening sequences between a hybridization site of a flanking sequence and the variable region coding sequence itself. It will be understood that while a flanking sequence will generally hybridize to a sequence outside of the variable region coding sequence so as to amplify a broad range of possible variable region coding sequences, in some embodiments, the variable region "flanking sequence" further comprises some sequence of the variable region itself, for example if a subset of possible variable regions is of interest. However, a "flanking sequence" as used herein does not require a single sequence to flank both sides of the variable region. Rather, it will be understood that when flanking sequences are mentioned in conjunction with compositions, methods, and oligonucleotides of some embodiments herein, 5' and 3' sequences comprising suitable primer pairs to amplify the variable region coding sequence are also expressly contemplated.

In some embodiments, a unique oligonucleotide species comprises a barcode region as described herein and also comprises a uniform region comprising a target-specific region comprising a sequence flanking an immune cell receptor and/or immunoglobulin variable region coding sequence. A second oligonucleotide primer can also be provided for the other side of the variable region coding sequence, so as to amplify the variable region sequence in conjunction with the target-specific region of the uniform region. In some embodiments, the uniform region comprises a target-specific region, positioned 3' of the barcode region, and comprising a sequence flanking an immunoglobulin variable region (and thus flanking a B cell receptor variable region as well as a corresponding antibody variable region), for example flanking the variable region of an immunoglobulin heavy chain locus, flanking the variable region of an immunoglobulin (light chain) kappa locus, or flanking the variable region of an immunoglobulin (light chain) lambda locus. In some embodiments, the uniform region comprises a target-specific region, positioned 3' of the barcode region, and comprising a sequence flanking at least one of a variable region of a T cell receptor alpha chain, a variable region of a T cell receptor beta chain, a variable region of a T cell receptor gamma chain, or a T cell receptor delta chain.

In some embodiments, a kit comprises a composition comprising unique oligonucleotide species as described herein, in which the unique oligonucleotide species each comprise a uniform sequence flanking an immune cell receptor or immunoglobulin variable region coding sequence as described herein. In some embodiments, the kit further comprises an oligonucleotide primer configured to hybridize to the opposite strand and on the other side of the variable region coding sequence compared to the uniform region, and is thus configured to amplify the variable region sequence in conjunction with the target-specific region of the uniform region. In some embodiments, the amplified sequence is at least 1 kb and comprises the variable coding sequence, for example at least 1 kb, 2 kb, 3 kb, 4 kb, or 5 kb, including ranges between any two of the listed values.

It is noted the nucleic acids encoding variable regions of some immune cell receptors or immunoglobulins can be more than 1 kb long. For example, T cell receptor variable region sequences can comprise a CDR3 coding sequence that ends more than 1 kb away from where the CDR1 coding sequence begins. Without being limited by theory, it is noted that some conventional and next-generation sequencing approaches, for example sequencing by synthesis, are limited to short reads that are typically considerably less than 1 kb. Accordingly, it is contemplated that methods and compositions and kits in accordance with some embodiments herein can be useful for barcoding and analyzing nucleic acids encoding immune cell receptor and/or immunoglobulin variable regions, which otherwise would not be amenable to single-read sequencing of less than 1 kb. Accordingly, in some embodiments, the unique oligonucleotide species comprises a sequence flanking an immune cell receptor or immunoglobulin variable region coding sequence, is configured to amplify a sequence of at least 1 kb and comprising the variable region coding sequence, for example at least 1 kb, 2 kb, 3 kb, 4 kb, or 5 kb, including ranges between any two of the listed values.

Barcode Regions

In accordance with compositions, methods, and oligonucleotides of some embodiments herein, a barcode region comprises a nucleic acid sequence that is useful in identifying a nucleic acid, for example a target nucleic acid from a sample, or an amplicon or reverse-transcript derived from a single target nucleic acid of a sample. For example, two mRNA transcripts from a sample can be reverse-transcribed and barcoded so that nucleic acids corresponding to the first mRNA comprise a first barcode, and nucleic acids corresponding to the second mRNA comprise a second barcode. Upon sequencing (or other analysis), information about the individual mRNAs in the sample, for example copy number can be ascertained even after amplification. However, if a large population of mRNAs is stochastically labeled and some barcodes are represented more favorably (for example due to stability, amplification efficiency, etc.), bias can result, skewing the ability to quantify nucleic acids of a sample. As such, in accordance with some embodiments herein, each unique oligonucleotide species in a population can comprise a unique barcode region. The greater the diversity of barcodes, the greater the diversity of unique oligonucleotide species, and the greater the probability that a particular barcode sequence will be associated with only one target nucleic acid of a sample. The barcode region can be, for example, positioned 5' of a uniform region on an oligonucleotide species. In some embodiments, a barcode region comprises a molecule barcode as described herein. Optionally, a barcode region comprises a molecule barcode and a sample barcode as described herein. Optionally, a barcode region comprises a molecule barcode 5' of a sample barcode. In some embodiments, methods or compositions comprising unique oligonucleotide species comprising molecule barcodes as described herein reduce bias by increasing sensitivity, decreasing relative standard error, or increasing sensitivity and reducing standard error. As used herein, a "molecule barcode" can also be referred to as a "molecular barcode," "Molecular Index (MI)", or Unique Molecular Identifier (UMI). As used herein, a "sample barcode," can also be referred to as a "Sample Index (SI)."

A barcode region can comprise a molecule barcode. The molecule barcode can comprise a unique sequence, so that when multiple sample nucleic acids (which can be the same and/or different from each other) are associated one-to-one with molecule barcodes, different sample nucleic acids can differentiated from each other by the molecule barcodes. As such, even if a sample comprises two nucleic acids having the same sequence, each of these two nucleic acids can be labeled with a different molecule barcode, so that nucleic acids in the population can be quantified, even after amplification. The molecule barcode can comprise a nucleic acid sequence of at least 5 nucleotides, for example at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides, including ranges between any two of the listed values, for example 5-50, 5-45, 5-40, 5-35, 5-30, 5-25, 5-20, 5-15, 5-14, 5-13, 5-12, 5-11, 5-10, 5-9, 5-8, 5-7, 5-6, 6-50, 6-45, 6-40, 6-35, 6-30, 6-25, 6-20, 6-15, 6-14, 6-13, 6-12, 6-11, 6-10, 6-9, 6-8, 6-7, 7-50, 7-45, 7-40, 7-35, 7-30, 7-25, 7-20, 7-15, 7-14, 7-13, 7-12, 7-11, 7-10, 7-9, 7-8, 8-50, 8-45, 8-40, 8-35, 8-30, 8-25, 8-20, 8-15, 8-14, 8-13, 8-12, 8-11, 8-10, 8-9, 9-50, 9-45, 9-40, 9-35, 9-30, 9-25, 9-20, 9-15, 9-14, 9-13, 9-12, 9-11, 9-10, 10-50, 10-45, 10-40, 10-35, 10-30, 10-25, 10-20, 10-15, 10-14, 10-13, 10-12, or 10-11 nucleotides. In some embodiments, the nucleic acid sequence of the molecule barcode comprises a unique sequence, for example, so that each unique oligonucleotide species in a composition comprises a different molecule barcode. In some embodiments, two or more unique oligonucleotide species can comprise the same molecule barcode, but still differ from each other. For example, if the unique oligonucleotide species include sample barcodes, each unique oligonucleotide species with a particular sample barcode can comprise a different molecule barcode. In some embodiments, a composition comprising unique oligonucleotide species comprises a molecule barcode diversity of at least 1000 different molecule barcodes, and thus at least 1000 unique oligonucleotide species. In some embodiments, a composition comprising unique oligonucleotide species comprises a molecule barcode diversity of at least 6,500 different molecule barcodes, and thus at least 6,500 unique oligonucleotide species. In some embodiments, a composition comprising unique oligonucleotide species comprises a molecule barcode diversity of at least 65,000 different molecule barcodes, and thus at least 65,000 unique oligonucleotide species.

Figure 4A:
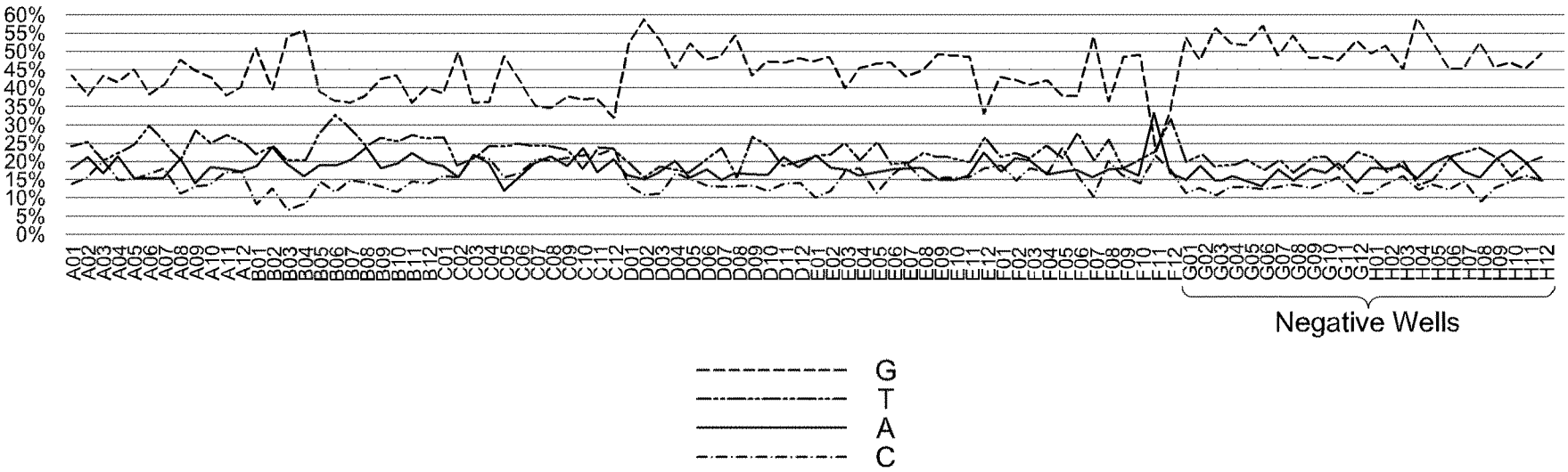
FIG. 4A is a diagram illustrating nucleotide usage in a sampling of conventional unique oligonucleotide species.
Figure 4B:
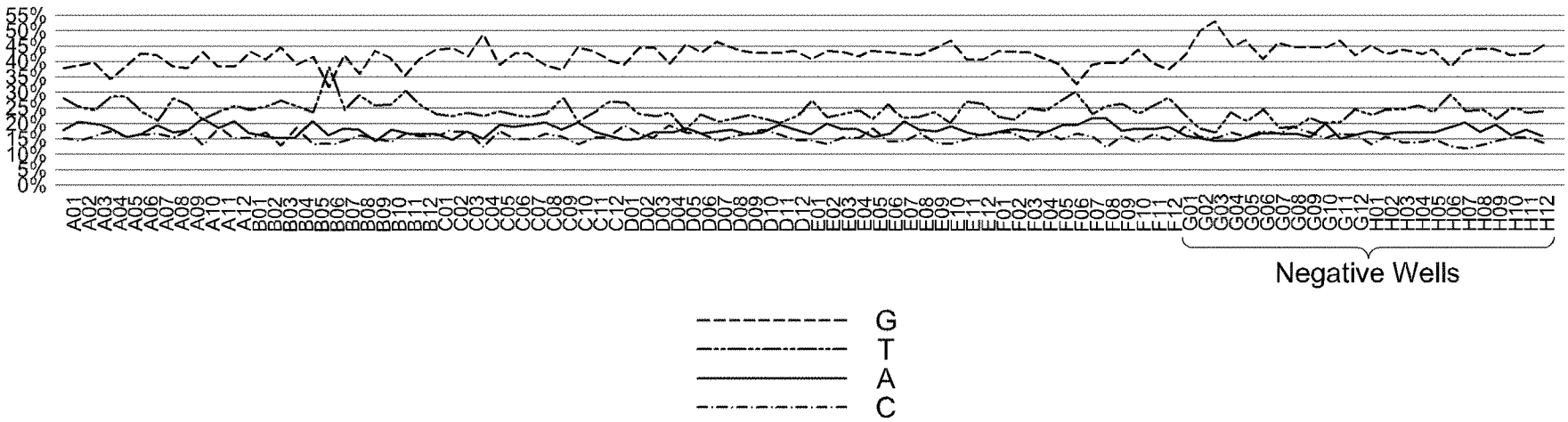
FIG. 4B is a diagram illustrating nucleotide usage in a sampling of conventional unique oligonucleotide species.
Figure 4C:
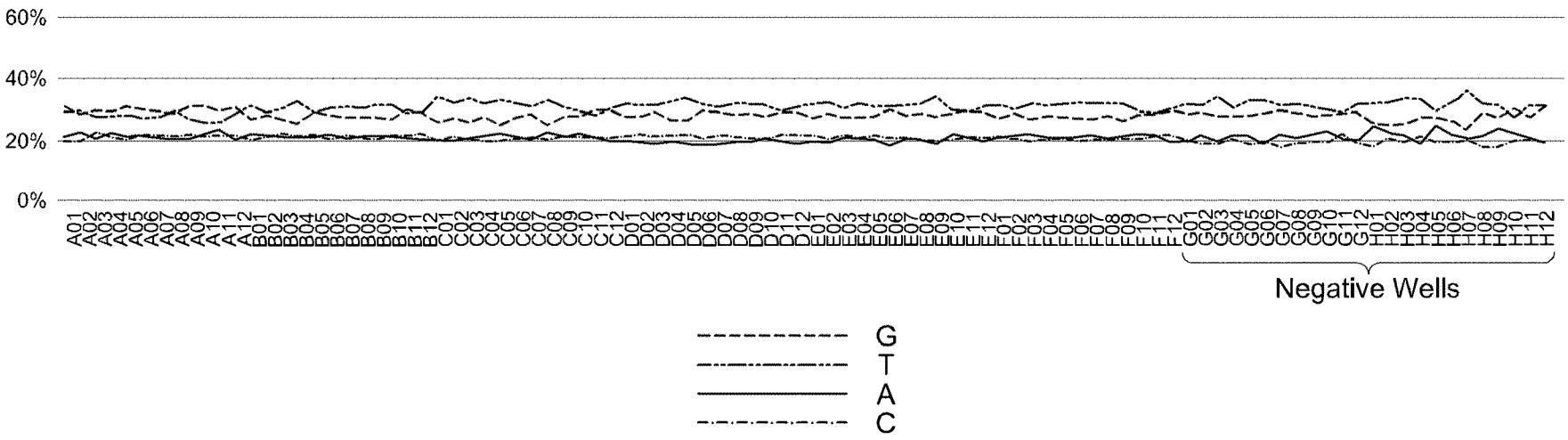
FIG. 4C is a diagram illustrating nucleotide usage in a sampling of conventional unique oligonucleotide species.

Without being limited by any theory, it is contemplated that a molecule barcode comprising a low G content (e.g., 50% G or less, for example, less than 50% G, 45% G, 40% G, 35% G, 30% G, 25% G, 20% G, 15% G, 12.5% G, 10% G, 7.5% G, 5% G, or 2.5% G) can minimize bias for a composition or pool of unique oligonucleotide species being used to barcode a population of nucleic acids (e.g. minimize bias that would preferentially amplify barcodes comprising a higher G content). It is noted that conventional barcoding approaches typically exhibit a bias in favor of higher G content. For example FIGS. 4A, 4B, and 4C illustrate samples of nucleotide usage in conventional molecule barcodes of compositions comprising numerous unique molecule barcodes for ES32, TRAC (FIG. 4A), ES32 TRBC (FIG. 4B), and ES32 OligodT (FIG. 4C). That is, if anything, conventional molecule barcodes and barcode regions, designed without respect to certain guidance provided herein, can comprise a higher G-content that would be expected by random chance. In some embodiments, methods or compositions comprising unique oligonucleotide species comprising molecule barcodes as described herein reduce bias by increasing sensitivity, decreasing relative standard error, or increasing sensitivity and reducing standard error.

In some embodiments, all of the molecule barcodes of a composition or composition used in the methods described herein comprise unique oligonucleotide species collectively have a G content of 50% G or less, for example, less than 50% G, 45% G, 40% G, 35% G, 30% G, 25% G, 20% G, 15% G, 12.5% G, 10% G, 7.5% G, 5% G, or 2.5% G, or 0% G, including ranges between any two of the listed values, for example 2.5-50% G, 2.5-45% G, 2.5-40% G, 2.5-35% G, 2.5-30% G, 2.5-25% G, 2.5-20% G, 2.5-15% G, 2.5-10% G, 2.5-7.5% G, 2.5-5% G, 5-50% G, 5-45% G, 5-40% G, 5-35% G, 5-30% G, 5-25% G, 5-20% G, 5-15% G, 5-10% G, 5-7.5% G, 7.5-50% G, 7.5-45% G, 7.5-40% G, 7.5-35% G, 7.5-30% G, 7.5-25% G, 7.5-20% G, 7.5-15% G, 7.5-10% G, 10-50% G, 10-45% G, 10-40% G, 10-35% G, 10-30% G, 10-25% G, 10-20% G, 10-15% G, 10-12.5% a G, 12.5-50% G, 12.5-45% G, 12.5-40% G, 12.5-35% G, 12.5-30% G, 12.5-25% G, 12.5-20% G, 12.5-15% G, 15-50% G, 15-45% G, 15-40% G, 15-35% G, 15-30% G, 15-25% G, 15-20% G, 20-50% G, 20-45% G, 20-40% G, 20-35% G, 20-30% G, or 20-25% G. By "all of the molecule barcodes of a composition of unique oligonucleotide species collectively have a G content of . . . ", it is meant that if the total G content among all of molecule barcodes in the whole composition was calculated (e.g., a population of at least 10, 50, 100, 200, 500, 1000, 2000, 5000, 6500, 10,000, 20,000, 30,000, 40,000, 50,000, 60,000, or 65,000 unique oligonucleotide species), this total G content of the sum total of the barcodes would fall below the recited values or within the recited ranges. While it would still be possible for an individual unique oligonucleotide species to have a molecule barcode with a G content above the indicated value or outside the indicated range, the collective nucleotide content of the unique oligonucleotide species of the composition would be below the indicated value or within the indicated range. In some embodiments, all of the molecule barcodes in a composition comprising at least 1000 unique oligonucleotide species collectively have a G content of 50% G or less, for example, less than 50% G, 45% G, 40% G, 35% G, 30% G, 25% G, 20% G, 15% G, 12.5% G, 10% G, 7.5% G, 5% G, or 2.5% G, or 0% G, including ranges between any two of the listed values. In some embodiments, all of the molecule barcodes in a composition comprising at least 6500 unique oligonucleotide species collectively have a G content of 50% G or less, for example, less than 50% G, 45% G, 40% G, 35% G, 30% G, 25% G, 20% G, 15% G, 12.5% G, 10% G, 7.5% G, 5% G, or 2.5% G, or 0% G, including ranges between any two of the listed values. In some embodiments, all of the molecule barcodes in a composition comprising at least 65,000 unique oligonucleotide species collectively have a G content of 50% G or less, for example, less than 50% G, 45% G, 40% G, 35% G, 30% G, 25% G, 20% G, 15% G, 12.5% G, 10% G, 7.5% G, 5% G, or 2.5% G, or 0% G, including ranges between any two of the listed values. In some embodiments, all of the barcode regions of the composition as described herein collectively have a G content of less than 50% as described herein.

In some embodiments, for a composition comprising unique oligonucleotide species (or such a composition used in a method), the composition consists of or consists essentially of unique oligonucleotide species that each comprise a molecule barcode G content of 50% G or less, for example, less than 50% G, 45% G, 40% G, 35% G, 30% G, 25% G, 20% G, 15% G, 12.5% G, 10% G, 7.5% G, 5% G, or 2.5% G, or 0% G, including ranges between any two of the listed values, for example 2.5-50% G, 2.5-45% G, 2.5-40% G, 2.5-35% G, 2.5-30% G, 2.5-25% G, 2.5-20% G, 2.5-15% G, 2.5-10% G, 2.5-7.5% G, 2.5-5% G, 5-50% G, 5-45% G, 5-40% G, 5-35% G, 5-30% G, 5-25% G, 5-20% G, 5-15% G, 5-10% G, 5-7.5% G, 7.5-50% G, 7.5-45% G, 7.5-40% G, 7.5-35% G, 7.5-30% G, 7.5-25% G, 7.5-20% G, 7.5-15% G, 7.5-10% G, 10-50% G, 10-45% G, 10-40% G, 10-35% G, 10-30% G, 10-25% G, 10-20% G, 10-15% G, 10-12.5% G, 12.5-50% G, 12.5-45% G, 12.5-40% G, 12.5-35% G, 12.5-30% G, 12.5-25% G, 12.5-20% G, 12.5-15% G, 15-50% G, 15-45% G, 15-40% G, 15-35% G, 15-30% G, 15-25% G, 15-20% G, 20-50% G, 20-45% G, 20-40% G, 20-35% G, 20-30% G, or 20-25% G. By "the composition consists of or consists essentially of unique oligonucleotide species that each have a molecule barcodes G content less than . . . ", it is mean that each or essentially each of the unique oligonucleotide species in a composition, population, or pool have a molecule barcode G content below the indicated value, or outside the indicated range. That is, for a composition, population, or pool "consisting essentially of" unique oligonucleotide species that each have the indicated G content, it would be possible for an analytically insignificant portion of the unique oligonucleotides in the composition to have molecule barcodes with a G content above the indicated value or outside the recited range. For example, the analytically insignificant portion of the unique oligonucleotides can be, or can be no more than, 5%, 4%, 3%, 2%, 1%, 0.5%, 0.4%, 0.3%, 0.2%, 0.1%, or less of the unique oligonucleotide in a composition. In some embodiments, less than 1% of the unique oligonucleotide species in a composition comprising at least 1000 unique oligonucleotides comprise a molecule barcode having a G content of greater than 50%, for example less than 1%, 0.9%, 0.8%, 0.7%, 0.6%, 0.5%, 0.4%, 0.3%, 0.2%, 0.1%, 0.05%, 0.01%, 0.001%, or 0.0001% of the unique oligonucleotide species have the a G content of greater than 50%. In some embodiments, less than 1% of the unique oligonucleotide species in a composition comprising at least 6500 unique oligonucleotides comprise a molecule barcode having a G content of greater than 50%, for example less than 1%, 0.9%, 0.8%, 0.7%, 0.6%, 0.5%, 0.4%, 0.3%, 0.2%, 0.1%, 0.05%, 0.01%, 0.001%, or 0.0001% of the unique oligonucleotide species have a G content of greater than 50%. In some embodiments, less than 1% of the unique oligonucleotide species in a composition comprising at least 65,000 unique oligonucleotides comprise a molecule barcode having a G content of greater than 50%, for example less than 1%, 0.9%, 0.8%, 0.7%, 0.6%, 0.5%, 0.4%, 0.3%, 0.2%, 0.1%, 0.05%, 0.01%, 0.001%, or 0.0001% of the unique oligonucleotide species have a G content of greater than 50%. In some embodiments, less than 1% of the unique oligonucleotide species in a composition comprising at least 1000 unique oligonucleotides comprise a molecule barcode having a G content of greater than 25%, for example less than 1%, 0.9%, 0.8%, 0.7%, 0.6%, 0.5%, 0.4%, 0.3%, 0.2%, 0.1%, 0.05%, 0.01%, 0.001%, or 0.0001% of the unique oligonucleotide species have a G content of greater than 25%. In some embodiments, less than 1% of the unique oligonucleotide species in a composition of at least 6500 unique oligonucleotides comprise a molecule barcode having a G content of greater than 25%, for example less than 1%, 0.9%, 0.8%, 0.7%, 0.6%, 0.5%, 0.4%, 0.3%, 0.2%, 0.1%, 0.05%, 0.01%, 0.001%, or 0.0001% of the unique oligonucleotide species have a G content of greater than 25%. In some embodiments, less than 1% of the unique oligonucleotide species in a composition, population, or pool of at least 65,000 unique oligonucleotides comprise a molecule barcode having a G content of greater than 25%, for example less than 1%, 0.9%, 0.8%, 0.7%, 0.6%, 0.5%, 0.4%, 0.3%, 0.2%, 0.1%, 0.05%, 0.01%, 0.001%, or 0.0001% of the unique oligonucleotide species have a G content of greater than 25%. Optionally, none of the molecule barcodes of the unique oligonucleotide species of the composition collectively have a G content of greater than 50% G, for example, all of the molecule barcodes of the unique oligonucleotide species have a G content less than 50% G, 45% G, 40% G, 35% G, 30% G, 25% G, 20% G, 15% G, 12.5% G, 10% G, 7.5% G, 5% G, or 2.5% G, or 0% G, including ranges between any two of the listed values.

In some embodiments, the composition as described herein (or such a composition as used in a method) consists of or consists essentially of unique oligonucleotide species that each comprise a barcode region G content of less than 50% as described herein. In some embodiments, for a composition comprising unique oligonucleotide species, the composition consists of or consists essentially of unique oligonucleotide species that each comprise a barcode region G content of 50% G or less, for example, less than 50% G, 45% G, 40% G, 35% G, 30% G, 25% G, 20% G, 15% G, 12.5% G, 10% G, 7.5% G, 5% G, or 2.5% G, or 0% G, including ranges between any two of the listed values, for example 2.5-50% G, 2.5-45% G, 2.5-40% G, 2.5-35% G, 2.5-30% G, 2.5-25% G, 2.5-20% G, 2.5-15% G, 2.5-10% G, 2.5-7.5% G, 2.5-5% G, 5-50% G, 5-45% G, 5-40% G, 5-35% G, 5-30% G, 5-25% G, 5-20% G, 5-15% G, 5-10% G, 5-7.5% G, 7.5-50% G, 7.5-45% G, 7.5-40% G, 7.5-35% G, 7.5-30% G, 7.5-25% G, 7.5-20% G, 7.5-15% G, 7.5-10% G, 10-50% G, 10-45% G, 10-40% G, 10-35% G, 10-30% G, 10-25% G, 10-20% G, 10-15% G, 10-12.5% G, 12.5-50% G, 12.5-45% G, 12.5-40% G, 12.5-35% G, 12.5-30% G, 12.5-25% G, 12.5-20% G, 12.5-15% G, 15-50% G, 15-45% G, 15-40% G, 15-35% G, 15-30% G, 15-25% G, 15-20% G, 20-50% G, 20-45% G, 20-40% G, 20-35% G, 20-30% G, or 20-25% G. By "the composition consists of or consists essentially of unique oligonucleotide species that each have a barcode regions G content less than . . . ", it is mean that each or essentially each of the unique oligonucleotide species in a composition, population, or pool have a barcode region G content below the indicated value, or outside the indicated range. That is, for a composition, population, or pool "consisting essentially of" unique oligonucleotide species that each have the indicated G content, it would be possible for an analytically insignificant portion of the unique oligonucleotides in the composition to have barcode regions with a G content above the indicated value or outside the recited range. In some embodiments, less than 1% of the unique oligonucleotide species in a composition comprising at least 1000 unique oligonucleotides comprise a barcode region having a G content of greater than 50%, for example less than 1%, 0.9%, 0.8%, 0.7%, 0.6%, 0.5%, 0.4%, 0.3%, 0.2%, 0.1%, 0.05%, 0.01%, 0.001%, or 0.0001% of the unique oligonucleotide species have a G content greater than 50%, including ranges between any two of the listed values. In some embodiments, less than 1% of the unique oligonucleotide species in a composition comprising at least 6500 unique oligonucleotides comprise a barcode region having a G content of greater than 50%, for example less than 1%, 0.9%, 0.8%, 0.7%, 0.6%, 0.5%, 0.4%, 0.3%, 0.2%, 0.1%, 0.05%, 0.01%, 0.001%, or 0.0001% of the unique oligonucleotide species have a G content greater than 50%, including ranges between any two of the listed values. In some embodiments, less than 1% of the unique oligonucleotide species in a composition comprising at least 65,000 unique oligonucleotides comprise a barcode region having a G content of greater than 50%, for example less than 1%, 0.9%, 0.8%, 0.7%, 0.6%, 0.5%, 0.4%, 0.3%, 0.2%, 0.1%, 0.05%, 0.01%, 0.001%, or 0.0001% of the unique oligonucleotide species have a G content greater than 50%, including ranges between any two of the listed values. In some embodiments, less than 1% of the unique oligonucleotide species in a composition comprising at least 1000 unique oligonucleotides comprise a barcode region having a G content of greater than 25%, for example less than 1%, 0.9%, 0.8%, 0.7%, 0.6%, 0.5%, 0.4%, 0.3%, 0.2%, 0.1%, 0.05%, 0.01%, 0.001%, or 0.0001% of the unique oligonucleotide species have a G content greater than 25%, including ranges between any two of the listed values. In some embodiments, less than 1% of the unique oligonucleotide species in a composition of at least 6500 unique oligonucleotides comprise a barcode region having a G content of greater than 25%, for example less than 1%, 0.9%, 0.8%, 0.7%, 0.6%, 0.5%, 0.4%, 0.3%, 0.2%, 0.1%, 0.05%, 0.01%, 0.001%, or 0.0001% of the unique oligonucleotide species have a G content greater than 50%, including ranges between any two of the listed values. In some embodiments, less than 1% of the unique oligonucleotide species in a composition, population, or pool of at least 65,000 unique oligonucleotides comprise a barcode region having a G content of greater than 25%, for example less than 1%, 0.9%, 0.8%, 0.7%, 0.6%, 0.5%, 0.4%, 0.3%, 0.2%, 0.1%, 0.05%, 0.01%, 0.001%, or 0.0001% of the unique oligonucleotide species have a G content greater than 25%, including ranges between any two of the listed values. Optionally, none of the barcode regions of the unique oligonucleotide species of the composition collectively have a G content of greater than 50% G, for example, all of the barcode regions of the unique oligonucleotide species have a G content less than 50% G, 45% G, 40% G, 35% G, 30% G, 25% G, 20% G, 15% G, 12.5% G, 10% G, 7.5% G, 5% G, or 2.5% G, or 0% G, including ranges between any two of the listed values.

In some embodiments, the composition (or such a composition as used in a method) consist of or consists essentially of unique oligonucleotide species that each have a molecule barcode comprising the sequence of at least three repeats of the doublet "HN" (in which each "H" is any of A, C, or T, and in which "N" is any of A, G, C, or T), for example at least 3, 4, 5, 6, 7, 8, 9, 10, 11, 12, 13, 14, 15, 16, 17, 18, 19, or 20 repeats, including ranges between any two of the listed values. Examples of multiple repeats of the doublet "HN" include HN, HNHN, HNHNHN, and HNHNHNHN. It is noted that while the formula "HN" describes constraints on the base content, not every H or every N has to be the same or different. For example, if the molecule barcodes of unique oligonucleotide species in a composition comprised HNHNHN, one molecule barcode can comprise the sequence ACTGCA, while another molecule barcode can comprise the sequence TAACTA, while another molecule barcode could comprise the sequence AGACAC. It is noted that any number of repeats of the doublet "HN" would have a G content of no more than 50%. In some embodiments, at least 95% of the unique oligonucleotide species of a composition comprising at least 1000 unique oligonucleotide species comprise molecule barcodes comprising at least three repeats of the doublet "HN," for example at least 3, 4, 5, 6, 7, 8, 9, 10, 11, 12, 13, 14, 15, 16, 17, 18, 19, or 20 repeats, including ranges between any two of the listed values. In some embodiments, at least 99% of the unique oligonucleotide species of a composition comprising at least 1000 unique oligonucleotide species comprise molecule barcodes comprising at least three repeats of the doublet "HN," for example at least 3, 4, 5, 6, 7, 8, 9, 10, 11, 12, 13, 14, 15, 16, 17, 18, 19, or 20 repeats, including ranges between any two of the listed values. In some embodiments, at least 99.9% of the unique oligonucleotide species of a composition comprising at least 1000 unique oligonucleotide species comprise molecule barcodes comprising at least three repeats of the doublet "HN," for example at least 3, 4, 5, 6, 7, 8, 9, 10, 11, 12, 13, 14, 15, 16, 17, 18, 19, or 20 repeats, including ranges between any two of the listed values. In some embodiments, at least 95% of the unique oligonucleotide species of a composition comprising at least 6500 unique oligonucleotide species comprise molecule barcodes comprising at least three repeats of the doublet "HN," for example at least 3, 4, 5, 6, 7, 8, 9, 10, 11, 12, 13, 14, 15, 16, 17, 18, 19, or 20 repeats, including ranges between any two of the listed values. In some embodiments, at least 99% of the unique oligonucleotide species of a composition comprising at least 6500 unique oligonucleotide species comprise molecule barcodes comprising at least three repeats of the doublet "HN," for example at least 3, 4, 5, 6, 7, 8, 9, 10, 11, 12, 13, 14, 15, 16, 17, 18, 19, or 20 repeats, including ranges between any two of the listed values. In some embodiments, at least 99.9% of the unique oligonucleotide species of a composition comprising at least 6500 unique oligonucleotide species comprise molecule barcodes comprising at least three repeats of the doublet "HN," for example at least 3, 4, 5, 6, 7, 8, 9, 10, 11, 12, 13, 14, 15, 16, 17, 18, 19, or 20 repeats, including ranges between any two of the listed values. In some embodiments, at least 95% of the unique oligonucleotide species of a composition comprising at least 65,000 unique oligonucleotide species comprise molecule barcodes comprising at least three repeats of the doublet "HN," for example at least 3, 4, 5, 6, 7, 8, 9, 10, 11, 12, 13, 14, 15, 16, 17, 18, 19, or 20 repeats, including ranges between any two of the listed values. In some embodiments, at least 99% of the unique oligonucleotide species of a a of composition comprising at least 65,000 unique oligonucleotide species comprise molecule barcodes comprising at least three repeats of the doublet "HN," for example at least 3, 4, 5, 6, 7, 8, 9, 10, 11, 12, 13, 14, 15, 16, 17, 18, 19, or 20 repeats, including ranges between any two of the listed values. In some embodiments, at least 99.9% of the unique oligonucleotide species of a composition comprising at least 65,000 unique oligonucleotide species comprise molecule barcodes comprising at least three repeats of the doublet "HN," for example at least 3, 4, 5, 6, 7, 8, 9, 10, 11, 12, 13, 14, 15, 16, 17, 18, 19, or 20 repeats, including ranges between any two of the listed values. In some embodiments, the composition consists of or consists essentially of at least 1000, 6500, or 65,000 unique oligonucleotide species that each have a molecule barcode comprising the sequence HNHNHN. In some embodiments, the composition consists of or consists essentially of of at least 1000, 6500, or 65,000 unique oligonucleotide species that each has a molecule barcode comprising the sequence HNHNHNHN. In some embodiments, at least 95%, 99%, or 99.9% of the barcode regions of the composition as described herein comprise at least three repeats of the doublet "HN" as described herein. Without being limited by any theory, it is noted that having a relatively large number of available nucleotides sequences for molecule barcodes can be helpful when barcoding a population of target nucleic acids from a sample, for example to increase the diversity of barcodes within a given sequence length along with the probability that each target nucleic acid will be uniquely labeled, while minimizing oligonucleotide species size. It is noted that limiting the G content of molecule barcodes and/or barcode regions can limit the diversity of these barcodes and barcode regions by decreasing the number of available nucleotides from which barcodes can be constructed (and the number of available different sequences per length of nucleic acid). As such, having some G' s in molecule barcodes or barcode regions in accordance with various embodiments herein can be helpful in increasing diversity, while limiting the G content can be helpful minimizing bias. It is noted, and has been observed (see Example 2 and FIGS. 6-7) that sequences comprising repeated "HN" doublets can yield low bias, while providing a compromise between reducing bias and maintaining a relatively large quantity of available nucleotide sequences, so that relatively high diversity can be obtained in a relatively short sequence, while still minimizing bias. In some embodiments, methods or compositions comprising unique oligonucleotide species comprising molecule barcodes comprising repeated "HN" doublets as described herein reduce bias by increasing sensitivity, decreasing relative standard error, or increasing sensitivity and reducing standard error.

In some embodiments, the composition (or such a composition as used in a method) comprises, consists of, or consists essentially of unique oligonucleotide species that each comprise a molecule barcode comprising at least six consecutive "H's" (in which each "H" is any of A, C, or T), for example at least 6, 7, 8, 9, 10, 11, 12, 13, 14, 15, 16, 17, 18, 19, or 20 consecutive H's, including ranges between any two of the listed values. It is noted that while the formula "H" describes constraints on the base content, not every H has to be the same (or different). For example, if the molecule barcodes of unique oligonucleotide species in a population each comprised the sequence HHHH, one molecule barcode of a unique oligonucleotide species could comprise ACTA, one molecule barcode of another unique oligonucleotide species could comprise TTAC, and one molecule barcode of another unique oligonucleotide species could comprise ACAT. In some embodiments, a composition comprises, consists of, or consists essentially of at least 1000 unique oligonucleotide species, of which at least 95% comprise a molecule barcode that comprises at least six consecutive H's, for example at least 6, 7, 8, 9, 10, 11, 12, 13, 14, 15, 16, 17, 18, 19, or 20 consecutive H's, including ranges between any two of the listed values. In some embodiments, a composition comprises, consists of, or consists essentially of at least 1000 unique oligonucleotide species, of which at least 99% comprise a molecule barcode that comprises at least six consecutive H's, for example at least 6, 7, 8, 9, 10, 11, 12, 13, 14, 15, 16, 17, 18, 19, or 20 consecutive H's, including ranges between any two of the listed values. In some embodiments, a composition comprises, consists of, or consists essentially of at least 1000 unique oligonucleotide species, of which at least 99.9% comprise a molecule barcode that comprises at least six consecutive H's, for example at least 6, 7, 8, 9, 10, 11, 12, 13, 14, 15, 16, 17, 18, 19, or 20 consecutive H's, including ranges between any two of the listed values. In some embodiments, a composition comprises, consists of, or consists essentially of at least 6500 unique oligonucleotide species, of which at least 95% comprise a molecule barcode that comprises at least six consecutive H's, for example at least 6, 7, 8, 9, 10, 11, 12, 13, 14, 15, 16, 17, 18, 19, or 20 consecutive H's, including ranges between any two of the listed values. In some embodiments, a composition comprises, consists of, or consists essentially of at least 6500 unique oligonucleotide species, of which at least 99% comprise a molecule barcode that comprises at least six consecutive H's, for example at least 6, 7, 8, 9, 10, 11, 12, 13, 14, 15, 16, 17, 18, 19, or 20 consecutive H's, including ranges between any two of the listed values. In some embodiments, a composition comprises, consists of, or consists essentially of at least 6500 unique oligonucleotide species, of which at least 99.9% comprise a molecule barcode that comprises at least six consecutive H's, for example at least 6, 7, 8, 9, 10, 11, 12, 13, 14, 15, 16, 17, 18, 19, or 20 consecutive H's, including ranges between any two of the listed values. In some embodiments, a composition comprises, consists of, or consists essentially of at least 65,000 unique oligonucleotide species, of which at least 95% comprise a molecule barcode that comprises at least six consecutive H's, for example at least 6, 7, 8, 9, 10, 11, 12, 13, 14, 15, 16, 17, 18, 19, or 20 consecutive H's, including ranges between any two of the listed values. In some embodiments, a composition comprises, consists of, or consists essentially of at least 65,000 unique oligonucleotide species, of which at least 99% comprise a molecule barcode that comprises at least six consecutive H's, for example at least 6, 7, 8, 9, 10, 11, 12, 13, 14, 15, 16, 17, 18, 19, or 20 consecutive H's, including ranges between any two of the listed values. In some embodiments, a composition comprises, consists of, or consists essentially of at least 65,000 unique oligonucleotide species, of which at least 99.9% comprise a molecule barcode that comprises at least six consecutive H's, for example at least 6, 7, 8, 9, 10, 11, 12, 13, 14, 15, 16, 17, 18, 19, or 20 consecutive H's, including ranges between any two of the listed values. In some embodiments, at least 95% of the molecule barcodes of the unique oligonucleotide species comprise a sequence totaling at least 6 alternating H's and N's, for example at least 6, 7, 8, 9, 10, 11, 12, 13, 14, 15, 16, 17, 18, 19, or 20 alternating H's and N's, including ranges between any two of the listed values. In some embodiments, at least 95% of the molecule barcodes of the unique oligonucleotide species comprise the sequence HNHNHNHN, wherein each "H" is any one of A, C, or T, and wherein each "N" is any one of A, G, C, or T. In some embodiments, each molecule barcode of the unique oligonucleotide species comprises the sequence HNHNHNHN, wherein each "H" is any one of A, C, or T, and wherein each "N" is any one of A, G, C, or T. In some embodiments, each molecule barcode of the unique oligonucleotide species comprises the sequence HHHHHHHH, wherein each "H" is any one of A, C, or T.

In some embodiments, at least 95% (e.g., 95%, 96%, 97%, 98%, 99% or more) of the unique oligonucleotide species of the composition as described herein (or such a composition as used in a method) comprise barcode regions comprising at least 6 consecutive H's, for example at least 6, 7, 8, 9, 10, 11, 12, 13, 14, 15, 16, 17, 18, 19, or 20 consecutive H's, including ranges between any two of the listed values as described herein. In some embodiments, at least 99% of the unique oligonucleotide species of the composition as described herein comprise barcode regions comprising at least 6 consecutive H's, for example at least 6, 7, 8, 9, 10, 11, 12, 13, 14, 15, 16, 17, 18, 19, or 20 consecutive H's, including ranges between any two of the listed values as described herein. In some embodiments, at least 99.9% of the unique oligonucleotide species of the composition as described herein comprise barcode regions comprising at least 6 consecutive H's, for example at least 6, 7, 8, 9, 10, 11, 12, 13, 14, 15, 16, 17, 18, 19, or 20 consecutive H's, including ranges between any two of the listed values as described herein.

In some embodiments, the sample barcode of each unique oligonucleotide species has a G content of 50% or less, for example 50% or less, 40% or less, 25% or less, 20% or less, 12.5% or less, 10% or less, or 5% or less, including ranges between any two of the listed values.

In some embodiments, the barcode region of each unique oligonucleotide species has a G content of 50% or less, for example 50% or less, 40% or less, 25% or less, 20% or less, 12.5% or less, 10% or less, or 5% or less, including ranges between any two of the listed values.

In some embodiments, the molecule barcodes of the unique oligonucleotide species collectively have a G content of less than 12.5%, for example less than 12.5%, less than 10%, less than 7.5%, less than 5%, less than 2.5%, or less than 1%, including ranges between any two of the listed values.

In some embodiments, the barcode regions of the unique oligonucleotide species collectively have a G content of less than 12.5%, for example less than 12.5%, less than 10%, less than 7.5%, less than 5%, less than 2.5%, or less than 1%, including ranges between any two of the listed values.

In some embodiments, for at least 95% of the unique oligonucleotide species, any G in the molecule barcode is not adjacent to another G. In some embodiments, for at least 99% of the unique oligonucleotide species, any G in the molecule barcode is not adjacent to another G. In some embodiments, for all or substantially all of the unique oligonucleotide species, any G in the molecule barcode is not adjacent to another G.

Each barcode region can optionally comprise a sample barcode. In accordance with compositions, methods, and oligonucleotides of some embodiments herein, each unique oligonucleotide species in a pool can comprise the same sample barcode, but there can be two or more pools that are each associated with different sample barcodes. As such, all or essentially all of the unique oligonucleotide species in pool #1 can comprise sample barcode #1, and all or essentially all of the unique oligonucleotide species in pool #2 can comprise sample barcode #2. Nucleic acids from a first sample can be associated with the unique oligonucleotide species in pool #1, and nucleic acids from a second sample can associated with unique oligonucleotide species in pool #2, for example by hybridization and amplification. As such, all or essentially all of the amplified nucleic acids corresponding to the first sample will comprise sample barcode #1 (but can comprise different molecule barcodes), and all of the amplified nucleic acids corresponding to the second sample will comprise sample barcode #2. In some embodiments, there are at least 24, 48, 96, or 192 pools.

The sample barcode can comprise a nucleic acid sequence of at least 3 nucleotides, for example at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nucleotides, including ranges between any two of the listed values, for example 3-50, 3-45, 3-40, 3-35, 3-30, 3-25, 3-20, 3-15, 3-14, 3-13, 3-12, 3-11, 3-10, 3-9, 3-8, 3-7, 3-6, 3-5, 3-4, 4-50, 4-45, 4-40, 4-35, 4-30, 4-25, 4-20, 4-15, 4-14, 4-13, 4-12, 4-11, 4-10, 4-9, 4-8, 4-7, 4-6, 4-5, 5-50, 5-45, 5-40, 5-35, 5-30, 5-25, 5-20, 5-15, 5-14, 5-13, 5-12, 5-11, 5-10, 5-9, 5-8, 5-7, 5-6, 6-50, 6-45, 6-40, 6-35, 6-30, 6-25, 6-20, 6-15, 6-14, 6-13, 6-12, 6-11, 6-10, 6-9, 6-8, 6-7, 7-50, 7-45, 7-40, 7-35, 7-30, 7-25, 7-20, 7-15, 7-14, 7-13, 7-12, 7-11, 7-10, 7-9, 7-8, 8-50, 8-45, 8-40, 8-35, 8-30, 8-25, 8-20, 8-15, 8-14, 8-13, 8-12, 8-11, 8-10, 8-9, 9-50, 9-45, 9-40, 9-35, 9-30, 9-25, 9-20, 9-15, 9-14, 9-13, 9-12, 9-11, 9-10, 10-50, 10-45, 10-40, 10-35, 10-30, 10-25, 10-20, 10-15, 10-14, 10-13, 10-12, or 10-11 nucleotides. In some embodiments, the nucleic acid sequence of the sample barcode comprises a unique sequence, for example, so that each unique oligonucleotide species in a population comprises a different molecule barcode.

Without being limited by any theory, it is contemplated that a sample barcode comprising a low G content (e.g., less than 50% G, for example, less than 45% G, 40% G, 35% G, 30% G, 25% G, 20% G, 15% G, 12.5% G, 10% G, 7.5% G, 5% G, or 2.5% G) can be positioned 3' of a sample barcode that comprises a relatively higher G content and 5' of a uniform region (e.g. a target-specific sequence or oligo dT sequence), so as to minimize bias by separating the relatively G-rich sample barcode from the uniform region. In some embodiments, the barcode region comprises a sample barcode comprising 50% G content or less, for example, less than 50% G, 45% G, 40% G, 35% G, 30% G, 25% G, 20% G, 15% G, 12.5% G, 10% G, 7.5% G, 5% G, or 2.5% G, or 0% G, including ranges between any two of the listed values, for example 2.5-50% G, 2.5-45% G, 2.5-40% G, 2.5-35% G, 2.5-30% G, 2.5-25% G, 2.5-20% G, 2.5-15% G, 2.5-10% G, 2.5-7.5% G, 2.5-5% G, 5-50% G, 5-45% G, 5-40% G, 5-35% G, 5-30% G, 5-25% G, 5-20% G, 5-15% G, 5-10% G, 5-7.5% G, 7.5-50% G, 7.5-45% G, 7.5-40% G, 7.5-35% G, 7.5-30% G, 7.5-25% G, 7.5-20% G, 7.5-15% G, 7.5-10% G, 10-50% G, 10-45% G, 10-40% G, 10-35% G, 10-30% G, 10-25% G, 10-20% G, 10-15% G, 10-12.5% G, 12.5-50% G, 12.5-45% G, 12.5-40% G, 12.5-35% G, 12.5-30% G, 12.5-25% G, 12.5-20% G, 12.5-15% G, 15-50% G, 15-45% G, 15-40% G, 15-35% G, 15-30% G, 15-25% G, 15-20% G, 20-50% G, 20-45% G, 20-40% G, 20-35% G, 20-30% G, or 20-25% G.

In some embodiments, for a composition comprising unique oligonucleotide species (or such a composition as used in a method), at least 95% of the sample barcodes of the unique oligonucleotides of the composition each have less than 50% G content, for example, less than 45% G, 40% G, 35% G, 30% G, 25% G, 20% G, 15% G, 12.5% G, 10% G, 7.5% G, 5% G, or 2.5% G, or 0% G, including ranges between any two of the listed values, for example 2.5-50% G, 2.5-45% G, 2.5-40% G, 2.5-35% G, 2.5-30% G, 2.5-25% G, 2.5-20% G, 2.5-15% G, 2.5-10% G, 2.5-7.5% G, 2.5-5% G, 5-50% G, 5-45% G, 5-40% G, 5-35% G, 5-30% G, 5-25% G, 5-20% G, 5-15% G, 5-10% G, 5-7.5% G, 7.5-50% G, 7.5-45% G, 7.5-40% G, 7.5-35% G, 7.5-30% G, 7.5-25% G, 7.5-20% G, 7.5-15% G, 7.5-10% G, 10-50% G, 10-45% G, 10-40% G, 10-35% G, 10-30% G, 10-25% G, 10-20% G, 10-15% G, 10-12.5% G, 12.5-50% G, 12.5-45% G, 12.5-40% G, 12.5-35% G, 12.5-30% G, 12.5-25% G, 12.5-20% G, 12.5-15% G, 15-50% G, 15-45% G, 15-40% G, 15-35% G, 15-30% G, 15-25% G, 15-20% G, 20-50% G, 20-45% G, 20-40% G, 20-35% G, 20-30% G, or 20-25% G.

In some embodiments, for a composition comprising unique oligonucleotide species (or such a composition as used in a method), at least 99% of the sample barcodes of the unique oligonucleotides of the composition each have 50% G content or less, for example, less than 50% G, 45% G, 40% G, 35% G, 30% G, 25% G, 20% G, 15% G, 12.5% G, 10% G, 7.5% G, 5% G, or 2.5% G, or 0% G, including ranges between any two of the listed values, for example 2.5-50% G, 2.5-45% G, 2.5-40% G, 2.5-35% G, 2.5-30% G, 2.5-25% G, 2.5-20% G, 2.5-15% G, 2.5-10% G, 2.5-7.5% G, 2.5-5% G, 5-50% G, 5-45% G, 5-40% G, 5-35% G, 5-30% G, 5-25% G, 5-20% G, 5-15% G, 5-10% G, 5-7.5% G, 7.5-50% G, 7.5-45% G, 7.5-40% G, 7.5-35% G, 7.5-30% G, 7.5-25% G, 7.5-20% G, 7.5-15% G, 7.5-10% G, 10-50% G, 10-45% G, 10-40% G, 10-35% G, 10-30% G, 10-25% G, 10-20% G, 10-15% G, 10-12.5% G, 12.5-50% G, 12.5-45% G, 12.5-40% G, 12.5-35% G, 12.5-30% G, 12.5-25% G, 12.5-20% G, 12.5-15% G, 15-50% G, 15-45% G, 15-40% G, 15-35% G, 15-30% G, 15-25% G, 15-20% G, 20-50% G, 20-45% G, 20-40% G, 20-35% G, 20-30% G, or 20-25% G. That is, within the population of unique oligonucleotides, less than 1% of the sample barcodes have G content greater than 50%. In some embodiments, the unique oligonucleotide species of the composition consist of or consists essentially of unique oligonucleotide species that each have sample barcodes having less than 50% G content, as described herein.

In some embodiments, a barcode region is positioned 5' of the uniform region without any intervening sequences between the barcode region and the uniform region. In some embodiments, the barcode region is positioned 5' of a spacer, which is positioned 5' of the the uniform region, so that a spacer is between the barcode region and the uniform region. Optionally, the spacer has a low G content (e.g., 50% G or less, for example, less than 50% G, 45% G, 40% G, 35% G, 30% G, 25% G, 20% G, 15% G, 12.5% G, 10% G, 7.5% G, 5% G, or 2.5% G). The spacer can have a length of at least 1 nucleotide, for example 1, 2, 3, 4, 5, 6, 7, 8, 9, 10, 11, 12, 13, 14, 15, 16, 17, 18, 19, 20, 25, 30, 35, 40, 45, or 50 nucleotides, including ranges between any two of the listed values, for example 1-50, 1-45, 1-35, 1-30, 1-25, 1-20, 1-15, 1-10, 1-9, 1-8, 1-7, 1-6, 1-5, 1-4, 1-3, 1-2, 2-50, 2-45, 2-35, 2-30, 2-25, 2-20, 2-15, 2-10, 2-9, 2-8, 2-7, 2-6, 2-5, 2-4, 2-3, 3-50, 3-45, 3-35, 3-30, 3-25, 3-20, 3-15, 3-10, 3-9, 3-8, 3-7, 3-6, 3-5, 3-4, 4-50, 4-45, 4-35, 4-30, 4-25, 4-20, 4-15, 4-10, 4-9, 4-8, 4-7, 4-6, 4-5, 5-50, 5-45, 5-35, 5-30, 5-25, 5-20, 5-15, 5-10, 5-9, 5-8, 5-7, 5-6, 6-50, 6-45, 6-35, 6-30, 6-25, 6-20, 6-15, 6-10, 6-9, 6-8, 6-7, 7-50, 7-45, 7-35, 7-30, 7-25, 7-20, 7-15, 7-10, 7-9, 7-8, 8-50, 8-45, 8-35, 8-30, 8-25, 8-20, 8-15, 8-10, 8-9, 9-50, 9-45, 9-35, 9-30, 9-25, 9-20, 9-15, 9-10, 10-50, 10-45, 10-35, 10-30, 10-25, 10-20, or 10-15 nucleotides. In some embodiments, the spacer can comprise at least two consecutive non-G nucleotides (denoted as "H", in which "H" is A, C, or T), for example at least 2, 3, 4, 5, 6, 7, 8, 9, 10, 11, 12, 13, 14, 15, 16, 17, 18, 19, or 20 consecutive H's, including ranges between any two of the listed values, for example 2-20, 2-15, 2-10, 2-9, 2-8, 2-7, 2-6, 2-5, 2-4, 2-3, 3-20, 3-15, 3-10, 3-9, 3-8, 3-7, 3-6, 3-5, 3-4, 4-20, 4-15, 4-10, 4-9, 4-8, 4-7, 4-6, 4-5, 5-20, 5-15, 5-10, 5-9, 5-8, 5-7, 5-6, 6-20, 6-15, 6-10, 6-9, 6-8, or 6-7. In some embodiments, the nucleotides of the spacers are Ts. For example, the space can comprise a poly-T sequence, such as TT, TTT, TTTT, TTTTT, TTTTTT, TTTTTTTT, or TTTTTTTTTT. It noted that the spacers do not necessarily provide diversity, and as such, in a composition comprising unique oligonucleotide species as described herein, some or all of the unique oligonucleotide species can have the same spacer sequences. Optionally, all of the unique oligonucleotide species of the composition comprise the same spacer sequence.

Pools and Pooling

Compositions comprising unique oligonucleotide species as described in accordance with compositions and methods of some embodiments herein can be disposed in spatially isolated pools, for example so that multiple sample can be analyzed, with one sample per pool. In some embodiments, the unique oligonucleotide species are disposed in spatially isolated pools, each pool comprising a plurality of unique oligonucleotides of the unique oligonucleotide species, so that unique oligonucleotides in the same pool comprise the same sample barcode sequence, and so that different unique oligonucleotides of the same pool comprise a different molecule barcode sequences. As used herein, "spatial isolation" (and variations of this root term) means that target nucleic acids of a sample can hybridize to the unique oligonucleotide species of the pool without substantially cross-reacting with other pools, and without the unique oligonucleotide species of the pool substantially hybridizing to target nucleic acids of other samples. As such, the sample barcode can identify which pool a given unique oligonucleotide species came from. Moreover, upon barcoding target nucleic acid sequences with unique oligonucleotide species, the sample barcode can identify which pool a barcoded target nucleic acid sequence (or reverse transcript or amplicon thereof) came from.

In some embodiments, a substrate organizes the pools so that they are spatially isolated from each other. For example, a multi-well plate can organize spatially isolated pools, so that each pool is in a separate well. For example, each pool can be immobilized on a different bead. Optionally, each well of a multi-well plate can contain a single bead on which the pool of unique oligonucleotide species is immobilized, so that a different pool of unique oligonucleotide species is positioned in each well of the multi-well plate.

In some embodiments, the unique oligonucleotide species are disposed in at least 2 pools, for example, at least 2, 3, 4, 4, 5, 6, 7, 8, 9, 10, 11, 12, 13, 14 15, 16, 17, 18, 19, 20, 21 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 72, 96, 99, 100, 110, 120, 144, 168, or 192, pools, including ranges between any two of the listed values. Optionally, there can be at least 100 unique oligonucleotides per pool.

In some embodiments, the unique oligonucleotide species are disposed in at least 2 pools, and there are at least 100 unique oligonucleotides per pool for example at least 100, 200, 300, 400, 500, 1000, 2000, 3000, 4000, 5000, 6000, 6500, 10,000, or 65,000 unique oligonucleotide species per pool.

In some embodiments, the unique oligonucleotide species are disposed in at least 24 pools, and there are at least 100 unique oligonucleotides per pool for example at least 100, 200, 300, 400, 500, 1000, 2000, 3000, 4000, 5000, 6000, 6500, 10,000, or 65,000 unique oligonucleotide species per pool.

In some embodiments, the unique oligonucleotide species are disposed in at least 48 pools, and there are at least 100 unique oligonucleotides per pool for example at least 100, 200, 300, 400, 500, 1000, 2000, 3000, 4000, 5000, 6000, 6500, 10,000, or 65,000 unique oligonucleotide species per pool.

In some embodiments, the unique oligonucleotide species are disposed in at least 96 pools, and there are at least 100 unique oligonucleotides per pool for example at least 100, 200, 300, 400, 500, 1000, 2000, 3000, 4000, 5000, 6000, 6500, 10,000, or 65,000 unique oligonucleotide species per pool.

Substrates

Unique oligonucleotide species in accordance with compositions and methods of some embodiments herein can be immobilized on substrates, for example beads, wells of multi-well plates, or arrays. For example, unique oligonucleotide species having the same sample barcode, but different molecule barcodes can all be immobilized on a substrate, such as on a single bead, or in a single well of a multi-well plate. As such, when the immobilized unique oligonucleotide species of a particular substrate are contacted with a particular sample, such as a single cell, the immobilized unique oligonucleotide species immobilized on that substrate will be associated with target nucleic acids of the same sample. If the unique oligonucleotide species immobilized on the same substrate have the same sample barcode, while those on other substrates have different sample barcodes, the sample associated with each target nucleic acid can be readily identified (e.g. all of the unique oligonucleotide species on substrate #1 have sample barcode #1, all of the unique oligonucleotide species on substrate #2 have sample barcode #2).

In some embodiments, such configurations in which unique oligonucleotide species are immobilized on a substrate can be helpful in facilitating efficiency and throughput. For example, single cells can be added to wells of a multi-well plate, so that no more than one single cell is in each well. If the unique oligonucleotide species immobilized within a given well (for example, on the well or on a bead) comprise a unique sample barcode, barcoded target nucleic acids and reverse-transcripts and amplicons thereof corresponding to the single cell can be identified and quantified, even if barcoded reverse transcripts or amplicons from multiple samples are pooled.

A substrate can comprise a type of solid support. A substrate can refer to a continuous solid or semi-solid surface on which the methods of the disclosure may be performed. A substrate can refer to an array, a cartridge, a chip, a device, and a slide, for example. As such, "solid support" and "substrate" can be used interchangeably.

A substrate or solid support in accordance with some embodiments herein can encompass any type of solid, porous, or hollow sphere, ball, bearing, cylinder, or other similar configuration composed of plastic, ceramic, metal, or polymeric material (e.g., hydrogel) onto which a nucleic acid may be immobilized (e.g., covalently or non-covalently). A substrate or solid support can comprise a discrete particle that may be spherical (e.g., microspheres) or have a non-spherical or irregular shape, such as cubic, cuboid, pyramidal, cylindrical, conical, oblong, or disc-shaped, and the like. A plurality of solid supports spaced in an array may not comprise a substrate. A solid support may be used interchangeably with the term "bead."

In some embodiments, a plurality of substrates is provided, and the diversity of sample barcodes can be represented in the plurality of substrates, so that unique substrates can comprise unique sample barcodes.

Methods of Barcoding

In accordance with some embodiments herein, methods of specifically barcoding nucleic acids from two or more samples are described. Each sample can comprise nucleic acids. The method can comprise contacting each sample with a pool comprising a plurality of unique oligonucleotide species, as described herein. Each sample can be contacted in spatial isolation from the other samples. The unique polynucleotide species of each pool can comprise the same sample barcode and comprise different molecule barcodes. The method can include hybridizing target specific regions of at least some oligonucleotides of the unique oligonucleotide species to at least some of the nucleic acids of the sample. The method can include extending the hybridized oligonucleotides so as to produce strands comprising an oligonucleotide of the unique oligonucleotide species and a sequence complementary to the target region. Thus, for each sample, the produced strands can comprise the same sample barcode and different molecule barcodes. For different samples, the sample barcodes can be different. In some embodiments, the unique oligonucleotide species contacted with the sample consist of or consist essentially of unique oligonucleotide species wherein each molecule barcode has a G content of less than 50%. In some embodiments, the molecule barcodes of all of the unique oligonucleotide species collectively have a G content of no more than 12.5%. Optionally each pool comprises at least 100 unique oligonucleotide species, for example at least 100, 500, 100, 500, 1000, 2000, 6500, or 65,000 unique oligonucleotide species. Such methods in accordance with some embodiments herein can barcode nucleic acids of two or more different samples, such as single-cell sample, so as to permit analysis and quantification of the nucleic acids of a single cell.

Optionally, each sample is contacted with a single pool of unique oligonucleotide species in spatial isolation from the other pools and samples. In some embodiments, the pools are spatially isolated by being in unique contained spaces, for example different wells of a multi-well plate, different test tubes, different microfluidic channels, or the like. In some embodiments, the pools are spatially isolated by being on different regions of a surface, for example reaction dots on an array.

The oligonucleotides can be contacted with target nucleic acids of the sample under standard hybridization conditions (e.g., in standard buffers, and at a temperature lower than the Tm of a portion of the uniform region that is complementary to the target nucleic acid). Optionally, for example if the target nucleic acids comprise RNAs, the target nucleic acids of the sample are reverse-transcribed after hybridization to the unique oligonucleotide species, so as to generate DNAs (e.g. cDNAs). Optionally, the products of the hybridization or reverse transcription reaction are amplified, so as to generate a library of DNAs. The amplification can be via PCR under standard conditions, or via other suitable methods, for example isothermal amplification, rolling circle amplification, and the like. Optionally, the amplification can comprise amplifying reverse-transcripts or hybridized nucleic acids with a polymerase having 5' to 3' activity. Optionally, the products of the amplification can be further analyzed, for example by sequence. Optionally, reverse transcripts or amplicons from different pools can be pooled for sequencing, as different sample barcodes will indicate the corresponding pool (and sample) of each individual barcoded nucleic acid. It is noted that there may be bias in favor of G-rich molecule barcode or unique oligonucleotide species, and methods in accordance with some embodiments herein can minimize or eliminate such bias. By way of example, when quantifying nucleic acids of the sample at the single nucleic acid level, it can be useful to minimize or eliminate such bias that could favor representation of some nucleic acids and skew quantitative results in favor of certain kinds of barcodes rather than representative target nucleic acids of the sample. In some embodiments, methods comprising unique oligonucleotide species as described herein reduce bias by increasing sensitivity, decreasing relative standard error, or increasing sensitivity and reducing standard error.

Optionally, the method can further comprise ascertaining nucleic acid sequences of the strands comprising the oligonucleotides of the unique oligonucleotide species and the sequence complementary to the target. For example, reverse transcripts, amplicons, and/or cDNA libraries generated from the hybridization and extension of the unique oligonucleotide probes can be sequenced. Any suitable sequencing method known in the art can be used, preferably high-throughput approaches. For example, cyclic array sequencing using platforms such as Roche 454, Illumina Solexa, ABI-SOLiD, ION Torrent, Complete Genomics, Pacific Bioscience, Helicos, or the Polonator platform, may also be utilized. Sequencing may comprise MiSeq sequencing. Sequencing may comprise HiSeq sequencing. If applicable, the unique oligonucleotide species can comprise adapters to mediate high-throughput sequencing, for example universal priming sites. Optionally, barcoded nucleic acids corresponding to two or more different samples (e.g. from two or more different pools) can be pooled or combined for sequencing. Optionally, all of the pools are combined or pooled for sequencing. Without being limited by any theory, it is noted that sample barcodes can identify the corresponding sample (or pool) of the combined barcoded nucleic acids, that combining or pooling the nucleic acids can facilitate throughput and/or resource utilization for sequencing, and that accurate barcoding in accordance with some embodiments herein can minimize or eliminate bias, even when a large number of different nucleic acids are analyzed.

In some embodiments, the barcode region of each pool comprises a sample barcode comprising at least 3 nucleotides as described herein, for example at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides, including ranges between any two of the listed values. Optionally, the sample barcode is positioned 3' of the molecule barcode. Optionally, the molecule barcode is positioned 3' of the sample barcode. Optionally, the unique oligonucleotide species comprise the same sample barcode, which can be a different sample barcode from the unique oligonucleotide species of other pools. Optionally, the sample barcode has a low G content as described herein, for example less than 50% G, for example, less than 45% G, 40% G, 35% G, 30% G, 25% G, 20% G, 15% G, 12.5% G, 10% G, 7.5% G, 5% G, or 2.5% G. Optionally, at least 95%, 99%, or 99.9% of the sample barcodes have a low G content as described herein. Optionally, each unique oligonucleotide comprises a spacer 3' of the molecule barcode and 5' of the uniform region as described herein.

In some embodiments, the unique oligonucleotide species contacted with the sample consist essentially of unique oligonucleotide species in which each molecule barcode has a G content of less than 50% as described herein, for example, less than 45% G, 40% G, 35% G, 30% G, 25% G, 20% G, 15% G, 12.5% G, 10% G, 7.5% G, 5% G, or 2.5% G content, or 0% G content. In some embodiments, the molecule barcodes of at least 95% of the unique oligonucleotide species contacted with the sample comprise molecule barcodes having a G content of less than 50% as described herein, for example, less than 45% G, 40% G, 35% G, 30% G, 25% G, 20% G, 15% G, 12.5% G, 10% G, 7.5% G, 5% G, or 2.5% G content, or 0% G content. In some embodiments, the molecule barcodes of at least 99% of the unique oligonucleotide species contacted with the sample comprise molecule barcodes having a G content of less than 50% as described herein, for example, less than 45% G, 40% G, 35% G, 30% G, 25% G, 20% G, 15% G, 12.5% G, 10% G, 7.5% G, 5% G, or 2.5% G content, or 0% G content. In some embodiments, all of the molecule barcodes of the unique oligonucleotide species contacted with the sample comprise molecule barcodes having a G content of less than 50% as described herein, for example, less than 45% G, 40% G, 35% G, 30% G, 25% G, 20% G, 15% G, 12.5% G, 10% G, 7.5% G, 5% G, or 2.5% G content, or 0% G content.

In some embodiments, the molecule barcodes of all of the unique oligonucleotide species collectively have a G content of less than 50% G, for example, less than 45% G, 40% G, 35% G, 30% G, 25% G, 20% G, 15% G, 12.5% G, 10% G, 7.5% G, 5% G, or 2.5% G, or 0% G, including ranges between any two of the listed values. In some embodiments, the molecule barcodes of all of the unique oligonucleotide species collectively have a G content of no more than 12.5%.

In some embodiments, each unique oligonucleotide species further comprises a uniform region 3' of the barcode region. Optionally, the uniform region comprises at least 10 nucleotides complementary to a target nucleic acid sequence (e.g., at least 10, 11, 12, 13, 14, 15, 16, 17, 18, 19, 20, 21, 22, 23, 24, 25, 26, 27, 28, 29, or 30 nucleotides complementary to the target, including ranges between any two of the listed values), and configured for 5' to 3' amplification of the target nucleic acid sequence. Optionally, the uniform region comprises an oligo dT sequence.

In some embodiments, the unique oligonucleotide species of each pool are immobilized on a substrate as described herein, so that the unique oligonucleotide species immobilized on a given substrate comprise the same sample barcode, and different unique oligonucleotide species immobilized on the substrate comprise different molecule barcodes. By way of example, substrates can include wells in multi-well plates (e.g. 24-, 48, and 96-well plates), spots on an array, beads, and the like. In some embodiments, at least 100 unique oligonucleotides are immobilized on each substrate. Optionally, all of the unique oligonucleotide species immobilized on a given substrate (and thus in the same pool) comprise the same sample barcode. In some embodiments, each sample barcode has a G content of 50% or less, for example 50% or less, 40% or less, 25% or less, 20% or less, 12.5% or less, 10% or less, or 5% or less.

In some embodiments, the molecule barcodes of the unique oligonucleotide species collectively have a G content of less than 12.5%, for example less than 12.5%, less than 10%, less than 7.5%, less than 5%, less than 2.5%, or less than 1%.

In some embodiments, the barcode regions of the unique oligonucleotide species collectively have a G content of no more than 12.5%, for example no more than 12.5%, no more than 10%, no more than 7.5%, no more than 5%, no more than 2.5%, or no more than 1%.

In some embodiments, for at least 95% of the unique oligonucleotide species, any G in the molecule barcode is not adjacent to another G. For example, for at least 95%, 96%, 97%, 98%, 99%, 99.5%, 99.9%, or 99.99%, of the unique oligonucleotide species, any G in the molecule barcode can be not-adjacent to another G.

In some embodiments, each pool consists of, or consists essentially of unique oligonucleotide species for which any G in the molecule barcode is not adjacent to another G.

In some embodiments, at least 95% of the molecule barcodes of the unique oligonucleotide species comprise a sequence totaling at least 6 alternating H's and N's, for example at least 6, 7, 8, 9, 10, 11, 12, 13, 14, 15, 16, 17, 18, 19, or 20 alternating H's and N's, including ranges between any two of the listed values. By way of example, 6 alternating H's and N's can be depicted as HNHNHN. It is noted that each H can be the same as, or different from any other H, and that each N can be the same as, or different from any other N.

In some embodiments, at least 95% of the molecule barcodes of the unique oligonucleotide species comprise the sequence HNHNHNHN, in which each "H" is any one of A, C, or T, and wherein each "N" is any one of A, G, C, or T. For example at least 95%, 96%, 97,%, 98%, 99%, 99.5%, 99.9%, or 99.99% of the molecule barcodes of the unique oligonucleotide species can comprise the sequence HNHNHNHN. It is noted that each H can be the same as, or different from any other H, and that each N can be the same as, or different from any other N. In some embodiments, each molecule barcode of the unique oligonucleotide species comprises the sequence HNHNHNHN.

In some embodiments, at least 99% of the molecule barcodes of the unique oligonucleotide species comprise the sequence HHHHHHHH, in which each "H" is any one of A, C, or T. For example at least 95%, 96%, 97,%, 98%, 99%, 99.5%, 99.9%, or 99.99% of the molecule barcodes of the unique oligonucleotide species can comprise the sequence HHHHHHHH. It is noted that each H can be the same as, or different from any other H. In some embodiments, each molecule barcode of the unique oligonucleotide species comprises the sequence HHHHHHHH.

In some embodiments, each unique oligonucleotide comprises a spacer 3' of the barcode region and 5' of the target specific region. Optionally, the spacer can comprise the sequence HNH, in which each "H" is any one of A, C, or T, and in which each "N" is any one of A, G, C, or T. Optionally, the spacer can comprise the sequence HHH. Optionally, the spacer can comprise the sequence HNHNHNHN. Optionally, the spacer can comprise the sequence HHHHHHHH. It is noted that each H can be the same as, or different from any other H, and that each N can be the same as, or different from any other N. In some embodiments, each unique oligonucleotide comprises a spacer 3' of the barcode region and 5' of the target specific region, said spacer comprising the sequence HNHNHNHN, in which each "H" is any one of A, C, or T, and in which each "N" is any one of A, G, C, or T. In some embodiments, unique oligonucleotide comprises a spacer 3' of the barcode region and 5' of the target specific region, said spacer comprising the sequence HHHHHHHH, in which each "H" is any one of A, C, or T.

In some embodiments, at least one pool comprises at least two oligonucleotides of the same unique oligonucleotide species. In some embodiments, no pool comprises two oligonucleotides of the same unique oligonucleotide species.

In some embodiments, the target specific region can comprise a sequence for 5' to 3' amplification of a target nucleic acid. In some embodiments, the target specific region comprises an oligo dT sequence. In some embodiments, the target specific region comprises a sequence flanking a sequence encoding a variable region of an immune cell receptor or immunoglobulin.

In some embodiments, for each unique oligonucleotide species, the molecule barcode is 3' of the sample barcode. In some embodiments, for each unique oligonucleotide species, the sample barcode is 3' of the molecule barcode.

In some embodiments, each unique oligonucleotide species has a length of at least 24 nucleotides. In some embodiments, each unique oligonucleotide species has a length of 24-140 nucleotides.

In some embodiments, each pool comprises at least 1000 unique oligonucleotide species. In some embodiments, each pool comprises at least 6,500 unique oligonucleotide species. In some embodiments, each pool comprises at least 65,000 unique oligonucleotide species.

In some embodiments, at least 48 unique samples are each contacted with a different pool of unique oligonucleotide species. For example, at least 48, 72, 96, 120, 144, 168, or 192 samples can each be contacted with a different pool. For example each sample can be contacted with a different pool of unique oligonucleotide species in a well of a multi-well plate.

In some embodiments, at least 99% of the samples comprise no more than one cell each. For example, at least 99%, 99.5%, 99.9%, or 99.99% of the samples can comprise no more than one cell. By way of example, a solution comprising multiple cells can be diluted to an appropriate concentration so that there is a suitably high probability that each sample comprises no more than one cell.

In some embodiments, the unique oligonucleotide species of each pool are immobilized on a substrate, so that the sample barcodes but not the molecule barcodes are the same for the unique oligonucleotide species immobilized on each substrate. As such, each pool can be identified by a particular sample barcode. It is noted that different substrates (and as such, different pools) can be associated with different sample barcodes. In some embodiments, the substrate comprises a spatially isolated region of a surface, so that the substrates of different pools comprise the different spatially isolated regions of the surface. In some embodiments, the substrate comprises a well in a multi-well plate. In some embodiments, the substrate comprises a bead.

In some embodiments, the unique oligonucleotide species further comprises an adapter configured to immobilize the unique oligonucleotide on the substrate, wherein said barcode region is 3' of the adapter. Optionally, each adapter can comprise a universal priming site, for example for use in sequencing.

Methods of Making Compositions Comprising Unique Oligonucleotide Species

In accordance with some embodiments herein, methods of making a composition comprising unique oligonucleotides are described. The method can comprise providing a plurality of different sample barcodes as described herein. The method can comprise providing a plurality of different molecule barcodes as described herein. The method can comprise synthesizing a plurality of unique oligonucleotide species as described herein, in which each unique oligonucleotide species comprises a barcode region comprising a sample barcode and a molecule barcode as described herein. The method can comprise disposing the plurality of unique oligonucleotide species in spatially-isolated pools. Each pool can comprises multiple unique oligonucleotide species, so that the unique oligonucleotide species of the same pool comprise the same sample barcode sequence, and so that different unique oligonucleotide species of the same pool comprise different molecule barcode sequences. Optionally, the unique oligonucleotide species are disposed in the spatially-isolated pools concurrent with synthesis. Optionally, the unique oligonucleotide species are disposed in the spatially-isolated pools after synthesis. Optionally, the composition consists essentially of unique oligonucleotide species in which each molecular barcode has a G content of less than 50%. Optionally, the molecule barcodes of all of the unique oligonucleotide species collectively have a G content of no more than 12.5%. Optionally, the composition consists essentially of unique oligonucleotide species in which each molecular barcode has a G content of less than 50 and the molecule barcodes of all of the unique oligonucleotide species collectively have a G content of no more than 12.5%. In some embodiments, each spatially-isolated pool comprises at least 100 unique oligonucleotide species, for example, at least 100, 200, 300, 400, 500, 1000, 2000, 3000, 5000, 6500, or 65,000 unique oligonucleotide species. In some embodiments, each spatially-isolated pool comprises at least 1000 unique oligonucleotide species.

The unique oligonucleotides can be synthesized using any of a number of suitable methods. In some embodiments, the sample barcode sequences and molecule barcode sequences are generated in silico, and unique oligonucleotide species comprising the sample barcode sequences and molecule barcode sequences together are synthesized, for example using chemical oligonucleotide synthesis. In some embodiments, a plurality of oligonucleotides comprising the same sample barcode sequence are pooled in spatial isolation, and joined with a plurality of oligonucleotides comprising molecule barcodes, for example via hybridization and extension, or via ligation. Such an approach can be performed in multiple spatially isolated environments in parallel, or sequentially, to achieve multiple unique oligonucleotide species.

Optionally, each unique oligonucleotide species further comprises a uniform region 3' of the barcode region as described herein. Optionally, the uniform region comprises a target-specific region. In some embodiments, the target-specific region comprises at least 10 nucleotides complementary to a target nucleic acid (e.g., at least 10, 11, 12, 13, 14, 15, 16, 17, 18, 19, 20, 21, 22, 23, 24, 25, 26, 27, 28, 29, or 30 nucleotides complementary to the target, including ranges between any two of the listed values), and configured for 5' to 3' amplification of the target nucleic acid sequence. Optionally, the uniform region comprises an oligo dT sequence.

In some embodiments, the plurality of molecule barcodes (and as such, the plurality of unique oligonucleotide species) consists essentially of unique oligonucleotide species in which each molecular barcode has a G content of no more than 50% as described herein, for example, less than 50% G, 45% G, 40% G, 35% G, 30% G, 25% G, 20% G, 15% G, 12.5% G, 10% G, 7.5% G, 5% G, or 2.5% G content, or 0% G content. In some embodiments, the molecule barcodes of at least 95% of the unique oligonucleotide species have a G content of no more than 50% as described herein, for example, less than 50% G, 45% G, 40% G, 35% G, 30% G, 25% G, 20% G, 15% G, 12.5% G, 10% G, 7.5% G, 5% G, or 2.5% G content, or 0% G content. In some embodiments, the molecule barcodes of at least 99% of the unique oligonucleotide species have a G content of no more than 50% as described herein, for example, less than 50% G, 45% G, 40% G, 35% G, 30% G, 25% G, 20% G, 15% G, 12.5% G, 10% G, 7.5% G, 5% G, or 2.5% G content, or 0% G content. In some embodiments, all of the molecule barcodes of the unique oligonucleotide species have molecule barcodes having a G content of no more than 50% as described herein, for example, less than 50% G, 45% G, 40% G, 35% G, 30% G, 25% G, 20% G, 15% G, 12.5% G, 10% G, 7.5% G, 5% G, or 2.5% G content, or 0% G content. In some embodiments, each molecule barcode of each unique oligonucleotide species has a G content of no more than 50%, for example, less than 50% G, 45% G, 40% G, 35% G, 30% G, 25% G, 20% G, 15% G, 12.5% G, 10% G, 7.5% G, 5% G, or 2.5% G content, or 0% G content.

In some embodiments, the molecule barcodes of all of the unique oligonucleotide species in the plurality of unique oligonucleotide species collectively have a G content of no more than 50% G, for example, less than 50%, 45% G, 40% G, 35% G, 30% G, 25% G, 20% G, 15% G, 12.5% G, 10% G, 7.5% G, 5% G, or 2.5% G, or 0% G, including ranges between any two of the listed values. In some embodiments, the molecule barcodes of all of the unique oligonucleotide species in the plurality of unique oligonucleotide species collectively have a G content of no more than 12.5%.

In some embodiments, each sample barcode has a G content of 50% or less as described herein, for example, less than 50%, 45% G, 40% G, 35% G, 30% G, 25% G, 20% G, 15% G, 12.5% G, 10% G, 7.5% G, 5% G, or 2.5% G content, or 0% G content.

In some embodiments, the sample barcodes of all of the unique oligonucleotide species in the plurality of unique oligonucleotide species collectively have a G content of no more than 50% G, for example, less than 50%, 45% G, 40% G, 35% G, 30% G, 25% G, 20% G, 15% G, 12.5% G, 10% G, 7.5% G, 5% G, or 2.5% G, or 0% G, including ranges between any two of the listed values. In some embodiments, the sample barcodes of all of the unique oligonucleotide species in the plurality of unique oligonucleotide species collectively have a G content of no more than 12.5%.

In some embodiments, for at least 95% (e.g., at least 95%, 96%, 97%, 98%, 99%, 99.5%, 99.9%, or 99.99%) of the of the unique oligonucleotide species, any G in the molecule barcode is not adjacent to another G. In some embodiments, the plurality of unique oligonucleotide species consists essentially of unique oligonucleotide species for which any G in the molecule barcode is not adjacent to another G.

In some embodiments, at least 95% of the molecule barcodes of the unique oligonucleotide species comprise the sequence HNHNHNHN, in which each "H" is any one of A, C, or T, and in which each "N" is any one of A, G, C, or T. For example at least 95%, 96%, 97,%, 98%, 99%, 99.5%, 99.9%, or 99.99% of the molecule barcodes of the unique oligonucleotide species can comprise the sequence HNHNHNHN. It is noted that each H can be the same as, or different from any other H, and that each N can be the same as, or different from any other N. In some embodiments, each molecule barcode of the unique oligonucleotide species comprises the sequence HNHNHNHN.

In some embodiments, at least 99% of the molecule barcodes of the unique oligonucleotide species comprise molecule barcodes comprising the sequence HHHHHHHH, in which each "H" is any one of A, C, or T. For example at least 95%, 96%, 97,%, 98%, 99%, 99.5%, 99.9%, or 99.99% of the molecule barcodes of the unique oligonucleotide species can comprise the sequence HHHHHHHH. It is noted that each H can be the same as, or different from any other H. In some embodiments, each molecule barcode of the unique oligonucleotide species comprises the sequence HHHHHHHH.

In some embodiments, each unique oligonucleotide species comprises a spacer 3' of the barcode region and 5' of the target specific region. Optionally, the spacer can comprise the sequence HNH, in which each "H" is any one of A, C, or T, and in which each "N" is any one of A, G, C, or T. Optionally, the spacer can comprise the sequence HHH. Optionally, the spacer can comprise the sequence HNHNHNHN. Optionally, the spacer can comprise the sequence HHHHHHHH. It is noted that each H can be the same as, or different from any other H, and that each N can be the same as, or different from any other N. In some embodiments, each unique oligonucleotide species comprises a spacer 3' of the barcode region and 5' of the target specific region, said spacer comprising the sequence HNHNHNHN, in which each "H" is any one of A, C, or T, and in which each "N" is any one of A, G, C, or T. In some embodiments, unique oligonucleotide comprises a spacer 3' of the barcode region and 5' of the target specific region, the spacer comprising the sequence HHHHHHHH, in which each "H" is any one of A, C, or T.

In some embodiments, at least one pool comprises least two oligonucleotides of the same unique oligonucleotide species. In some embodiments, no pool comprises two oligonucleotides of the same unique oligonucleotide species.

In some embodiments, the target-specific region can comprise a sequence for 5' to 3' amplification of a target nucleic acid. In some embodiments, the target specific region comprises an oligo dT sequence. In some embodiments, the target specific region comprises a sequence flanking a sequence encoding a variable region of an immune cell receptor or immunoglobulin.

In some embodiments, for each unique oligonucleotide species, the molecule barcode is 3' of the sample barcode. In some embodiments, for each unique oligonucleotide species, the sample barcode is 3' of the molecule barcode.

In some embodiments, each unique oligonucleotide species has a length of at least 24 nucleotides. In some embodiments, each unique oligonucleotide species has a length of 24-140 nucleotides.

In some embodiments, each pool comprises at least 6,500 unique oligonucleotide species. In some embodiments, each pool comprises at least 65,000 unique oligonucleotide species.

In some embodiments, the method further comprises immobilizing the unique oligonucleotide species of each spatially-distinct pool on a substrate, so that the sample barcodes but not the molecule barcodes are the same for the unique oligonucleotide species immobilized on each substrate. As such, each pool can be identified by a particular sample barcode. It is noted that different substrates (and as such, different pools) can be associated with different sample barcodes. In some embodiments, the substrate comprises a discrete region of a surface, so that the substrates of different pools comprise the different discrete regions of the surface. In some embodiments, the substrate comprises a well in a multi-well plate. In some embodiments, the substrate comprises a bead. In some embodiments, the unique oligonucleotide species are immobilized on the substrate by a covalent bond. In some embodiments, the unique oligonucleotide species are immobilized on the substrate by a magnetic or electromagnetic force. In some embodiments, the unique oligonucleotide species are imbedded in the substrate, so as to immobilize them on the substrate.

In some embodiments, at least 48 spatially-distinct pools are made, for example at least 48, 72, 96, 120, 144, 168, or 192 spatially-distinct pools.

In some embodiments, the unique oligonucleotide species are disposed in spatially-isolated pools concurrent with said synthesis. In some embodiments, the unique oligonucleotide species are disposed in spatially-isolated pools after said synthesis.

Oligonucleotides

In some embodiments, an oligonucleotide comprising a barcode region 3' of the adapter region is described. The barcode region can comprise a molecule barcode as described herein, in which the molecule barcode has a G content of no more than 50%. The molecule barcode can comprise at least 7 nucleotides.

In some embodiments, the oligonucleotide further comprises a sample barcode as described herein. The sample barcode can comprise at least 3 nucleotides.

In some embodiments, the oligonucleotide further comprises a uniform region 3' of the barcode region. In some embodiments, the uniform region comprises a target-specific region comprising at least 10 nucleotides complementary to a target nucleic acid as described herein. In some embodiments, the uniform region comprises an oligo dT sequence. In some embodiments, the oligonucleotide further comprises an adapter region 5' of the barcode region. In some embodiments, the oligonucleotide further comprises a spacer 3' of the barcode region and 5' of the uniform region as described herein.

Alternative Embodiments

Figures 1A, 1B, 1C:
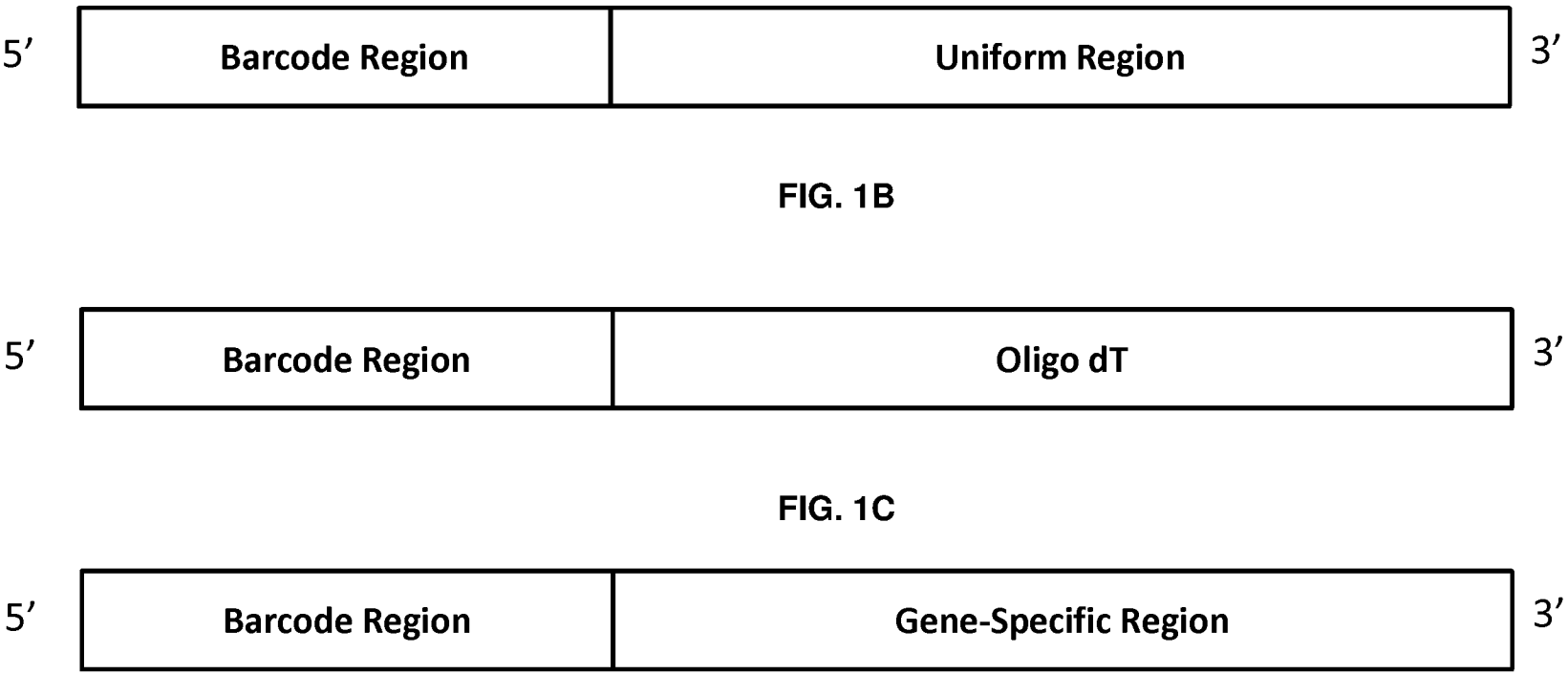
FIG. 1A is a schematic diagram illustrating an oligonucleotide species comprising a barcode region 5' of a uniform region, in accordance with some embodiments herein.
FIG. 1B is a schematic diagram illustrating an oligonucleotide species comprising a barcode region 5' of an oligo dT sequence, in accordance with some embodiments herein.
FIG. 1C is a schematic diagram illustrating an oligonucleotide species comprising a barcode region 5' of a gene-specific region, in accordance with some embodiments herein.

In some embodiments, designs for accurate and unbiased barcoding of nucleic acid transcripts are provided. These primer designs are composed of nucleic acid sequences (DNA, RNA, or LNA) that can target specific nucleic acid (DNA/RNA) transcripts via a gene-specific approach, or target a large set of nucleic acid transcripts (e.g. via poly-A tail of messenger RNAs or other consensus sequences) (FIGS. 1A-C). Along with the target sequences, these primers include two categories of nucleic acid barcodes: 1) molecule barcodes, also called "molecular barcodes," Molecular Index (MI) or Unique Molecular Identifier (UMI) and 2) sample barcodes, also called Sample Index (SI) (FIGS. 1A-C). The MI and SI barcodes are used to uniquely label for identification of its original target transcript via the MI, and its sample origin (SI) after library preparation for next generation sequencing or other sequence readout and barcode readout methods. Some embodiments detail different arrangements of MI and SIs within the primer that ensure unbiased and random labelling of barcodes to target transcripts for accurate gene expression profiling (see, e.g. FIGS. 3A-3H) (see Fu et al. 2011 PNAS 108: 9026-9032, hereby incorporated by reference in its entirety for discussion of random labelling).

In some embodiments, designs unique primer designs that can reduce 'barcode bias,' which is a phenomenon that is observed in the prior art designs, whereby with barcodes with high G-nucleotide content is more oftenly used compared to other barcode compositions (FIG. 4). In certain cases where conventional primers are used to target and label mRNA transcripts using a gene-specific sequence, MIs with high % G content and multiple G's are preferably observed (FIG. 4). Moreover, without being limited by any theory, in conventional designs, SIs associated with no target genes observes small amounts of PCR errors due to these primers cross reacting during a sample multiplex PCR (FIGS. 4-5). These crossover events often happen with primers with high % G content and multiple G's, possibly due unique secondary structure called "G-Quaduplexes" in G-rich oligonucleotides. Because these G-rich MI/SI primers can form inter- and intra-molecular complexes with one another, conventional DNA cleanup steps to remove primers (e.g. Ampure XP beads) may not be sufficient. To minimize these events from happening, this invention entails several designs that reduces primer G content to minimize 'barcode bias' and the primer crossover are provided (FIGS. 3A-3H).

FIGS. 3A-3H show the design of prior art barcode layout (FIG. 3A) and novel designs to minimize bias as described (FIGS. 3B-H). In FIG. 3A, the conventional design allows for either the MI composition of 'BBBBBBV' or 'NNNNNNNN' (B is C,G, or T; V is A,C, or G; N is A,T,G, or C). A subset of the prior design MI barcode would be G-rich. In panel 3B-C, addition of either TTT or TTTTT after the MI to reduce G-richness along the region (length of non-G spacers can be variable, and can be any non-G nucleotide). In FIG. 3D, SI and MI positions are switched, so that high G-rich MIs would not be adjacent to potentially G-rich gene specific target regions. In FIGS. 3E-F, addition of either TTT or TTTTT to FIG. 3D design to further reduce G-rich regions (note that SIs are not G-rich, and the length of non-G spacers can be variable and can be any non-G nucleotide). In FIGS. 3G-H designs, MIs are designed to not be G-rich by using 'HHHHHHHH' or 'HNHNHNHN,' where H is A, C, or T.

The G-rich drawbacks of conventional designs are most observed gene-specific targeting method is used. Some embodiments include the use of the new primer designs in gene-specific target panels, such as T cell receptors (TCR), where primers are used to target TCR-specific sequences. Designs in accordance with some embodiments herein can alleviate SI barcode crossover, thereby reducing the 'noise' of a TCR molecular barcoding assay.

Example 1: Accurate Analysis of Sample Target Nucleic Acids Using Unique Oligonucleotide Species 96 formats of unique oligonucleotide species were designed, the sequences of which are summarized in FIGS. 5A-5E (SEQ ID NOs: 1-96). Unique oligonucleotide species formats A01-A12 (SEQ ID NOs: 1-12) were provided as controls, in which the molecule barcode ("2nd bc") was NNNNNNNN. As such, the molecule barcodes of these control unique oligonucleotide species did not have any constraints or limits on the G content. Unique oligonucleotide species formats B01-B12 (SEQ ID NOs: 13-24) comprised a spacer of the sequence TTT 3' of the molecule barcode ("2nd bc") and 5' of the uniform region ("5 to 3' recognition sequence"). Unique oligonucleotide species formats C01-C12 (SEQ ID NOs: 25-36) comprised a spacer of the sequence TTTTT 3' of the molecule barcode ("2nd bc") and 5' of the uniform region ("5 to 3' recognition sequence"). Unique oligonucleotide species formats D01-D12 (SEQ ID NOs: 37-48) comprised a molecule barcode ("1st bc") 5' of the sample barcode ("2nd bc"). Unique oligonucleotide species formats E01-E12 (SEQ ID NOs: 49-60) comprised a molecule barcode ("1st bc") 5' of the sample barcode ("2nd bc") and a spacer of the sequence TTT 3' of the barcode region and 4' of the uniform region. Unique oligonucleotide species formats F01-F12 (SEQ ID NOs: 61-72) comprised a molecule barcode ("1st bc") 5' of the sample barcode ("2nd bc") and a spacer of the sequence TTTTT 3' of the barcode region and 4' of the uniform region. Unique oligonucleotide species formats G01-G12 (SEQ ID NOs: 73-84) comprised molecule barcodes ("2nd bc") each comprising the sequence HHHHHHHH (in which each "H" is an A, C, or T, and in which any two "H" nucleotides can be the same of different). Unique oligonucleotide species formats H01-H12 (SEQ ID NOs: 85-96) comprised molecule barcodes ("2nd bc") each comprising the sequence HNHNHNHN (in which each "H" is an A, C, or T, and in which any two "H" nucleotides can be the same of different, and in which each "N" can be A, G, C, or, T, and in which any two "N" nucleotides can be the same or different).

Amplification and analysis of target T cell receptor nucleic acid sequences was performed as follows: the Precise™ TCR Encoding Plate (BD Cellular Research Inc.) was thawed at room temperature and spun briefly to collect the 5 μL reagents in each well. The plate was placed on ice in a 96 well rack and very carefully remove the seal, while avoiding disturbing reagents in the wells. Cells were sorted or added directly into the 96 well encoding plate (1 cell per well). The plate was sealed and vortexed briefly (5-10 s) to mix the reagents, and then spun briefly (~1000 rpm×10 s). The sorted sample plates can optionally be stored at −80° C. until ready to start the Precise™ protocol. For reverse transcription, the plate was incubated at 65° C. for 3 min, cooled to 4° C., and then placed on ice for 5 min. The reaction master mix was as follows:

TABLE 1

| Reagent | Per well | 1 Plate MM |
|---|---|---|
| Nuclease Free Water | 2.7 | 324.0 |
| 5X Precise Reverse Transcription Buffer | 2.0 | 240 |
| Precise RNase Inhibitor | 0.1 | 12.0 |
| Precise Reverse Transcriptase | 0.2 | 24 |

5 uL of RT MM were pipetted to each well. Each plate was sealed, and a reverse-transcriptase program was run: 42° C., 30 min; 80 C, 5 min; 4 C pause.

cDNA purification was performed using the following protocol: Spin the plate (1000 rpm×10 s). Combine all reactions into a single 2 mL tube. Add 8 uL of Precise DBP Mix into the pooled cDNA tube. Vortex gently to get buffer into solution. Add an equivalent volume of AMPure XP beads to the single tube containing the pooled RT reaction product (1× volume of pooled PCR product). Pipette up and down to mix the sample and beads. Incubate bead mix at room temperature for 5 minutes. Open the cap to make sure the beads aren't disturbed. Place tube on magnet and wait until the liquid and beads separate. The liquid should be entirely clear before it is removed. This may take up to 5 min. Keeping the tube on the magnet, carefully remove only the liquid and discard. Keeping the tube on the magnet stand, gently rinse the beads once using 2 mL of 70% EtOH/30% $H_2O$. Prepare fresh EtOH solution each day to avoid evaporation. Care can be taken not to disturb or re-suspend the beads during the rinse step. Immediately remove all residual EtOH solution with a pipette. While the tube is on the magnet, tap to collect as much of the EtOH as possible at the bottom of the tube. To elute the product from the beads, remove the tube from the magnet. Transfer 68 μL of Elution Buffer into the tube containing the beads. Wet the beads with the elution buffer by tilting the tube. Vortex well to mix and wait 1 min. Return the tube to the magnet. Wait until the solution is clear, typically <5 min. Recover the purified PCR product solution by carefully pipetting the solution away from the beads. Transfer the clear liquid product (68 μL) to a new 1.5 mL tube.

PCR N1 amplification (target amplification) was performed using the following protocol: Prepare PCR mix (200 uL) in pre-amplification area according to Table 2:

TABLE 2

| Reagent | Per sample |
|---|---|
| RT Product | 68 |
| 2X OneTaq HotStart | 100 |
| Precise TCR N1 Primer Pool | 12 |
| 10 uM N1R Primer | 20 |
| Total | 200 |

Split this 200 uL reaction mix into 4 PCR tubes. Run 20 cycles of the following PCR conditions: 3-minute annealing time at 60 C, 1-minute extension time at 68 C (About 2 hours). Combine all PCR products into one sample tube. Add 160 uL of Ampure beads (0.8×), pipette to mix well, and incubate for 5 minutes at RT. Place tube on magnet and wait until the liquid and beads separate. The liquid should be entirely clear before it is removed. This may take up to 5 min. Remove only the liquid and discard. Gently rinse the tube once while on the magnet stand with 1 mL of 70%

EtOH/30% $H_2O$. Do not re-suspend the beads during the rinse step. Immediately remove all residual EtOH with a pipette. While the tube is on the magnet, tap to collect as much of the EtOH as possible at the bottom of the tube. Elute PCR product in 50 uL Elution Buffer.

PCR N1 amplification (adapter and indexing PCR) was performed using the following protocol: Prepare PCR mix (50 uL) according to Table 3:

TABLE 3

| Reagent | Per sample |
|---|---|
| Water | 7.75 |
| 2X OneTaq HotStart | 25 |
| Precise Indexing Primer Set (D70x) | 1.25 |
| Precise TCR N2 Primer Pool | 6 |
| PCR N1 Product | 10 |

Run 25 cycles of the following PCR conditions: 3-minute annealing at 60 C, 1 min extension time at 68 C. Purify at 0.8× Ampure twice, elute in 30 uL of Elution Buffer.

Figure 6:
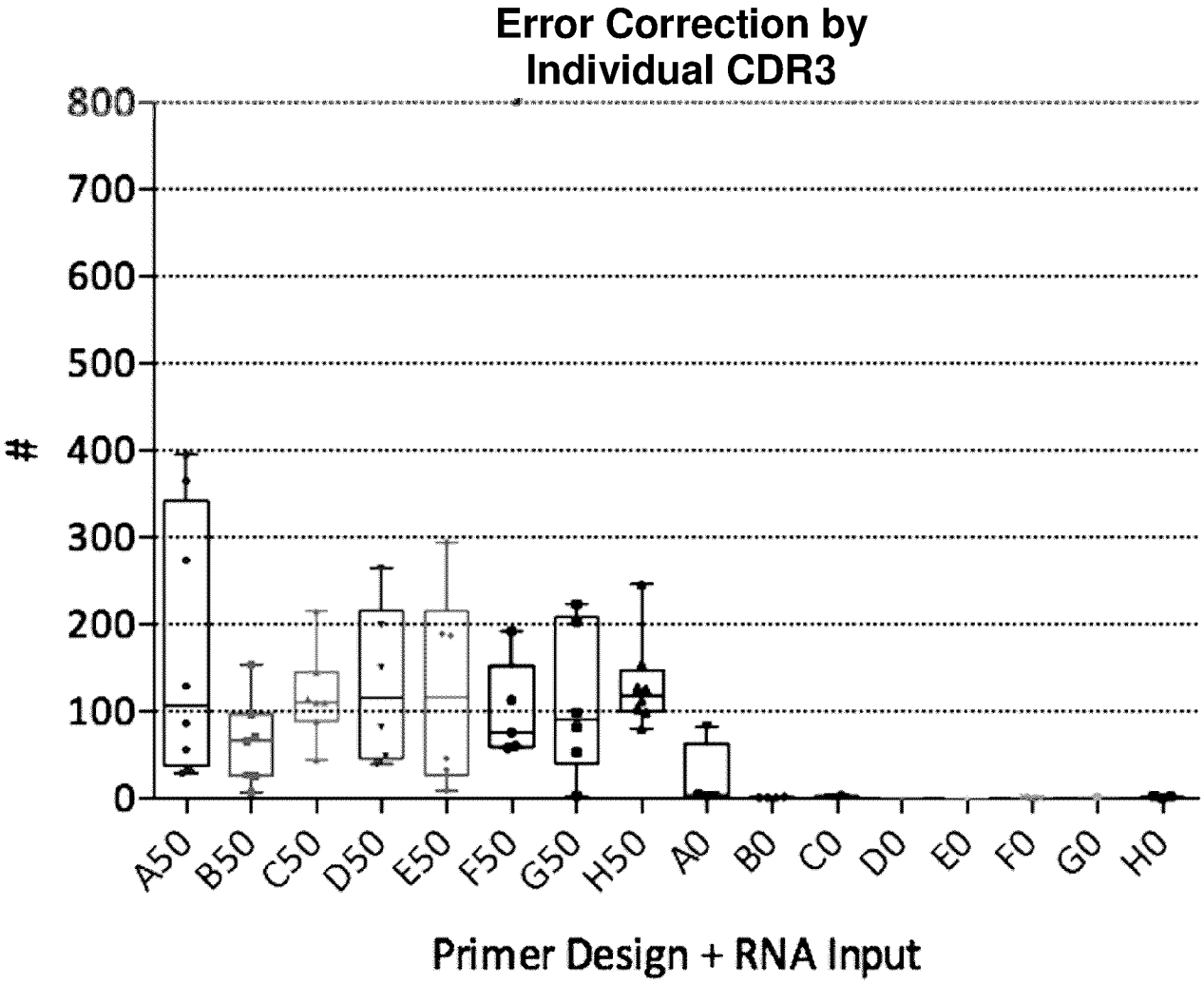
FIG. 6 is a graph of error correction by individual for an analysis using unique oligonucleotide species in accordance with some embodiments herein.
Figure 7:
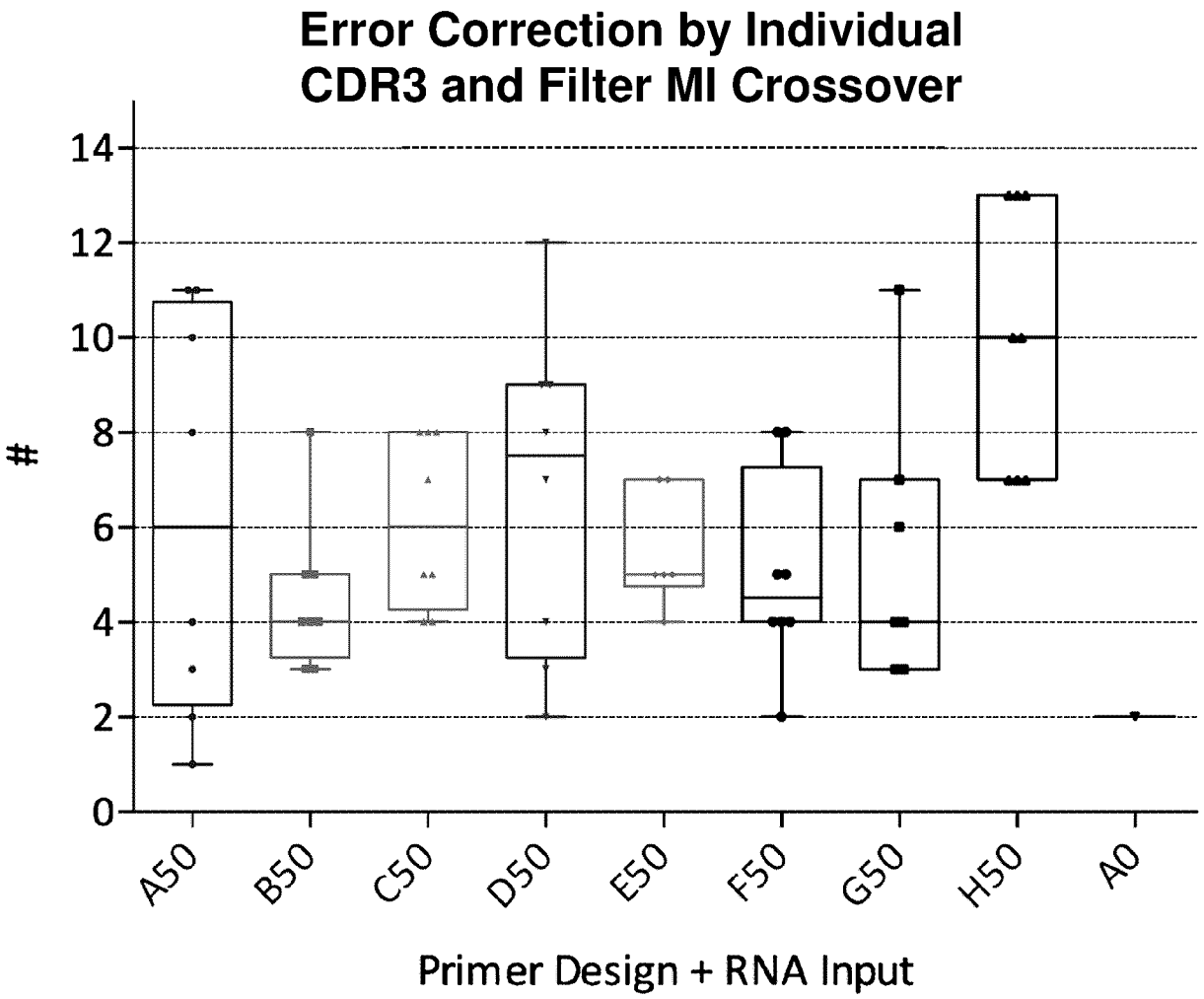
FIG. 7 is a graph of error correction by individual and filter MI crossover for an analysis using unique oligonucleotide species in accordance with some embodiments herein.

FIG. 6 shows error correction for the average of sequence results (by individual TCRa CDR3). In FIG. 6, the Y axis plots the number of different molecule barcodes detected for TCRa.

Results are shown for reactions with 50 pg of target RNA (denoted as "50" in FIG. 6, e.g., A50, B50, C50, D50, E50, F50, G50) and negative controls that received 0 pg of target RNA (denoted as "0" in FIG. 6, e.g., A0, B0, C0, D0, E0, F0, G0). As such, 0 pg serves as a negative control and detector of assay noise that is leaked from 50 pg sample. For the reactions that received target RNA, unique oligonucleotide designs in accordance with some embodiments herein B01-B12 ("B50"), C01-C12 ("C50"), D01-D12 ("D50"), E01-E12 ("E50"), F01-F12 ("F50"), G01-G12 ("G50"), and H01-H12 ("H50") had lower error rates than conventional formats A01-A12 ("A50"). In particular, for for TRAC in this experiment, format "H" had the highest sensitivity with low noise and performed better than the original barcoded primers (A).

Thus, compositions comprising unique oligonucleotide species comprising barcode regions, and molecule barcodes having a relatively low G content, and/or unique oligonucleotides comprising a spacer 3' of the molecule barcode and 5' of the uniform region as described herein yielded amplification with a lower error rate, and thus higher accuracy than compositions comprising general polynucleotide species that did not comprise such features.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof.

Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

SEQUENCE LISTING

```
Sequence total quantity: 97
SEQ ID NO: 1            moltype = DNA  length = 49
FEATURE                 Location/Qualifiers
misc_difference         29..36
                        note = a, c, g, or t
source                  1..49
                        mol_type = other DNA
                        organism = synthetic construct
misc_feature            1..49
                        note = Synthetic nucleotide
SEQUENCE: 1
acacgacgct cttccgatct acagtgctnn nnnnnncaga cagacttgt              49

SEQ ID NO: 2            moltype = DNA  length = 49
FEATURE                 Location/Qualifiers
misc_difference         29..36
                        note = a, c, g, or t
source                  1..49
                        mol_type = other DNA
                        organism = synthetic construct
misc_feature            1..49
                        note = Synthetic nucleotide
SEQUENCE: 2
acacgacgct cttccgatct acatgcgtnn nnnnnncaga cagacttgt              49

SEQ ID NO: 3            moltype = DNA  length = 49
FEATURE                 Location/Qualifiers
misc_difference         29..36
                        note = a, c, g, or t
source                  1..49
                        mol_type = other DNA
                        organism = synthetic construct
misc_feature            1..49
                        note = Synthetic nucleotide
SEQUENCE: 3
acacgacgct cttccgatct accgattgnn nnnnnncaga cagacttgt              49

SEQ ID NO: 4            moltype = DNA  length = 49
FEATURE                 Location/Qualifiers
misc_difference         29..36
                        note = a, c, g, or t
source                  1..49
                        mol_type = other DNA
                        organism = synthetic construct
misc_feature            1..49
                        note = Synthetic nucleotide
SEQUENCE: 4
acacgacgct cttccgatct accttgagnn nnnnnncaga cagacttgt              49

SEQ ID NO: 5            moltype = DNA  length = 49
FEATURE                 Location/Qualifiers
misc_feature            1..49
                        note = Synthetic nucleotide
source                  1..49
                        mol_type = other DNA
                        organism = synthetic construct
misc_difference         29..36
                        note = a, c, g, or t
SEQUENCE: 5
acacgacgct cttccgatct acgatgtcnn nnnnnncaga cagacttgt              49

SEQ ID NO: 6            moltype = DNA  length = 49
FEATURE                 Location/Qualifiers
```

```
misc_feature           1..49
                       note = Synthetic nucleotide
source                 1..49
                       mol_type = other DNA
                       organism = synthetic construct
misc_difference        29..36
                       note = a, c, g, or t
SEQUENCE: 6
acacgacgct cttccgatct acgtatgcnn nnnnnncaga cagacttgt              49

SEQ ID NO: 7           moltype = DNA  length = 49
FEATURE                Location/Qualifiers
misc_feature           1..49
                       note = Synthetic nucleotide
source                 1..49
                       mol_type = other DNA
                       organism = synthetic construct
misc_difference        29..36
                       note = a, c, g, or t
SEQUENCE: 7
acacgacgct cttccgatct actctggann nnnnnncaga cagacttgt              49

SEQ ID NO: 8           moltype = DNA  length = 49
FEATURE                Location/Qualifiers
misc_feature           1..49
                       note = Synthetic nucleotide
source                 1..49
                       mol_type = other DNA
                       organism = synthetic construct
misc_difference        29..36
                       note = a, c, g, or t
SEQUENCE: 8
acacgacgct cttccgatct actggctann nnnnnncaga cagacttgt              49

SEQ ID NO: 9           moltype = DNA  length = 49
FEATURE                Location/Qualifiers
misc_feature           1..49
                       note = Synthetic nucleotide
source                 1..49
                       mol_type = other DNA
                       organism = synthetic construct
misc_difference        29..36
                       note = a, c, g, or t
SEQUENCE: 9
acacgacgct cttccgatct agaccttgnn nnnnnncaga cagacttgt              49

SEQ ID NO: 10          moltype = DNA  length = 49
FEATURE                Location/Qualifiers
misc_feature           1..49
                       note = Synthetic nucleotide
source                 1..49
                       mol_type = other DNA
                       organism = synthetic construct
misc_difference        29..36
                       note = a, c, g, or t
SEQUENCE: 10
acacgacgct cttccgatct agattccgnn nnnnnncaga cagacttgt              49

SEQ ID NO: 11          moltype = DNA  length = 49
FEATURE                Location/Qualifiers
misc_feature           1..49
                       note = Synthetic nucleotide
source                 1..49
                       mol_type = other DNA
                       organism = synthetic construct
misc_difference        29..36
                       note = a, c, g, or t
SEQUENCE: 11
acacgacgct cttccgatct agccgaccnn nnnnnncaga cagacttgt              49

SEQ ID NO: 12          moltype = DNA  length = 49
FEATURE                Location/Qualifiers
misc_feature           1..49
                       note = Synthetic nucleotide
source                 1..49
                       mol_type = other DNA
                       organism = synthetic construct
misc_difference        29..36
                       note = a, c, g, or t
```

```
SEQUENCE: 12
acacgacgct cttccgatct agcgctgcnn nnnnnncaga cagacttgt              49

SEQ ID NO: 13          moltype = DNA  length = 52
FEATURE                Location/Qualifiers
misc_feature           1..52
                       note = Synthetic nucleotide
misc_difference        29..36
                       note = a, c, g, or t
source                 1..52
                       mol_type = other DNA
                       organism = synthetic construct
SEQUENCE: 13
acacgacgct cttccgatct agctagtcnn nnnnnnnttc agacagactt gt          52

SEQ ID NO: 14          moltype = DNA  length = 52
FEATURE                Location/Qualifiers
misc_feature           1..52
                       note = Synthetic nucleotide
misc_difference        29..36
                       note = a, c, g, or t
source                 1..52
                       mol_type = other DNA
                       organism = synthetic construct
SEQUENCE: 14
acacgacgct cttccgatct aggctctann nnnnnnnttc agacagactt gt          52

SEQ ID NO: 15          moltype = DNA  length = 52
FEATURE                Location/Qualifiers
misc_feature           1..52
                       note = Synthetic nucleotide
misc_difference        29..36
                       note = a, c, g, or t
source                 1..52
                       mol_type = other DNA
                       organism = synthetic construct
SEQUENCE: 15
acacgacgct cttccgatct aggtctcann nnnnnnnttc agacagactt gt          52

SEQ ID NO: 16          moltype = DNA  length = 52
FEATURE                Location/Qualifiers
misc_feature           1..52
                       note = Synthetic nucleotide
misc_difference        29..36
                       note = a, c, g, or t
source                 1..52
                       mol_type = other DNA
                       organism = synthetic construct
SEQUENCE: 16
acacgacgct cttccgatct agtactatnn nnnnnnnttc agacagactt gt          52

SEQ ID NO: 17          moltype = DNA  length = 52
FEATURE                Location/Qualifiers
misc_feature           1..52
                       note = Synthetic nucleotide
misc_difference        29..36
                       note = a, c, g, or t
source                 1..52
                       mol_type = other DNA
                       organism = synthetic construct
SEQUENCE: 17
acacgacgct cttccgatct agtcagctnn nnnnnnnttc agacagactt gt          52

SEQ ID NO: 18          moltype = DNA  length = 52
FEATURE                Location/Qualifiers
misc_feature           1..52
                       note = Synthetic nucleotide
misc_difference        29..36
                       note = a, c, g, or t
source                 1..52
                       mol_type = other DNA
                       organism = synthetic construct
SEQUENCE: 18
acacgacgct cttccgatct agtgtcgtnn nnnnnnnttc agacagactt gt          52

SEQ ID NO: 19          moltype = DNA  length = 52
FEATURE                Location/Qualifiers
misc_feature           1..52
                       note = Synthetic nucleotide
```

```
misc_difference        29..36
                       note = a, c, g, or t
source                 1..52
                       mol_type = other DNA
                       organism = synthetic construct
SEQUENCE: 19
acacgacgct cttccgatct atacgtgcnn nnnnnnnttc agacagactt gt          52

SEQ ID NO: 20          moltype = DNA  length = 52
FEATURE                Location/Qualifiers
misc_feature           1..52
                       note = Synthetic nucleotide
misc_difference        29..36
                       note = a, c, g, or t
source                 1..52
                       mol_type = other DNA
                       organism = synthetic construct
SEQUENCE: 20
acacgacgct cttccgatct atagcgtcnn nnnnnnnttc agacagactt gt          52

SEQ ID NO: 21          moltype = DNA  length = 52
FEATURE                Location/Qualifiers
misc_feature           1..52
                       note = Synthetic nucleotide
misc_difference        29..36
                       note = a, c, g, or t
source                 1..52
                       mol_type = other DNA
                       organism = synthetic construct
SEQUENCE: 21
acacgacgct cttccgatct atcggtcann nnnnnnnttc agacagactt gt          52

SEQ ID NO: 22          moltype = DNA  length = 52
FEATURE                Location/Qualifiers
misc_feature           1..52
                       note = Synthetic nucleotide
misc_difference        29..36
                       note = a, c, g, or t
source                 1..52
                       mol_type = other DNA
                       organism = synthetic construct
SEQUENCE: 22
acacgacgct cttccgatct atctcggann nnnnnnnttc agacagactt gt          52

SEQ ID NO: 23          moltype = DNA  length = 52
FEATURE                Location/Qualifiers
misc_feature           1..52
                       note = Synthetic nucleotide
misc_difference        29..36
                       note = a, c, g, or t
source                 1..52
                       mol_type = other DNA
                       organism = synthetic construct
SEQUENCE: 23
acacgacgct cttccgatct atgacgctnn nnnnnnnttc agacagactt gt          52

SEQ ID NO: 24          moltype = DNA  length = 52
FEATURE                Location/Qualifiers
misc_feature           1..52
                       note = Synthetic nucleotide
misc_difference        29..36
                       note = a, c, g, or t
source                 1..52
                       mol_type = other DNA
                       organism = synthetic construct
SEQUENCE: 24
acacgacgct cttccgatct attccgagnn nnnnnnnttc agacagactt gt          52

SEQ ID NO: 25          moltype = DNA  length = 54
FEATURE                Location/Qualifiers
misc_feature           1..54
                       note = Synthetic nucleotide
misc_difference        29..36
                       note = a, c, g, or t
source                 1..54
                       mol_type = other DNA
                       organism = synthetic construct
SEQUENCE: 25
acacgacgct cttccgatct attgaccgnn nnnnnnnttt tcagacagac ttgt        54
```

```
SEQ ID NO: 26          moltype = DNA  length = 54
FEATURE                Location/Qualifiers
misc_feature           1..54
                       note = Synthetic nucleotide
misc_difference        29..36
                       note = a, c, g, or t
source                 1..54
                       mol_type = other DNA
                       organism = synthetic construct
SEQUENCE: 26
acacgacgct cttccgatct cagagttcnn nnnnnntttt tcagacagac ttgt        54

SEQ ID NO: 27          moltype = DNA  length = 54
FEATURE                Location/Qualifiers
misc_feature           1..54
                       note = Synthetic nucleotide
misc_difference        29..36
                       note = a, c, g, or t
source                 1..54
                       mol_type = other DNA
                       organism = synthetic construct
SEQUENCE: 27
acacgacgct cttccgatct cagccgacnn nnnnnntttt tcagacagac ttgt        54

SEQ ID NO: 28          moltype = DNA  length = 54
FEATURE                Location/Qualifiers
misc_feature           1..54
                       note = Synthetic nucleotide
misc_difference        29..36
                       note = a, c, g, or t
source                 1..54
                       mol_type = other DNA
                       organism = synthetic construct
SEQUENCE: 28
acacgacgct cttccgatct cagttagcnn nnnnnntttt tcagacagac ttgt        54

SEQ ID NO: 29          moltype = DNA  length = 54
FEATURE                Location/Qualifiers
misc_feature           1..54
                       note = Synthetic nucleotide
misc_difference        29..36
                       note = a, c, g, or t
source                 1..54
                       mol_type = other DNA
                       organism = synthetic construct
SEQUENCE: 29
acacgacgct cttccgatct catcgtgann nnnnnntttt tcagacagac ttgt        54

SEQ ID NO: 30          moltype = DNA  length = 54
FEATURE                Location/Qualifiers
misc_feature           1..54
                       note = Synthetic nucleotide
misc_difference        29..36
                       note = a, c, g, or t
source                 1..54
                       mol_type = other DNA
                       organism = synthetic construct
SEQUENCE: 30
acacgacgct cttccgatct catgcgtann nnnnnntttt tcagacagac ttgt        54

SEQ ID NO: 31          moltype = DNA  length = 54
FEATURE                Location/Qualifiers
misc_feature           1..54
                       note = Synthetic nucleotide
misc_difference        29..36
                       note = a, c, g, or t
source                 1..54
                       mol_type = other DNA
                       organism = synthetic construct
SEQUENCE: 31
acacgacgct cttccgatct ccagttagnn nnnnnntttt tcagacagac ttgt        54

SEQ ID NO: 32          moltype = DNA  length = 54
FEATURE                Location/Qualifiers
misc_feature           1..54
                       note = Synthetic nucleotide
misc_difference        29..36
                       note = a, c, g, or t
```

```
source                  1..54
                        mol_type = other DNA
                        organism = synthetic construct
SEQUENCE: 32
acacgacgct cttccgatct ccatggcgnn nnnnnntttt tcagacagac ttgt        54

SEQ ID NO: 33           moltype = DNA  length = 54
FEATURE                 Location/Qualifiers
misc_feature            1..54
                        note = Synthetic nucleotide
misc_difference         29..36
                        note = a, c, g, or t
source                  1..54
                        mol_type = other DNA
                        organism = synthetic construct
SEQUENCE: 33
acacgacgct cttccgatct ccgattgann nnnnnntttt tcagacagac ttgt        54

SEQ ID NO: 34           moltype = DNA  length = 54
FEATURE                 Location/Qualifiers
misc_feature            1..54
                        note = Synthetic nucleotide
misc_difference         29..36
                        note = a, c, g, or t
source                  1..54
                        mol_type = other DNA
                        organism = synthetic construct
SEQUENCE: 34
acacgacgct cttccgatct cgaccagcnn nnnnnntttt tcagacagac ttgt        54

SEQ ID NO: 35           moltype = DNA  length = 54
FEATURE                 Location/Qualifiers
misc_feature            1..54
                        note = Synthetic nucleotide
misc_difference         29..36
                        note = a, c, g, or t
source                  1..54
                        mol_type = other DNA
                        organism = synthetic construct
SEQUENCE: 35
acacgacgct cttccgatct cgagattcnn nnnnnntttt tcagacagac ttgt        54

SEQ ID NO: 36           moltype = DNA  length = 54
FEATURE                 Location/Qualifiers
misc_feature            1..54
                        note = Synthetic nucleotide
misc_difference         29..36
                        note = a, c, g, or t
source                  1..54
                        mol_type = other DNA
                        organism = synthetic construct
SEQUENCE: 36
acacgacgct cttccgatct cgattgacnn nnnnnntttt tcagacagac ttgt        54

SEQ ID NO: 37           moltype = DNA  length = 49
FEATURE                 Location/Qualifiers
misc_feature            1..49
                        note = Synthetic nucleotide
misc_difference         21..28
                        note = a, c, g, or t
source                  1..49
                        mol_type = other DNA
                        organism = synthetic construct
SEQUENCE: 37
acacgacgct cttccgatct nnnnnnnncg catgtacaga cagacttgt               49

SEQ ID NO: 38           moltype = DNA  length = 49
FEATURE                 Location/Qualifiers
misc_feature            1..49
                        note = Synthetic nucleotide
misc_difference         21..28
                        note = a, c, g, or t
source                  1..49
                        mol_type = other DNA
                        organism = synthetic construct
SEQUENCE: 38
acacgacgct cttccgatct nnnnnnnncg ctatgacaga cagacttgt               49

SEQ ID NO: 39           moltype = DNA  length = 49
```

```
FEATURE                 Location/Qualifiers
misc_feature            1..49
                        note = Synthetic nucleotide
misc_difference         21..28
                        note = a, c, g, or t
source                  1..49
                        mol_type = other DNA
                        organism = synthetic construct
SEQUENCE: 39
acacgacgct cttccgatct nnnnnnnncg tacatgcaga cagacttgt              49

SEQ ID NO: 40           moltype = DNA  length = 49
FEATURE                 Location/Qualifiers
misc_feature            1..49
                        note = Synthetic nucleotide
misc_difference         21..28
                        note = a, c, g, or t
source                  1..49
                        mol_type = other DNA
                        organism = synthetic construct
SEQUENCE: 40
acacgacgct cttccgatct nnnnnnnncg tcatagcaga cagacttgt              49

SEQ ID NO: 41           moltype = DNA  length = 49
FEATURE                 Location/Qualifiers
misc_feature            1..49
                        note = Synthetic nucleotide
misc_difference         21..28
                        note = a, c, g, or t
source                  1..49
                        mol_type = other DNA
                        organism = synthetic construct
SEQUENCE: 41
acacgacgct cttccgatct nnnnnnnnct acgacacaga cagacttgt              49

SEQ ID NO: 42           moltype = DNA  length = 49
FEATURE                 Location/Qualifiers
misc_feature            1..49
                        note = Synthetic nucleotide
misc_difference         21..28
                        note = a, c, g, or t
source                  1..49
                        mol_type = other DNA
                        organism = synthetic construct
SEQUENCE: 42
acacgacgct cttccgatct nnnnnnnnct agctgacaga cagacttgt              49

SEQ ID NO: 43           moltype = DNA  length = 49
FEATURE                 Location/Qualifiers
misc_feature            1..49
                        note = Synthetic nucleotide
misc_difference         21..28
                        note = a, c, g, or t
source                  1..49
                        mol_type = other DNA
                        organism = synthetic construct
SEQUENCE: 43
acacgacgct cttccgatct nnnnnnnnct atagtacaga cagacttgt              49

SEQ ID NO: 44           moltype = DNA  length = 49
FEATURE                 Location/Qualifiers
misc_feature            1..49
                        note = Synthetic nucleotide
misc_difference         21..28
                        note = a, c, g, or t
source                  1..49
                        mol_type = other DNA
                        organism = synthetic construct
SEQUENCE: 44
acacgacgct cttccgatct nnnnnnnnct gactagcaga cagacttgt              49

SEQ ID NO: 45           moltype = DNA  length = 49
FEATURE                 Location/Qualifiers
misc_feature            1..49
                        note = Synthetic nucleotide
misc_difference         21..28
                        note = a, c, g, or t
source                  1..49
                        mol_type = other DNA
```

```
                        organism = synthetic construct
SEQUENCE: 45
acacgacgct cttccgatct nnnnnnnnct gcagcgcaga cagacttgt              49

SEQ ID NO: 46           moltype = DNA  length = 49
FEATURE                 Location/Qualifiers
misc_feature            1..49
                        note = Synthetic nucleotide
misc_difference         21..28
                        note = a, c, g, or t
source                  1..49
                        mol_type = other DNA
                        organism = synthetic construct
SEQUENCE: 46
acacgacgct cttccgatct nnnnnnnnct gtgatgcaga cagacttgt              49

SEQ ID NO: 47           moltype = DNA  length = 49
FEATURE                 Location/Qualifiers
misc_feature            1..49
                        note = Synthetic nucleotide
misc_difference         21..28
                        note = a, c, g, or t
source                  1..49
                        mol_type = other DNA
                        organism = synthetic construct
SEQUENCE: 47
acacgacgct cttccgatct nnnnnnnnct tagagccaga cagacttgt              49

SEQ ID NO: 48           moltype = DNA  length = 49
FEATURE                 Location/Qualifiers
misc_feature            1..49
                        note = Synthetic nucleotide
misc_difference         21..28
                        note = a, c, g, or t
source                  1..49
                        mol_type = other DNA
                        organism = synthetic construct
SEQUENCE: 48
acacgacgct cttccgatct nnnnnnnnct tgagaccaga cagacttgt              49

SEQ ID NO: 49           moltype = DNA  length = 52
FEATURE                 Location/Qualifiers
misc_feature            1..52
                        note = Synthetic nucleotide
misc_difference         21..28
                        note = a, c, g, or t
source                  1..52
                        mol_type = other DNA
                        organism = synthetic construct
SEQUENCE: 49
acacgacgct cttccgatct nnnnnnnnga ccagcctttc agacagactt gt          52

SEQ ID NO: 50           moltype = DNA  length = 52
FEATURE                 Location/Qualifiers
misc_feature            1..52
                        note = Synthetic nucleotide
misc_difference         21..28
                        note = a, c, g, or t
source                  1..52
                        mol_type = other DNA
                        organism = synthetic construct
SEQUENCE: 50
acacgacgct cttccgatct nnnnnnnnga cgtcgctttc agacagactt gt          52

SEQ ID NO: 51           moltype = DNA  length = 52
FEATURE                 Location/Qualifiers
misc_feature            1..52
                        note = Synthetic nucleotide
misc_difference         21..28
                        note = a, c, g, or t
source                  1..52
                        mol_type = other DNA
                        organism = synthetic construct
SEQUENCE: 51
acacgacgct cttccgatct nnnnnnnnga ctgatctttc agacagactt gt          52

SEQ ID NO: 52           moltype = DNA  length = 52
FEATURE                 Location/Qualifiers
misc_feature            1..52
```

```
                        note = Synthetic nucleotide
misc_difference         21..28
                        note = a, c, g, or t
source                  1..52
                        mol_type = other DNA
                        organism = synthetic construct
SEQUENCE: 52
acacgacgct cttccgatct nnnnnnnnga gccttatttc agacagactt gt          52

SEQ ID NO: 53           moltype = DNA  length = 52
FEATURE                 Location/Qualifiers
misc_feature            1..52
                        note = Synthetic nucleotide
misc_difference         21..28
                        note = a, c, g, or t
source                  1..52
                        mol_type = other DNA
                        organism = synthetic construct
SEQUENCE: 53
acacgacgct cttccgatct nnnnnnnnga gttccatttc agacagactt gt          52

SEQ ID NO: 54           moltype = DNA  length = 52
FEATURE                 Location/Qualifiers
misc_feature            1..52
                        note = Synthetic nucleotide
misc_difference         21..28
                        note = a, c, g, or t
source                  1..52
                        mol_type = other DNA
                        organism = synthetic construct
SEQUENCE: 54
acacgacgct cttccgatct nnnnnnnnga tatcattttc agacagactt gt          52

SEQ ID NO: 55           moltype = DNA  length = 52
FEATURE                 Location/Qualifiers
misc_feature            1..52
                        note = Synthetic nucleotide
misc_difference         21..28
                        note = a, c, g, or t
source                  1..52
                        mol_type = other DNA
                        organism = synthetic construct
SEQUENCE: 55
acacgacgct cttccgatct nnnnnnnnga tcgacttttc agacagactt gt          52

SEQ ID NO: 56           moltype = DNA  length = 52
FEATURE                 Location/Qualifiers
misc_feature            1..52
                        note = Synthetic nucleotide
misc_difference         21..28
                        note = a, c, g, or t
source                  1..52
                        mol_type = other DNA
                        organism = synthetic construct
SEQUENCE: 56
acacgacgct cttccgatct nnnnnnnnga tgctgttttc agacagactt gt          52

SEQ ID NO: 57           moltype = DNA  length = 52
FEATURE                 Location/Qualifiers
misc_feature            1..52
                        note = Synthetic nucleotide
misc_difference         21..28
                        note = a, c, g, or t
source                  1..52
                        mol_type = other DNA
                        organism = synthetic construct
SEQUENCE: 57
acacgacgct cttccgatct nnnnnnnngc agtatctttc agacagactt gt          52

SEQ ID NO: 58           moltype = DNA  length = 52
FEATURE                 Location/Qualifiers
misc_feature            1..52
                        note = Synthetic nucleotide
misc_difference         21..28
                        note = a, c, g, or t
source                  1..52
                        mol_type = other DNA
                        organism = synthetic construct
SEQUENCE: 58
```

```
acacgacgct cttccgatct nnnnnnnngc atgtactttc agacagactt gt          52

SEQ ID NO: 59          moltype = DNA  length = 52
FEATURE                Location/Qualifiers
misc_feature           1..52
                       note = Synthetic nucleotide
misc_difference        21..28
                       note = a, c, g, or t
source                 1..52
                       mol_type = other DNA
                       organism = synthetic construct
SEQUENCE: 59
acacgacgct cttccgatct nnnnnnnngc cagttatttc agacagactt gt          52

SEQ ID NO: 60          moltype = DNA  length = 52
FEATURE                Location/Qualifiers
misc_feature           1..52
                       note = Synthetic nucleotide
misc_difference        21..28
                       note = a, c, g, or t
source                 1..52
                       mol_type = other DNA
                       organism = synthetic construct
SEQUENCE: 60
acacgacgct cttccgatct nnnnnnnngc cgaccatttc agacagactt gt          52

SEQ ID NO: 61          moltype = DNA  length = 54
FEATURE                Location/Qualifiers
misc_feature           1..54
                       note = Synthetic nucleotide
misc_difference        21..28
                       note = a, c, g, or t
source                 1..54
                       mol_type = other DNA
                       organism = synthetic construct
SEQUENCE: 61
acacgacgct cttccgatct nnnnnnnngc cttagatttt tcagacagac ttgt        54

SEQ ID NO: 62          moltype = DNA  length = 54
FEATURE                Location/Qualifiers
misc_feature           1..54
                       note = Synthetic nucleotide
misc_difference        21..28
                       note = a, c, g, or t
source                 1..54
                       mol_type = other DNA
                       organism = synthetic construct
SEQUENCE: 62
acacgacgct cttccgatct nnnnnnnngc gatacttttt tcagacagac ttgt        54

SEQ ID NO: 63          moltype = DNA  length = 54
FEATURE                Location/Qualifiers
misc_feature           1..54
                       note = Synthetic nucleotide
misc_difference        21..28
                       note = a, c, g, or t
source                 1..54
                       mol_type = other DNA
                       organism = synthetic construct
SEQUENCE: 63
acacgacgct cttccgatct nnnnnnnngc gtacattttt tcagacagac ttgt        54

SEQ ID NO: 64          moltype = DNA  length = 54
FEATURE                Location/Qualifiers
misc_feature           1..54
                       note = Synthetic nucleotide
misc_difference        21..28
                       note = a, c, g, or t
source                 1..54
                       mol_type = other DNA
                       organism = synthetic construct
SEQUENCE: 64
acacgacgct cttccgatct nnnnnnnngg cattgttttt tcagacagac ttgt        54

SEQ ID NO: 65          moltype = DNA  length = 54
FEATURE                Location/Qualifiers
misc_feature           1..54
                       note = Synthetic nucleotide
misc_difference        21..28
```

```
                        note = a, c, g, or t
source                  1..54
                        mol_type = other DNA
                        organism = synthetic construct
SEQUENCE: 65
acacgacgct cttccgatct nnnnnnnngg cgccattttt tcagacagac ttgt        54

SEQ ID NO: 66           moltype = DNA  length = 54
FEATURE                 Location/Qualifiers
misc_feature            1..54
                        note = Synthetic nucleotide
misc_difference         21..28
                        note = a, c, g, or t
source                  1..54
                        mol_type = other DNA
                        organism = synthetic construct
SEQUENCE: 66
acacgacgct cttccgatct nnnnnnnngg tgttactttt tcagacagac ttgt        54

SEQ ID NO: 67           moltype = DNA  length = 54
FEATURE                 Location/Qualifiers
misc_feature            1..54
                        note = Synthetic nucleotide
misc_difference         21..28
                        note = a, c, g, or t
source                  1..54
                        mol_type = other DNA
                        organism = synthetic construct
SEQUENCE: 67
acacgacgct cttccgatct nnnnnnnngt acgcattttt tcagacagac ttgt        54

SEQ ID NO: 68           moltype = DNA  length = 54
FEATURE                 Location/Qualifiers
misc_feature            1..54
                        note = Synthetic nucleotide
misc_difference         21..28
                        note = a, c, g, or t
source                  1..54
                        mol_type = other DNA
                        organism = synthetic construct
SEQUENCE: 68
acacgacgct cttccgatct nnnnnnnngt cggctgtttt tcagacagac ttgt        54

SEQ ID NO: 69           moltype = DNA  length = 54
FEATURE                 Location/Qualifiers
misc_feature            1..54
                        note = Synthetic nucleotide
misc_difference         21..28
                        note = a, c, g, or t
source                  1..54
                        mol_type = other DNA
                        organism = synthetic construct
SEQUENCE: 69
acacgacgct cttccgatct nnnnnnnngt gacatctttt tcagacagac ttgt        54

SEQ ID NO: 70           moltype = DNA  length = 54
FEATURE                 Location/Qualifiers
misc_feature            1..54
                        note = Synthetic nucleotide
misc_difference         21..28
                        note = a, c, g, or t
source                  1..54
                        mol_type = other DNA
                        organism = synthetic construct
SEQUENCE: 70
acacgacgct cttccgatct nnnnnnnngt gcatactttt tcagacagac ttgt        54

SEQ ID NO: 71           moltype = DNA  length = 54
FEATURE                 Location/Qualifiers
misc_feature            1..54
                        note = Synthetic nucleotide
misc_difference         21..28
                        note = a, c, g, or t
source                  1..54
                        mol_type = other DNA
                        organism = synthetic construct
SEQUENCE: 71
acacgacgct cttccgatct nnnnnnnngt gtgcgctttt tcagacagac ttgt        54
```

```
SEQ ID NO: 72           moltype = DNA  length = 54
FEATURE                 Location/Qualifiers
misc_feature            1..54
                        note = Synthetic nucleotide
misc_difference         21..28
                        note = a, c, g, or t
source                  1..54
                        mol_type = other DNA
                        organism = synthetic construct
SEQUENCE: 72
acacgacgct cttccgatct nnnnnnnngt tagccatttt tcagacagac ttgt        54

SEQ ID NO: 73           moltype = DNA  length = 49
FEATURE                 Location/Qualifiers
misc_feature            1..49
                        note = Synthetic nucleotide
misc_difference         29..36
                        note = a,c, or t
source                  1..49
                        mol_type = other DNA
                        organism = synthetic construct
SEQUENCE: 73
acacgacgct cttccgatct gttccagahh hhhhhhcaga cagacttgt               49

SEQ ID NO: 74           moltype = DNA  length = 49
FEATURE                 Location/Qualifiers
misc_feature            1..49
                        note = Synthetic nucleotide
misc_difference         29..36
                        note = a,c, or t
source                  1..49
                        mol_type = other DNA
                        organism = synthetic construct
SEQUENCE: 74
acacgacgct cttccgatct tacgtgcahh hhhhhhcaga cagacttgt               49

SEQ ID NO: 75           moltype = DNA  length = 49
FEATURE                 Location/Qualifiers
misc_feature            1..49
                        note = Synthetic nucleotide
misc_difference         29..36
                        note = a,c, or t
source                  1..49
                        mol_type = other DNA
                        organism = synthetic construct
SEQUENCE: 75
acacgacgct cttccgatct tactgcgahh hhhhhhcaga cagacttgt               49

SEQ ID NO: 76           moltype = DNA  length = 49
FEATURE                 Location/Qualifiers
misc_feature            1..49
                        note = Synthetic nucleotide
misc_difference         29..36
                        note = a,c, or t
source                  1..49
                        mol_type = other DNA
                        organism = synthetic construct
SEQUENCE: 76
acacgacgct cttccgatct tagagccthh hhhhhhcaga cagacttgt               49

SEQ ID NO: 77           moltype = DNA  length = 49
FEATURE                 Location/Qualifiers
misc_feature            1..49
                        note = Synthetic nucleotide
misc_difference         29..36
                        note = a,c, or t
source                  1..49
                        mol_type = other DNA
                        organism = synthetic construct
SEQUENCE: 77
acacgacgct cttccgatct tagccagthh hhhhhhcaga cagacttgt               49

SEQ ID NO: 78           moltype = DNA  length = 49
FEATURE                 Location/Qualifiers
misc_feature            1..49
                        note = Synthetic nucleotide
misc_difference         29..36
                        note = a,c, or t
source                  1..49
```

```
                        mol_type = other DNA
                        organism = synthetic construct
SEQUENCE: 78
acacgacgct cttccgatct tatcgcaghh hhhhhhcaga cagacttgt              49

SEQ ID NO: 79           moltype = DNA  length = 49
FEATURE                 Location/Qualifiers
misc_feature            1..49
                        note = Synthetic nucleotide
misc_difference         29..36
                        note = a,c, or t
source                  1..49
                        mol_type = other DNA
                        organism = synthetic construct
SEQUENCE: 79
acacgacgct cttccgatct tcagtcgahh hhhhhhcaga cagacttgt              49

SEQ ID NO: 80           moltype = DNA  length = 49
FEATURE                 Location/Qualifiers
misc_feature            1..49
                        note = Synthetic nucleotide
misc_difference         29..36
                        note = a,c, or t
source                  1..49
                        mol_type = other DNA
                        organism = synthetic construct
SEQUENCE: 80
acacgacgct cttccgatct tcatgatahh hhhhhhcaga cagacttgt              49

SEQ ID NO: 81           moltype = DNA  length = 49
FEATURE                 Location/Qualifiers
misc_feature            1..49
                        note = Synthetic nucleotide
misc_difference         29..36
                        note = a,c, or t
source                  1..49
                        mol_type = other DNA
                        organism = synthetic construct
SEQUENCE: 81
acacgacgct cttccgatct tccagagthh hhhhhhcaga cagacttgt              49

SEQ ID NO: 82           moltype = DNA  length = 49
FEATURE                 Location/Qualifiers
misc_feature            1..49
                        note = Synthetic nucleotide
misc_difference         29..36
                        note = a,c, or t
source                  1..49
                        mol_type = other DNA
                        organism = synthetic construct
SEQUENCE: 82
acacgacgct cttccgatct tccgagathh hhhhhhcaga cagacttgt              49

SEQ ID NO: 83           moltype = DNA  length = 49
FEATURE                 Location/Qualifiers
misc_feature            1..49
                        note = Synthetic nucleotide
misc_difference         29..36
                        note = a,c, or t
source                  1..49
                        mol_type = other DNA
                        organism = synthetic construct
SEQUENCE: 83
acacgacgct cttccgatct tcgatcaghh hhhhhhcaga cagacttgt              49

SEQ ID NO: 84           moltype = DNA  length = 49
FEATURE                 Location/Qualifiers
misc_feature            1..49
                        note = Synthetic nucleotide
misc_difference         29..36
                        note = a,c, or t
source                  1..49
                        mol_type = other DNA
                        organism = synthetic construct
SEQUENCE: 84
acacgacgct cttccgatct tcgcgacghh hhhhhhcaga cagacttgt              49

SEQ ID NO: 85           moltype = DNA  length = 49
FEATURE                 Location/Qualifiers
```

```
misc_feature            1..49
                        note = Synthetic nucleotide
misc_difference         29
                        note = a,c, or t
misc_difference         30
                        note = a, c, g, or t
misc_difference         31
                        note = a,c, or t
misc_difference         32
                        note = a, c, g, or t
misc_difference         33
                        note = a,c, or t
misc_difference         34
                        note = a, c, g, or t
misc_difference         35
                        note = a,c, or t
misc_difference         36
                        note = a, c, g, or t
source                  1..49
                        mol_type = other DNA
                        organism = synthetic construct
SEQUENCE: 85
acacgacgct cttccgatct tcggctgghn hnhnhncaga cagacttgt              49

SEQ ID NO: 86           moltype = DNA  length = 49
FEATURE                 Location/Qualifiers
misc_feature            1..49
                        note = Synthetic nucleotide
misc_difference         29
                        note = a,c, or t
misc_difference         30
                        note = a, c, g, or t
misc_difference         31
                        note = a,c, or t
misc_difference         32
                        note = a, c, g, or t
misc_difference         33
                        note = a,c, or t
misc_difference         34
                        note = a, c, g, or t
misc_difference         35
                        note = a,c, or t
misc_difference         36
                        note = a, c, g, or t
source                  1..49
                        mol_type = other DNA
                        organism = synthetic construct
SEQUENCE: 86
acacgacgct cttccgatct tcgtagtghn hnhnhncaga cagacttgt              49

SEQ ID NO: 87           moltype = DNA  length = 49
FEATURE                 Location/Qualifiers
misc_feature            1..49
                        note = Synthetic nucleotide
misc_difference         29
                        note = a,c, or t
misc_difference         30
                        note = a, c, g, or t
misc_difference         31
                        note = a,c, or t
misc_difference         32
                        note = a, c, g, or t
misc_difference         33
                        note = a,c, or t
misc_difference         34
                        note = a, c, g, or t
misc_difference         35
                        note = a,c, or t
misc_difference         36
                        note = a, c, g, or t
source                  1..49
                        mol_type = other DNA
                        organism = synthetic construct
SEQUENCE: 87
acacgacgct cttccgatct tgaccgathn hnhnhncaga cagacttgt              49

SEQ ID NO: 88           moltype = DNA  length = 49
FEATURE                 Location/Qualifiers
misc_feature            1..49
```

```
                        note = Synthetic nucleotide
misc_difference         29
                        note = a,c, or t
misc_difference         30
                        note = a, c, g, or t
misc_difference         31
                        note = a,c, or t
misc_difference         32
                        note = a, c, g, or t
misc_difference         33
                        note = a,c, or t
misc_difference         34
                        note = a, c, g, or t
misc_difference         35
                        note = a,c, or t
misc_difference         36
                        note = a, c, g, or t
source                  1..49
                        mol_type = other DNA
                        organism = synthetic construct
SEQUENCE: 88
acacgacgct cttccgatct tgagaccthn hnhnhncaga cagacttgt              49

SEQ ID NO: 89           moltype = DNA  length = 49
FEATURE                 Location/Qualifiers
misc_feature            1..49
                        note = Synthetic nucleotide
misc_difference         29
                        note = a,c, or t
misc_difference         30
                        note = a, c, g, or t
misc_difference         31
                        note = a,c, or t
misc_difference         32
                        note = a, c, g, or t
misc_difference         33
                        note = a,c, or t
misc_difference         34
                        note = a, c, g, or t
misc_difference         35
                        note = a,c, or t
misc_difference         36
                        note = a, c, g, or t
source                  1..49
                        mol_type = other DNA
                        organism = synthetic construct
SEQUENCE: 89
acacgacgct cttccgatct tgcatacghn hnhnhncaga cagacttgt              49

SEQ ID NO: 90           moltype = DNA  length = 49
FEATURE                 Location/Qualifiers
misc_feature            1..49
                        note = Synthetic nucleotide
misc_difference         29
                        note = a,c, or t
misc_difference         30
                        note = a, c, g, or t
misc_difference         31
                        note = a,c, or t
misc_difference         32
                        note = a, c, g, or t
misc_difference         33
                        note = a,c, or t
misc_difference         34
                        note = a, c, g, or t
misc_difference         35
                        note = a,c, or t
misc_difference         36
                        note = a, c, g, or t
source                  1..49
                        mol_type = other DNA
                        organism = synthetic construct
SEQUENCE: 90
acacgacgct cttccgatct tgcgcgtghn hnhnhncaga cagacttgt              49

SEQ ID NO: 91           moltype = DNA  length = 49
FEATURE                 Location/Qualifiers
misc_feature            1..49
                        note = Synthetic nucleotide
```

```
misc_difference        29
                       note = a,c, or t
misc_difference        30
                       note = a, c, g, or t
misc_difference        31
                       note = a,c, or t
misc_difference        32
                       note = a, c, g, or t
misc_difference        33
                       note = a,c, or t
misc_difference        34
                       note = a, c, g, or t
misc_difference        35
                       note = a,c, or t
misc_difference        36
                       note = a, c, g, or t
source                 1..49
                       mol_type = other DNA
                       organism = synthetic construct
SEQUENCE: 91
acacgacgct cttccgatct tgctacaghn hnhnhncaga cagacttgt              49

SEQ ID NO: 92          moltype = DNA  length = 49
FEATURE                Location/Qualifiers
misc_feature           1..49
                       note = Synthetic nucleotide
misc_difference        29
                       note = a,c, or t
misc_difference        30
                       note = a, c, g, or t
misc_difference        31
                       note = a,c, or t
misc_difference        32
                       note = a, c, g, or t
misc_difference        33
                       note = a,c, or t
misc_difference        34
                       note = a, c, g, or t
misc_difference        35
                       note = a,c, or t
misc_difference        36
                       note = a, c, g, or t
source                 1..49
                       mol_type = other DNA
                       organism = synthetic construct
SEQUENCE: 92
acacgacgct cttccgatct tgtacgcahn hnhnhncaga cagacttgt              49

SEQ ID NO: 93          moltype = DNA  length = 49
FEATURE                Location/Qualifiers
misc_feature           1..49
                       note = Synthetic nucleotide
misc_difference        29
                       note = a,c, or t
misc_difference        30
                       note = a, c, g, or t
misc_difference        31
                       note = a,c, or t
misc_difference        32
                       note = a, c, g, or t
misc_difference        33
                       note = a,c, or t
misc_difference        34
                       note = a, c, g, or t
misc_difference        35
                       note = a,c, or t
misc_difference        36
                       note = a, c, g, or t
source                 1..49
                       mol_type = other DNA
                       organism = synthetic construct
SEQUENCE: 93
acacgacgct cttccgatct ttacggtghn hnhnhncaga cagacttgt              49

SEQ ID NO: 94          moltype = DNA  length = 49
FEATURE                Location/Qualifiers
misc_feature           1..49
                       note = Synthetic nucleotide
misc_difference        29
```

```
                        note = a,c, or t
misc_difference         30
                        note = a, c, g, or t
misc_difference         31
                        note = a,c, or t
misc_difference         32
                        note = a, c, g, or t
misc_difference         33
                        note = a,c, or t
misc_difference         34
                        note = a, c, g, or t
misc_difference         35
                        note = a,c, or t
misc_difference         36
                        note = a, c, g, or t
source                  1..49
                        mol_type = other DNA
                        organism = synthetic construct
SEQUENCE: 94
acacgacgct cttccgatct ttagccaghn hnhnhncaga cagacttgt              49

SEQ ID NO: 95           moltype = DNA  length = 49
FEATURE                 Location/Qualifiers
misc_feature            1..49
                        note = Synthetic nucleotide
misc_difference         29
                        note = a,c, or t
misc_difference         30
                        note = a, c, g, or t
misc_difference         31
                        note = a,c, or t
misc_difference         32
                        note = a, c, g, or t
misc_difference         33
                        note = a,c, or t
misc_difference         34
                        note = a, c, g, or t
misc_difference         35
                        note = a,c, or t
misc_difference         36
                        note = a, c, g, or t
source                  1..49
                        mol_type = other DNA
                        organism = synthetic construct
SEQUENCE: 95
acacgacgct cttccgatct ttgaccgahn hnhnhncaga cagacttgt              49

SEQ ID NO: 96           moltype = DNA  length = 49
FEATURE                 Location/Qualifiers
misc_feature            1..49
                        note = Synthetic nucleotide
misc_difference         29
                        note = a,c, or t
misc_difference         30
                        note = a, c, g, or t
misc_difference         31
                        note = a,c, or t
misc_difference         32
                        note = a, c, g, or t
misc_difference         33
                        note = a,c, or t
misc_difference         34
                        note = a, c, g, or t
misc_difference         35
                        note = a,c, or t
misc_difference         36
                        note = a, c, g, or t
source                  1..49
                        mol_type = other DNA
                        organism = synthetic construct
```

-continued

```
SEQUENCE: 96
acacgacgct cttccgatct ttgtggcahn hnhnhncaga cagacttgt              49

SEQ ID NO: 97          moltype = DNA  length = 20
FEATURE                Location/Qualifiers
misc_feature           1..20
                       note = Anchor sequence
source                 1..20
                       mol_type = other DNA
                       organism = synthetic construct
SEQUENCE: 97
acacgacgct cttccgatct                                              20
```

What is claimed is:

1. A reverse transcription reaction composition comprising[;]:

mRNA;

a reverse transcriptase; and at least 1000 unique oligonucleotide species, each unique oligonucleotide species comprising a barcode region and a uniform region, the barcode region comprising a molecule barcode comprising at least 7 nucleotides and having a constraint on G content, wherein the uniform region is 3' of the barcode region, the uniform region comprising a target-specific region 3' of the barcode region, the target-specific region comprising at least 10 nucleotides complementary to a target nucleic acid, wherein the unique oligonucleotide species comprise different nucleic acid sequences in their barcode regions, wherein the constraint on G content comprises:

(a) less than 1% of the unique oligonucleotide species comprising the molecule barcode [have] *having* a G content of 50% or more[:]; and/or (b) the molecule barcodes of all of the unique oligonucleotide species in the composition collectively have a G content of no more than 12.5%, and wherein the barcode region further comprises a sample barcode comprising at least 3 nucleotides.

2. The composition of claim 1, wherein the constraint on G content is less than 1% of the unique oligonucleotide species comprising the molecule barcode [have] *having* a G content of 50% or more.

3. The composition of claim 1, wherein the constraint on G content is the molecule barcodes of all of the unique oligonucleotide species in the composition collectively have a G content of no more than 12.5%.

4. The composition of claim 1, wherein the unique oligonucleotide species are disposed in at least two spatially isolated pools, each pool comprising at least 100 unique oligonucleotides of the unique oligonucleotide species, wherein unique oligonucleotides in the same pool comprise the same sample barcode sequence, and wherein different unique oligonucleotides of the same pool comprise a different molecule barcode sequences.

5. The composition of claim 4, wherein the unique oligonucleotide species of each pool are immobilized on a substrate, so that the sample barcodes but not the molecule barcodes are the same for the oligonucleotide species immobilized on each substrate.

6. The composition of claim 1, wherein for at least 95% of the unique oligonucleotide species, any G in the molecule barcode is not adjacent to another G.

7. The composition of claim 1, wherein at least 95% of the molecule barcodes of the unique oligonucleotide species comprise the sequence HNHNHNHN, wherein each "H" is any one of A, C, or T, and wherein each "N" is any one of A, G, C, or T.

8. The composition of claim 1, wherein each of the unique oligonucleotide species comprises a spacer 3' of the barcode region and 5' of the target specific region, said spacer comprising the sequence HHHHHHHH, wherein each "H" is any one of A, C, or T.

9. The composition of claim 1, wherein each oligonucleotide species has a length of 24-140 nucleotides.

10. The composition of claim 1, wherein the composition comprises at least two oligonucleotides of the same unique oligonucleotide species.

11. The composition of claim 1, wherein the uniform region comprises a target-specific region comprising a sequence flanking an immune cell receptor or immunoglobulin variable region coding sequence.

12. The composition of claim 11, wherein the immune cell receptor variable region coding sequence is selected from the group consisting of: a T cell receptor variable region coding sequence, a B cell receptor variable region coding sequence, and a combination thereof.

13. The composition of claim 1, wherein the molecule barcodes of all of the unique oligonucleotide species in the composition collectively have a G content of 2.5%-10%.

14. The composition of claim 1, wherein the molecule barcode is 7-9 nucleotides.

15. The composition of claim 1, comprising at least 6,500 unique oligonucleotide species.

16. A method of specifically barcoding cDNA from two or more samples, each sample comprising nucleic acids, the method comprising:

contacting each sample with a pool comprising at least 100 unique oligonucleotide species, wherein each sample is contacted in spatial isolation from the other samples, each unique oligonucleotide species comprising:

a barcode region comprising[:]:

a molecule barcode comprising at least 7 nucleotides and having a constraint on G content; [and]

a sample barcode comprising at least 3 nucleotides; and a uniform region 3' of the barcode region, the uniform region comprising a target-specific region 3' of the barcode region, the target-specific region comprising at least 10 nucleotides complementary to a target nucleic acid, wherein the unique [polynucleotide] *oligonucleotide* species of each pool comprise the same sample barcode, and comprise different molecule barcodes, and wherein the constraint on G content comprises:

(a) less than 1% of the unique oligonucleotide species comprising the molecule barcode [have] *having* a G content of 50% or more; and/or (b) the molecule barcodes of all of the unique oligonucleotide species collectively have a G content of no more than 12.5%;

hybridizing target-specific regions of at least some oligonucleotides of the unique oligonucleotide species to at least some of the nucleic acids of the sample, wherein the nucleic acids comprise mRNA; and extending the hybridized oligonucleotides by reverse transcription, thereby producing extended strands comprising an oligonucleotide of the unique oligonucleotide species and a sequence complementary to the target, wherein for each sample, the extended strands comprise the same sample barcode and different molecule barcodes, wherein for different samples, the molecule barcodes are different, and wherein a bias in representation of the unique oligonucleotide species in an amplification product of the extended strands is reduced in comparison to the use of control unique oligonucleotide species comprising control molecule barcodes without the constraint on G content.

17. The method of claim 16, further comprising ascertaining nucleic acid sequences of the strands comprising the oligonucleotides of the unique oligonucleotide species and the sequence complementary to the target.

18. The method of claim 16, wherein the constraint on G content is the molecule barcodes of the unique oligonucleotide species collectively having a G content of less than 12.5%.

19. The method of claim 16, wherein the molecule barcode is 7-9 nucleotides.

20. The method of claim 16, the pool comprises at least 1000 unique oligonucleotide species.

21. The method of claim 16, the pool comprises at least 6,500 unique oligonucleotide species.

22. A kit for amplifying barcoded cDNA comprising an immune cell receptor or immunoglobulin variable region coding sequence, comprising[;]:

a composition comprising: at least 1000 unique oligonucleotide species, each unique oligonucleotide species comprising a barcode region and a uniform region, the barcode region comprising a molecule barcode comprising at least 7 nucleotides and having a constraint on G content, wherein the uniform region is 3' of the barcode region, the uniform region comprising a target-specific region 3' of the barcode region, the target-specific region comprising at least 10 nucleotides complementary to a target nucleic acid, wherein the unique oligonucleotide species comprise different nucleic acid sequences in their barcode regions, wherein the constraint on G content comprises:

(a) less than 1% of the unique oligonucleotide species comprising the molecule barcode [have] *having* a G content of 50% or more; and/or (b) the molecule barcodes of all of the unique oligonucleotide species in the composition collectively have a G content of no more than 12.5%, wherein the barcode region further comprises a sample barcode comprising at least 3 nucleotides, and wherein the uniform region comprises a target-specific region comprising a sequence flanking an immune cell receptor or immunoglobulin variable region coding sequence; and a primer configured to hybridize on an opposite side of the variable region as the target-specific region, and to hybridize to a complementary strand to a strand hybridized by the target-specific region, and is thereby configured to amplify the variable region in conjunction with the target-specific region.

23. The kit of claim 22, wherein the molecule barcode is 7-9 nucleotides.

24. The kit of claim 22, wherein composition comprises at least 6,500 unique oligonucleotide species.

*25. A composition comprising:*

*at least 1000 unique oligonucleotide species, each unique oligonucleotide species comprising a barcode region and a uniform region, the barcode region comprising a molecule barcode comprising at least 7 nucleotides and having a constraint on G content,*

*wherein the uniform region is 3' of the barcode region, the uniform region comprising a target-specific region 3' of the barcode region, the target-specific region comprising at least 10 nucleotides complementary to a target nucleic acid,*

*wherein the unique oligonucleotide species comprise different nucleic acid sequences in their barcode regions,*

*wherein the constraint on G content comprises:*

*(a) less than 1% of the unique oligonucleotide species comprising the molecule barcode having a G content of 50% or more; and/or*

*(b) the molecule barcodes of all of the unique oligonucleotide species in the composition collectively have a G content of no more than 12.5%, and*

*wherein the barcode region further comprises a sample barcode comprising at least 3 nucleotides.*

*26. The composition of claim 25, wherein the constraint on G content is less than 1% of the unique oligonucleotide species comprising the molecule barcode having a G content of 50% or more.*

*27. The composition of claim 25, wherein the constraint on G content is the molecule barcodes of all of the unique oligonucleotide species in the composition collectively have a G content of no more than 12.5%.*

*28. The composition of claim 25, wherein the unique oligonucleotide species are disposed in at least two spatially isolated pools, each pool comprising at least 100 unique oligonucleotides of the unique oligonucleotide species, wherein unique oligonucleotides in the same pool comprise the same sample barcode sequence, and wherein different unique oligonucleotides of the same pool comprise a different molecule barcode sequences.*

*29. The composition of claim 28, wherein the unique oligonucleotide species of each pool are immobilized on a substrate, so that the sample barcodes but not the molecule barcodes are the same for the oligonucleotide species immobilized on each substrate.*

*30. The composition of claim 25, wherein for at least 95% of the unique oligonucleotide species, any G in the molecule barcode is not adjacent to another G.*

*31. The composition of claim 25, wherein at least 95% of the molecule barcodes of the unique oligonucleotide species comprise the sequence HNHNHNHN, wherein each "H" is any one of A, C, or T, and wherein each "N" is any one of A, G, C, or T.*

*32. The composition of claim 25, wherein each of the unique oligonucleotide species comprises a spacer 3' of the barcode region and 5' of the target specific region, said spacer comprising the sequence HHHHHHHH, wherein each "H" is any one of A, C, or T.*

*33. The composition of claim 25, wherein each oligonucleotide species has a length of 24-140 nucleotides.*

*34. The composition of claim 25, wherein the composition comprises at least two oligonucleotides of the same unique oligonucleotide species.*

*35. The composition of claim 25, wherein the uniform region comprises a target-specific region comprising a sequence flanking an immune cell receptor or immunoglobulin variable region coding sequence.*

*36. The composition of claim 35, wherein the immune cell receptor variable region coding sequence is selected from the group consisting of: a T cell receptor variable region coding sequence, a B cell receptor variable region coding sequence, and a combination thereof.*

*37. The composition of claim 25, wherein the molecule barcodes of all of the unique oligonucleotide species in the composition collectively have a G content of 2.5%-10%.*

*38. The composition of claim 25, wherein the molecule barcode is 7-9 nucleotides.*

*39. The composition of claim 25, comprising at least 6,500 unique oligonucleotide species.*

*40. The method of claim 16, wherein the constraint on G content is less than 1% of the unique oligonucleotide species comprising the molecule barcode having a G content of 50% or more.*

*41. The method of claim 16, wherein the unique oligonucleotide species of each pool are immobilized on a substrate, so that the sample barcodes but not the molecule barcodes are the same for the oligonucleotide species immobilized on each substrate.*

*42. The method of claim 16, wherein for at least 95% of the unique oligonucleotide species, any G in the molecule barcode is not adjacent to another G.*

*43. The method of claim 16, wherein at least 95% of the molecule barcodes of the unique oligonucleotide species comprise the sequence HNHNHNHN, wherein each "H" is any one of A, C, or T, and wherein each "N" is any one of A, G, C, or T.*

*44. The method of claim 16, wherein each of the unique oligonucleotide species comprises a spacer 3' of the barcode region and 5' of the target specific region, said spacer comprising the sequence HHHHHHHH, wherein each "H" is any one of A, C, or T.*

*45. The method of claim 16, wherein each oligonucleotide species has a length of 24-140 nucleotides.*

*46. The method of claim 16, wherein the target-specific region comprises a sequence flanking an immune cell receptor or immunoglobulin variable region coding sequence.*

*47. The method of claim 46, wherein the immune cell receptor variable region coding sequence is selected from the group consisting of: a T cell receptor variable region coding sequence, a B cell receptor variable region coding sequence, and a combination thereof.*

*48. The kit of claim 22, wherein the constraint on G content is the molecule barcodes of the unique oligonucleotide species collectively having a G content of less than 12.5%.*

*49. The kit of claim 22, wherein the constraint on G content is less than 1% of the unique oligonucleotide species comprising the molecule barcode having a G content of 50% or more.*

*50. The kit of claim 22, wherein the unique oligonucleotide species of each pool are immobilized on a substrate, so that the sample barcodes but not the molecule barcodes are the same for the oligonucleotide species immobilized on each substrate.*

*51. The kit of claim 22, wherein for at least 95% of the unique oligonucleotide species, any G in the molecule barcode is not adjacent to another G.*

*52. The kit of claim 22, wherein at least 95% of the molecule barcodes of the unique oligonucleotide species comprise the sequence HNHNHNHN, wherein each "H" is any one of A, C, or T, and wherein each "N" is any one of A, G, C, or T.*

*53. The kit of claim 22, wherein each of the unique oligonucleotide species comprises a spacer 3' of the barcode region and 5' of the target specific region, said spacer comprising the sequence HHHHHHHH, wherein each "H" is any one of A, C, or T.*

*54. The kit of claim 22, wherein each oligonucleotide species has a length of 24-140 nucleotides.*

* * * * *